United States Patent
Suzuki et al.

(10) Patent No.: US 8,606,130 B2
(45) Date of Patent: Dec. 10, 2013

(54) TONER-DENSITY CALCULATING METHOD, REFLECTIVE OPTICAL SENSOR, AND IMAGE FORMING APPARATUS

(71) Applicants: Hidemasa Suzuki, Tokyo (JP); Koji Masuda, Kanagawa (JP)

(72) Inventors: Hidemasa Suzuki, Tokyo (JP); Koji Masuda, Kanagawa (JP)

(73) Assignee: Ricoh Company, Limited, Tokyo (JP)

( * ) Notice: Subject to any disclaimer, the term of this patent is extended or adjusted under 35 U.S.C. 154(b) by 0 days.

(21) Appl. No.: 13/793,973

(22) Filed: Mar. 11, 2013

(65) Prior Publication Data

US 2013/0251389 A1    Sep. 26, 2013

Related U.S. Application Data

(63) Continuation of application No. 12/763,695, filed on Apr. 20, 2010, now Pat. No. 8,396,385.

(30) Foreign Application Priority Data

Apr. 20, 2009  (JP) ................................. 2009-101691
Sep. 15, 2009  (JP) ................................. 2009-213665

(51) Int. Cl.
*G03G 15/00*    (2006.01)

(52) U.S. Cl.
USPC ............................................................ 399/49

(58) Field of Classification Search
USPC ............................................. 399/49, 60, 72, 74
See application file for complete search history.

(56) References Cited

U.S. PATENT DOCUMENTS

| | | | |
|---|---|---|---|
| 6,348,937 B2 * | 2/2002 | Hata | 347/116 |
| 8,249,477 B2 * | 8/2012 | Masuda et al. | 399/60 |
| 8,260,164 B2 * | 9/2012 | Masuda | 399/49 |

* cited by examiner

*Primary Examiner* — Walter L Lindsay, Jr.
*Assistant Examiner* — Rodney Bonnette
(74) *Attorney, Agent, or Firm* — Dickstein Shapiro LLP

(57) ABSTRACT

In a reflective optical sensor in an image forming apparatus, an output from each N number of light-receiving elements (N≥3), obtained when M number of light-emitting elements (M≥3) included in a light-emitting unit emit detecting light, is separated into an amount of specularly reflected light and an amount of diffusely reflected light. The toner density of a pattern, which is formed on a supporting member in the image forming apparatus, is calculated based on a sum of the amounts of specularly reflected light and a sum of the amounts of diffusely reflected light.

19 Claims, 54 Drawing Sheets

FIG. 36
FIG. 37
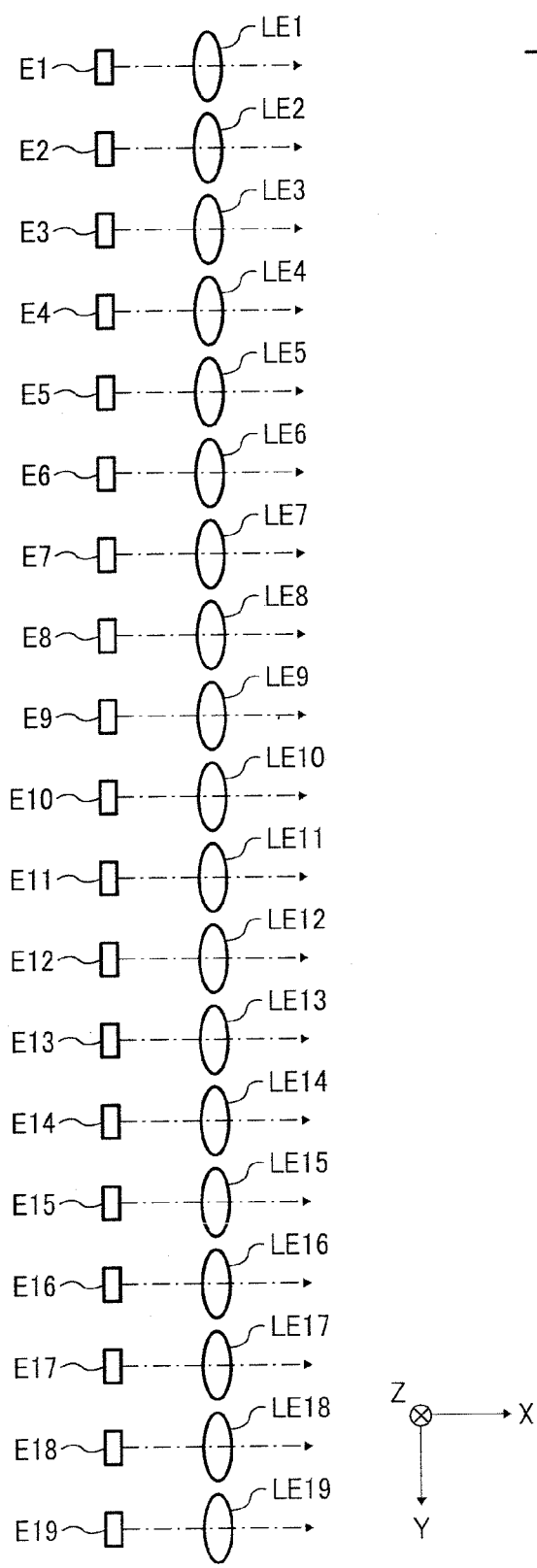

FIG. 38
FIG. 39
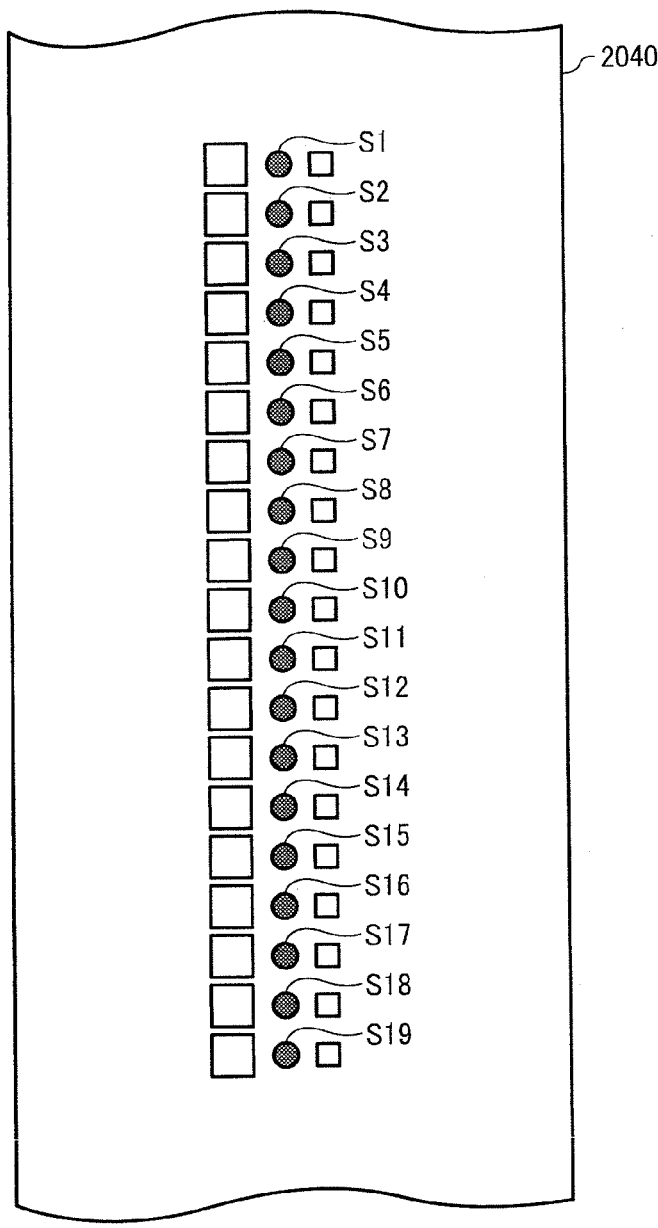
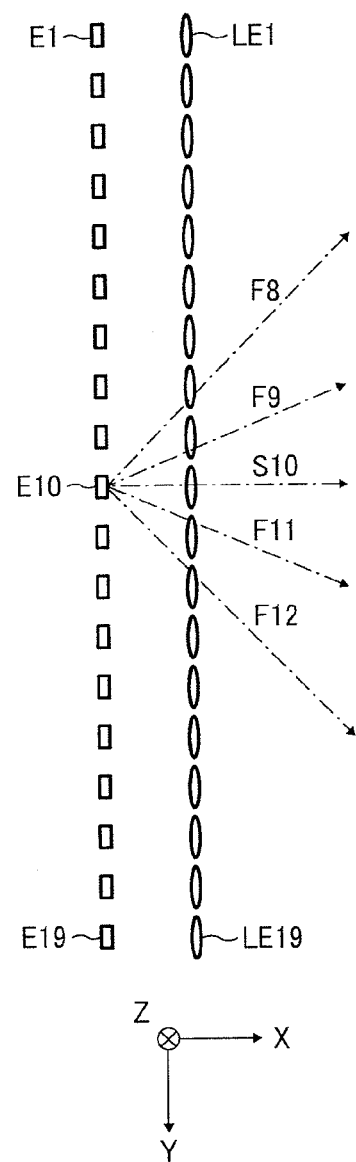

FIG. 40
FIG. 41
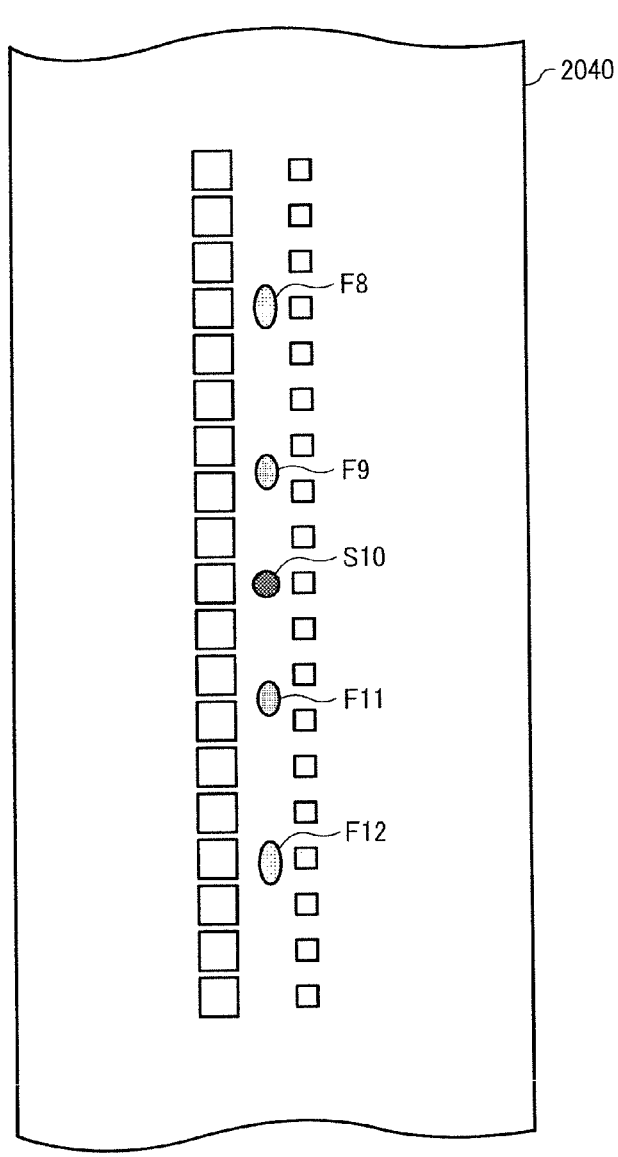
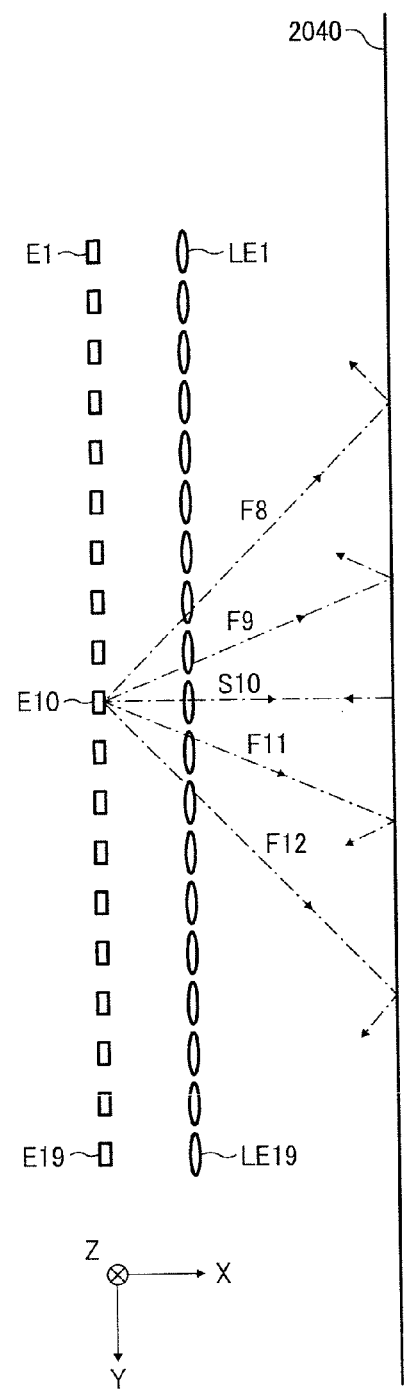
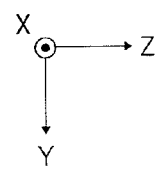
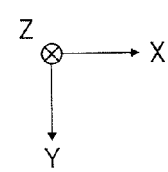

FIG. 44
FIG. 45
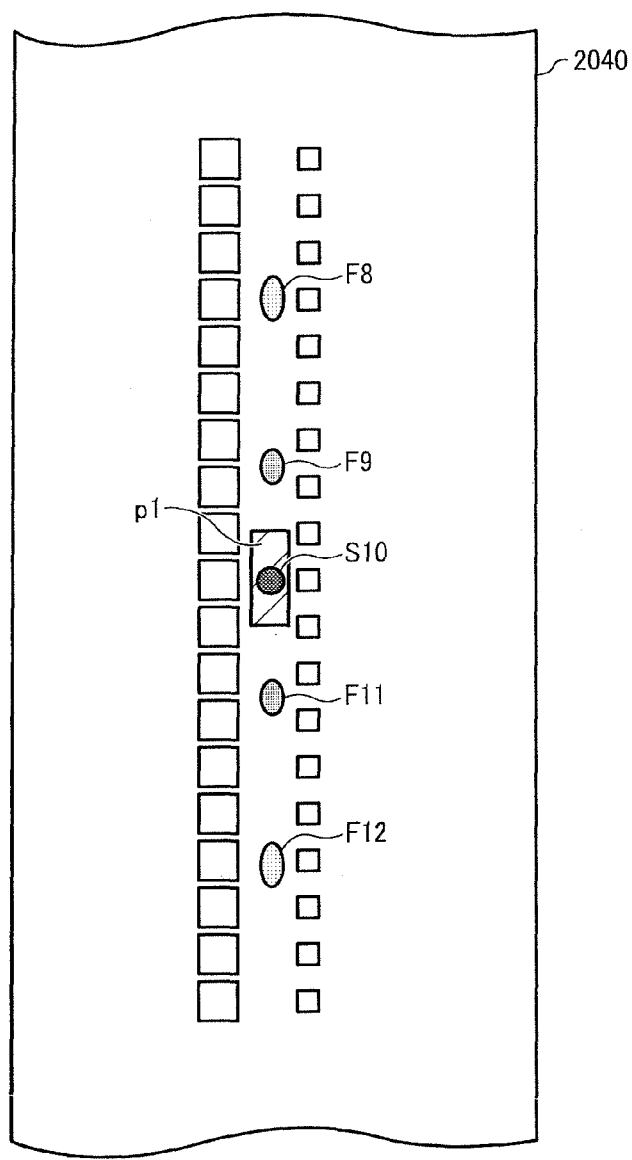
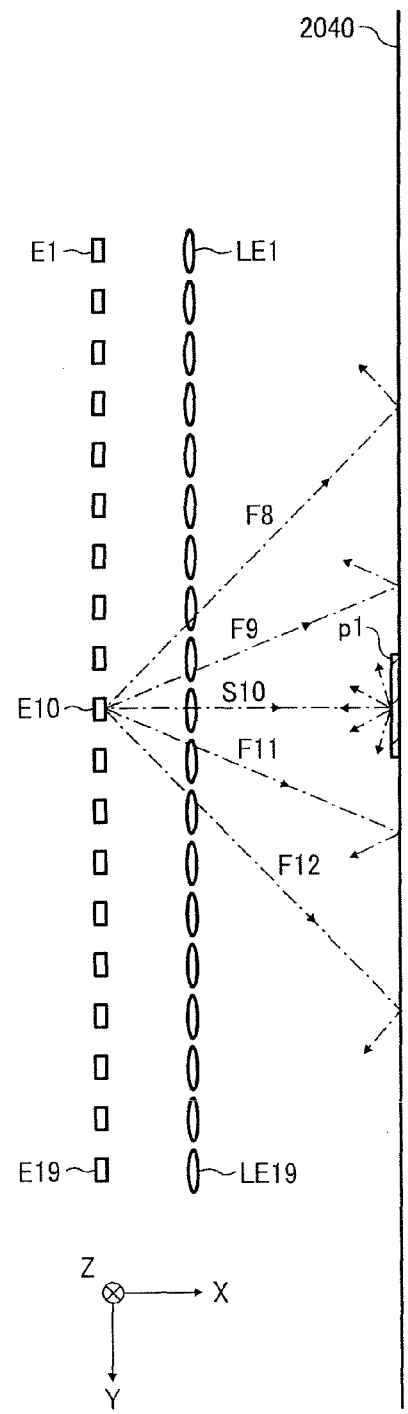
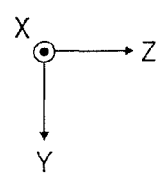
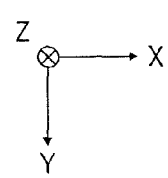

⊠ : SPECULARLY REFLECTED LIGHT + DIFFUSELY REFLECTED LIGHT
▤ : SPECULARLY REFLECTED LIGHT
▨ : DIFFUSELY REFLECTED LIGHT

FIG. 48
FIG. 49
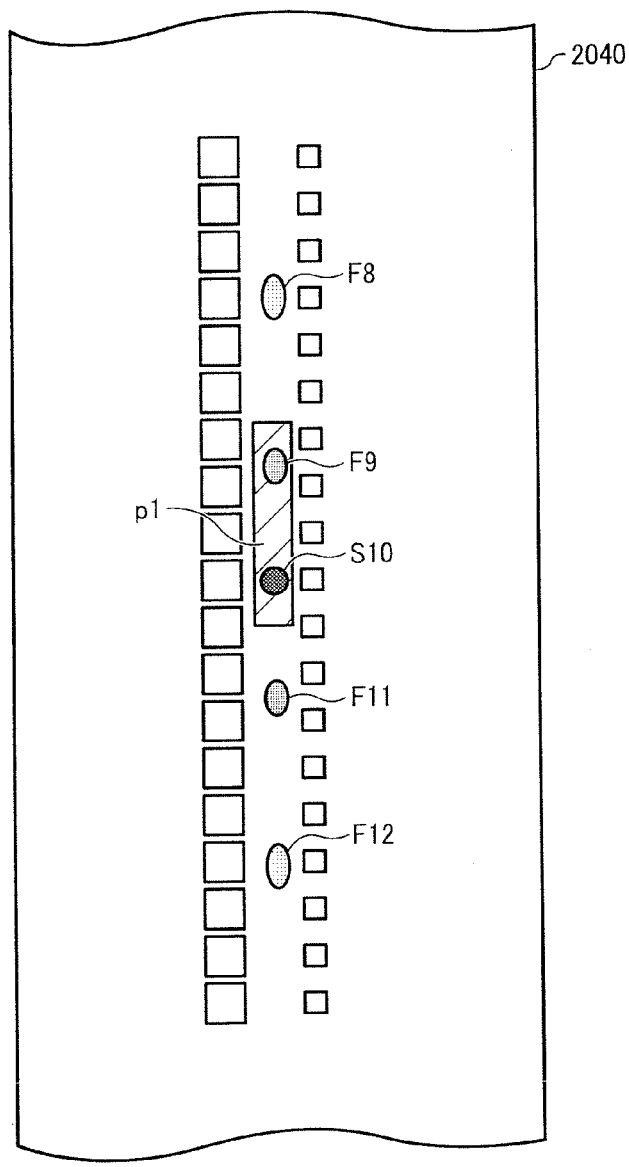
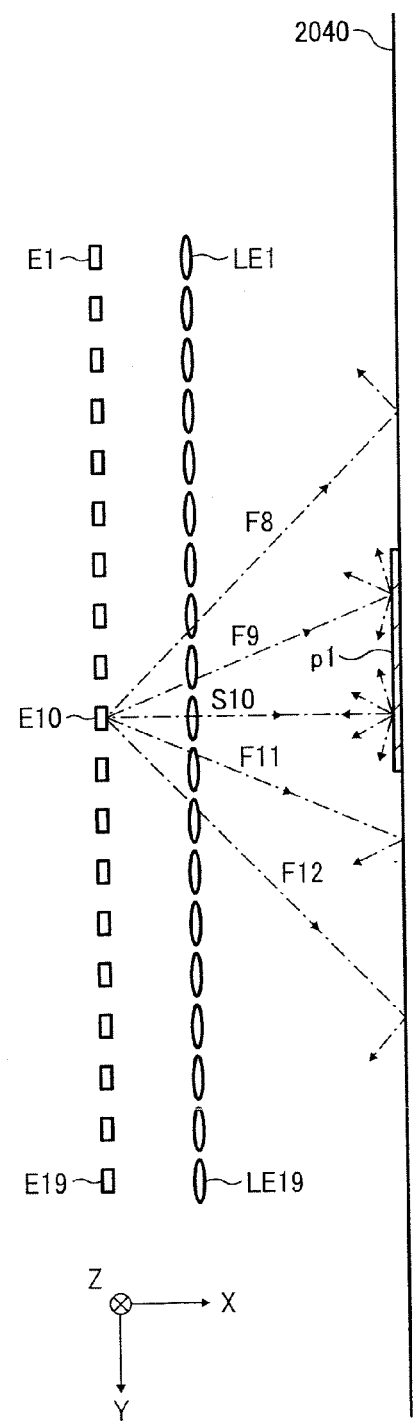

⊠ : SPECULARLY REFLECTED LIGHT + DIFFUSELY REFLECTED LIGHT
▨ : SPECULARLY REFLECTED LIGHT
▨ : DIFFUSELY REFLECTED LIGHT

FIG. 53
FIG. 54
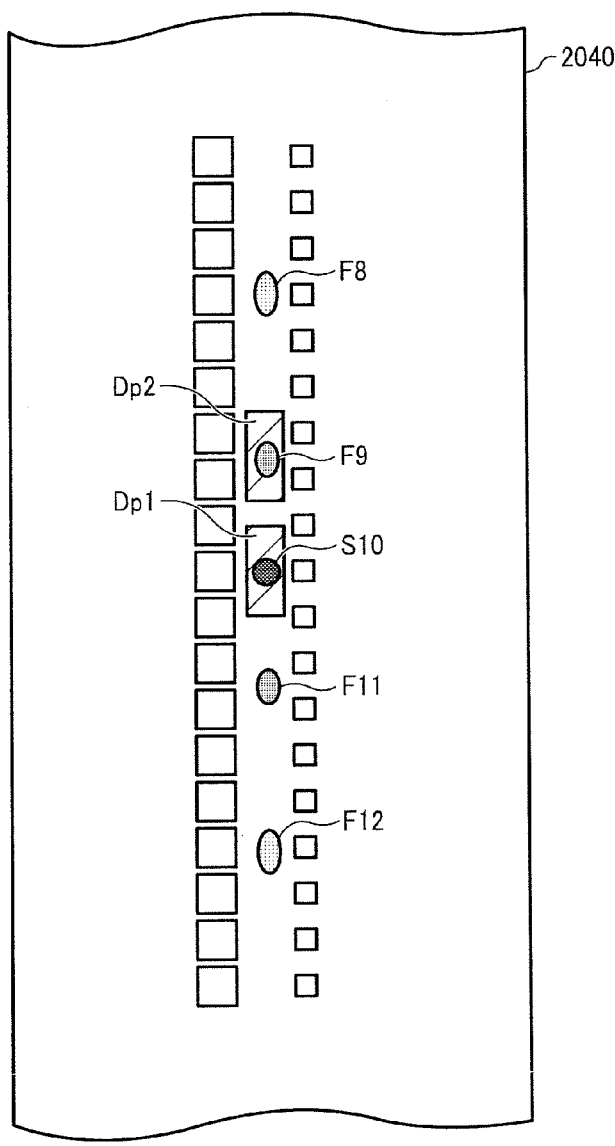
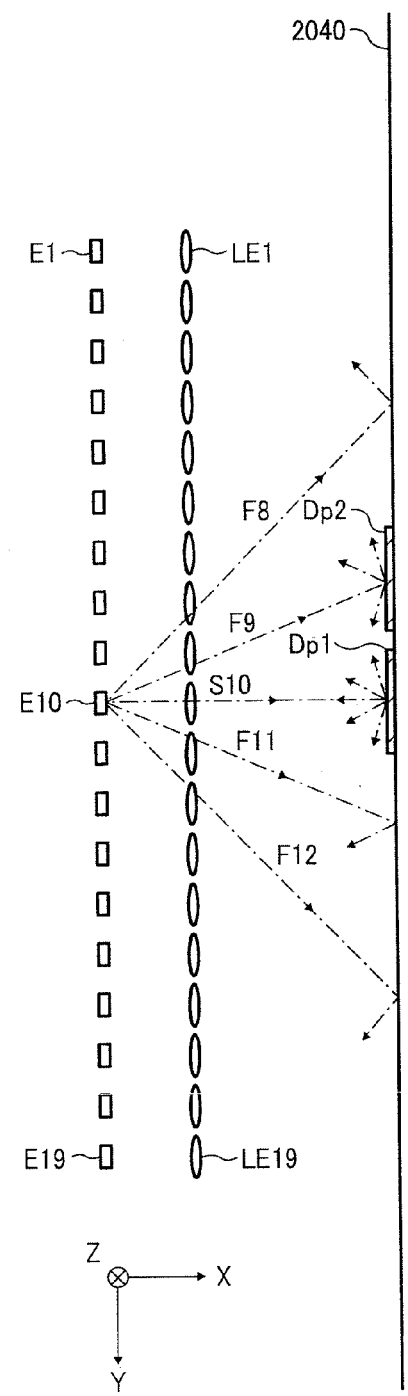

FIG. 55
FIG. 56
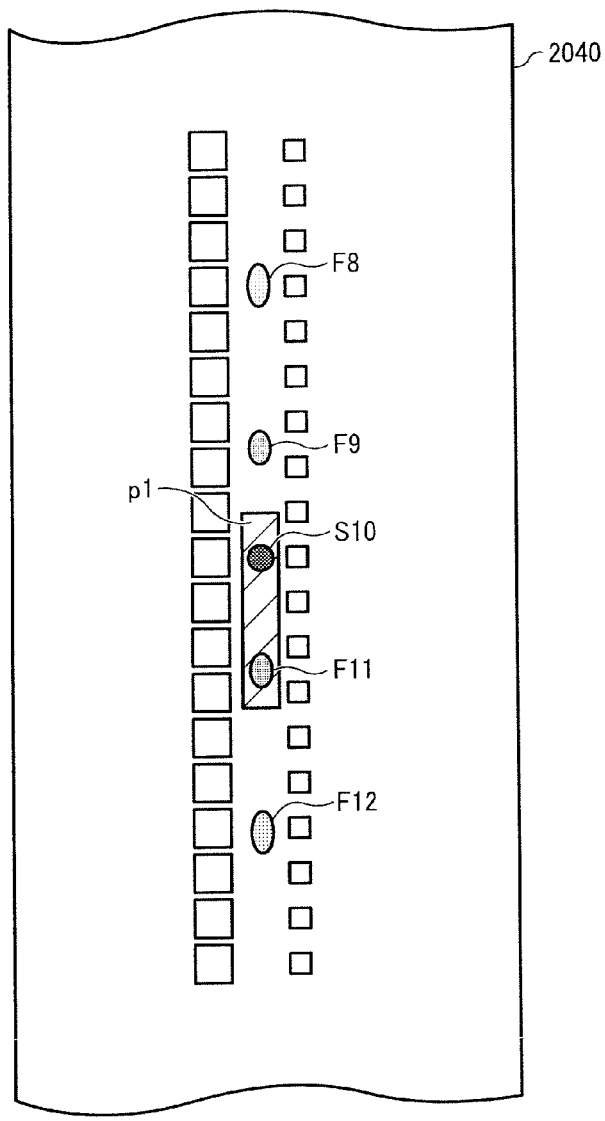
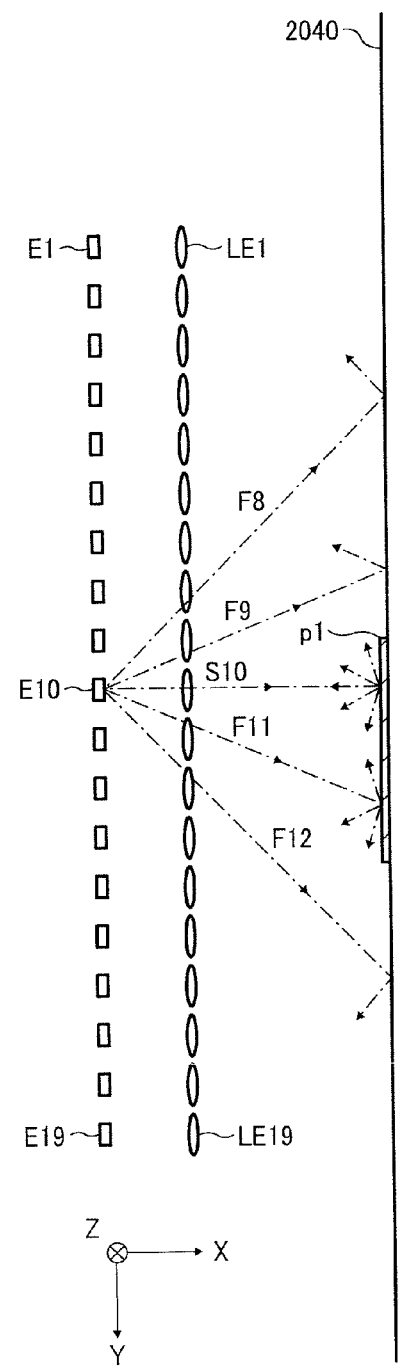

FIG. 58
FIG. 59
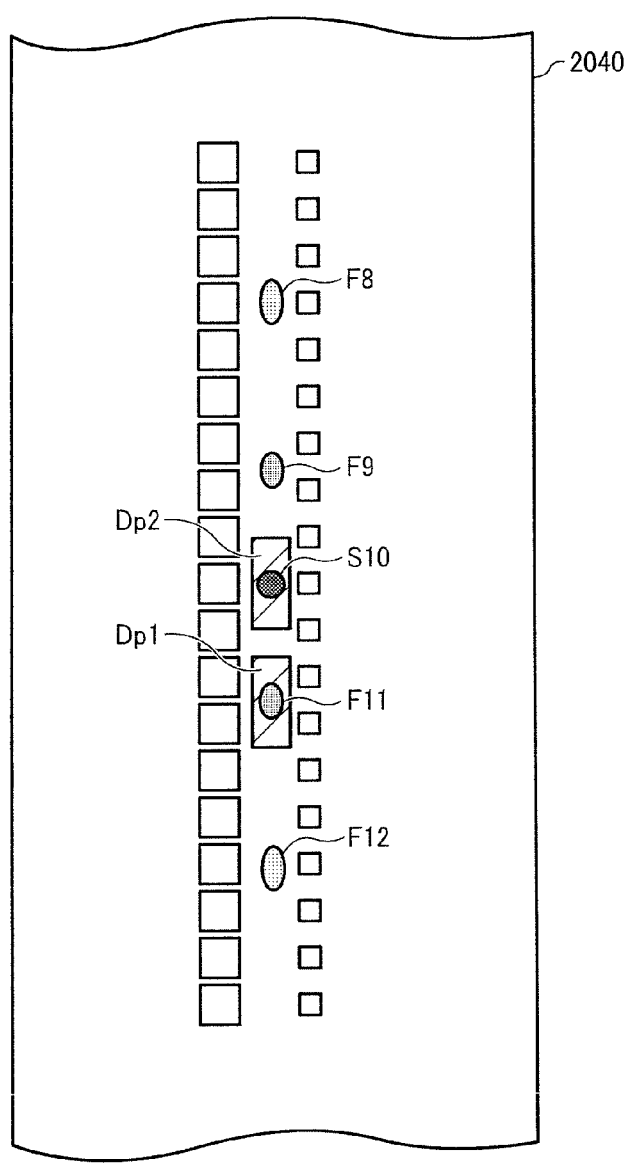
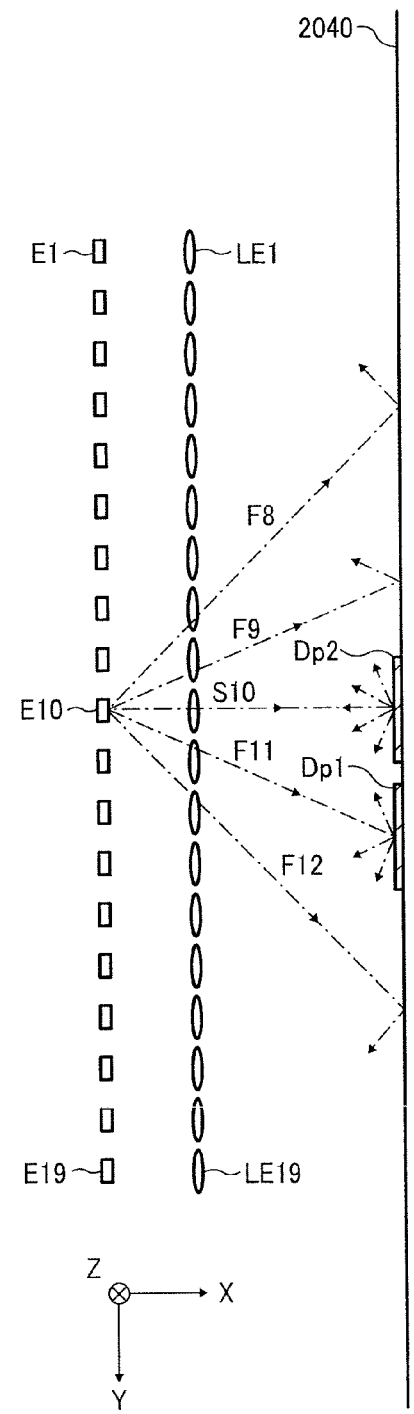

FIG. 60
FIG. 61
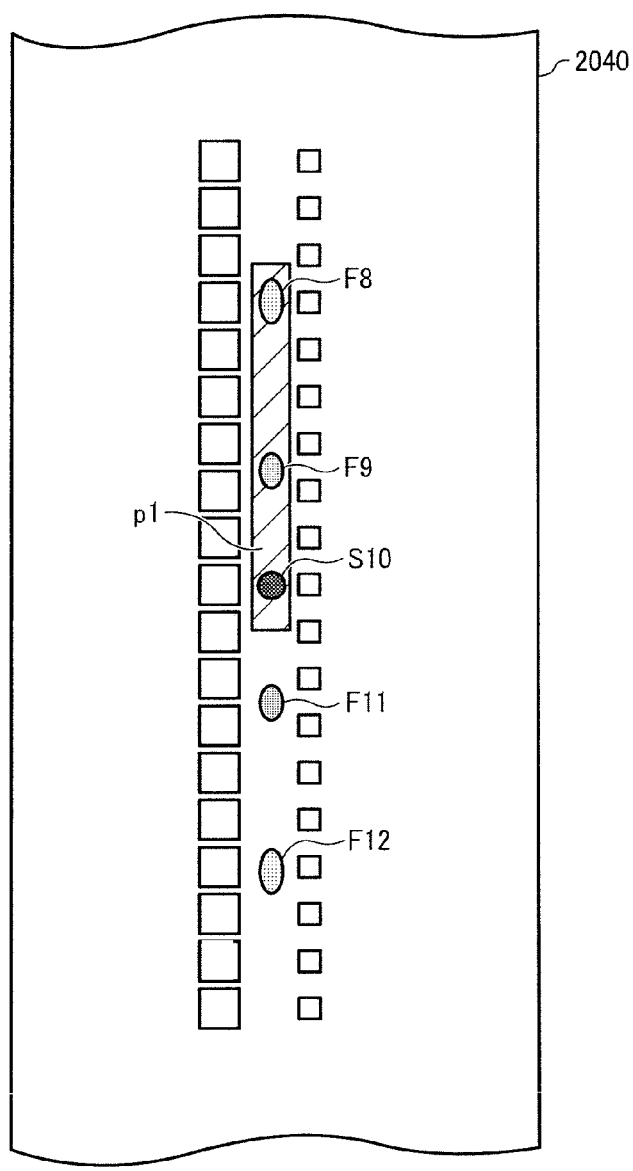
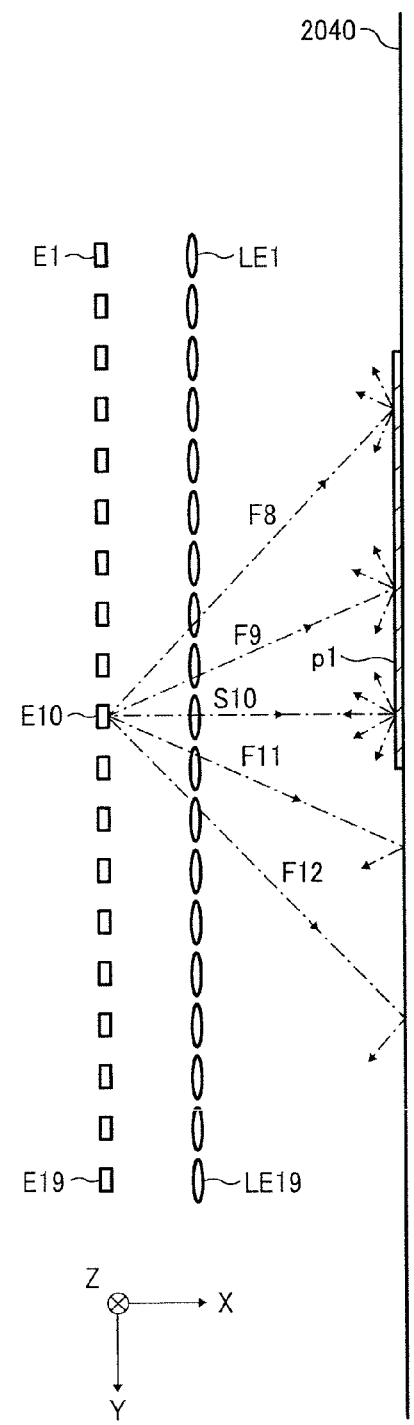

☒ : SPECULARLY REFLECTED LIGHT + DIFFUSELY REFLECTED LIGHT
▣ : SPECULARLY REFLECTED LIGHT
▨ : DIFFUSELY REFLECTED LIGHT

FIG. 65
FIG. 66
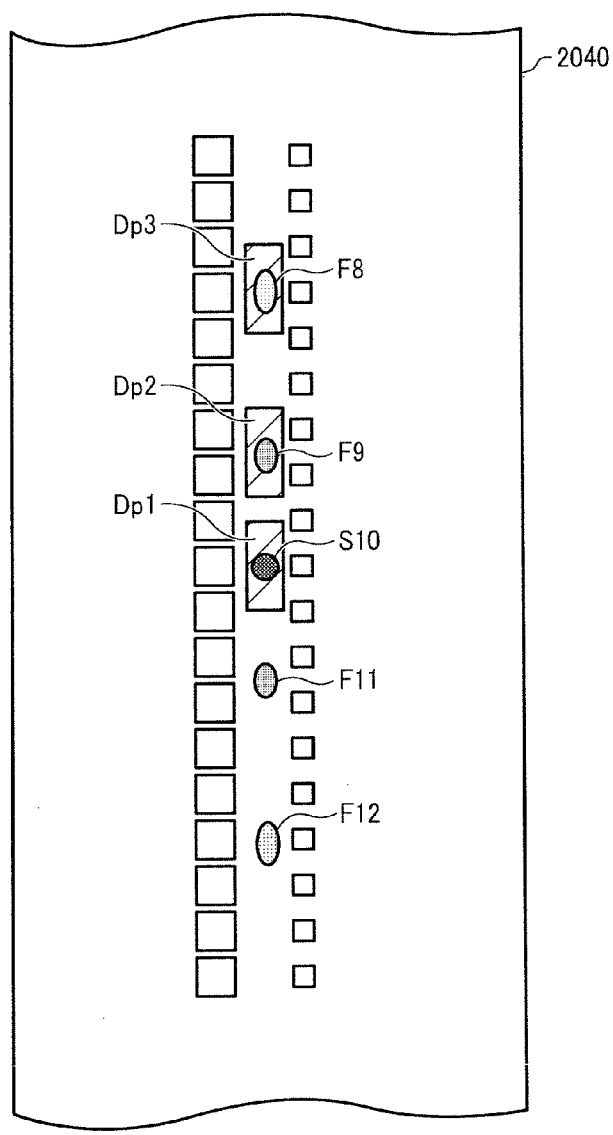
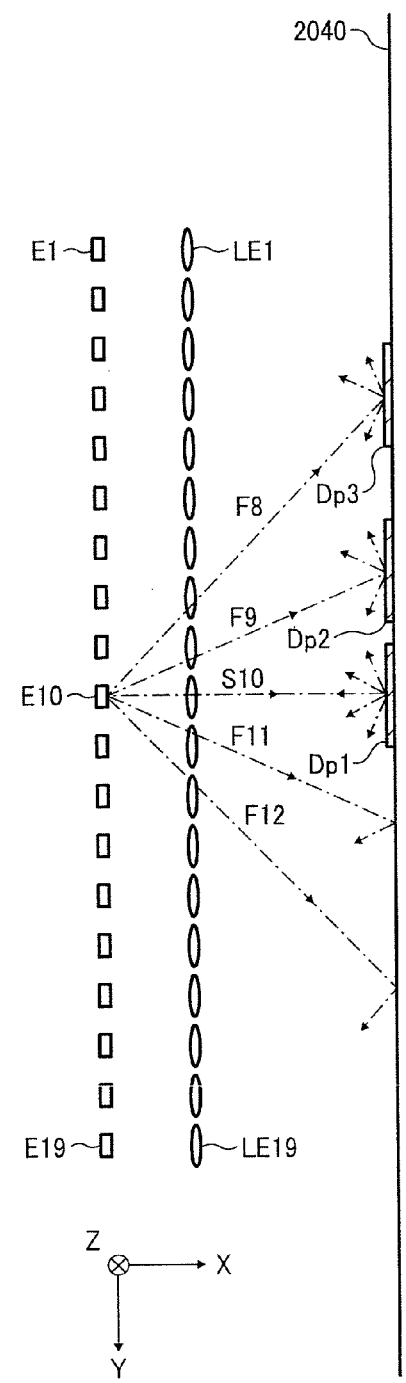

FIG. 67
FIG. 68
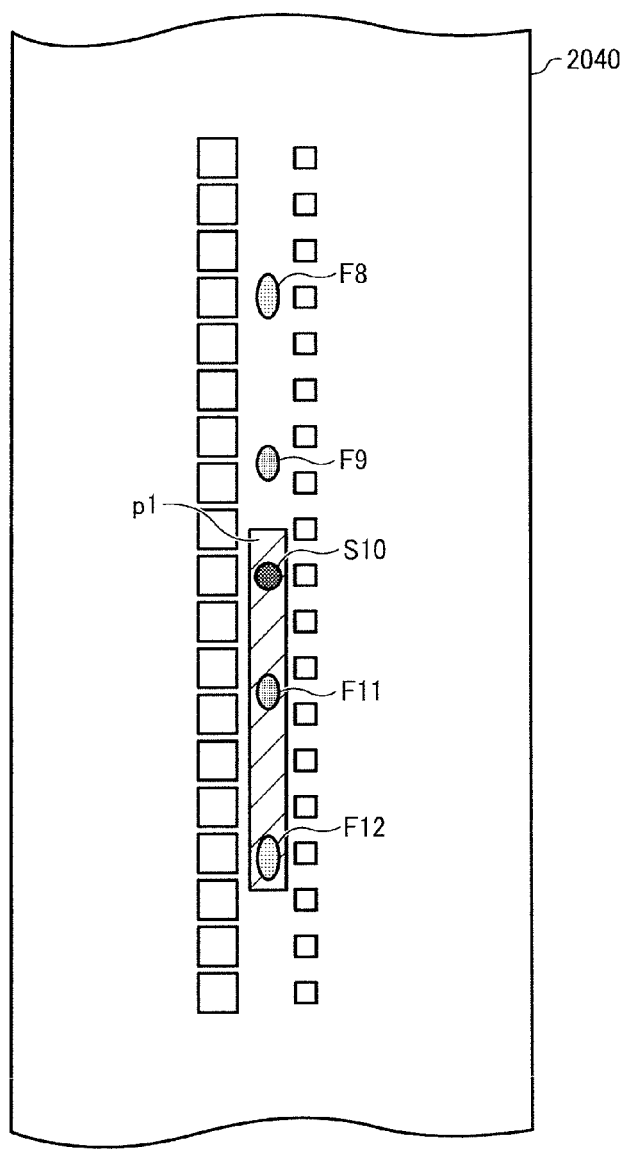
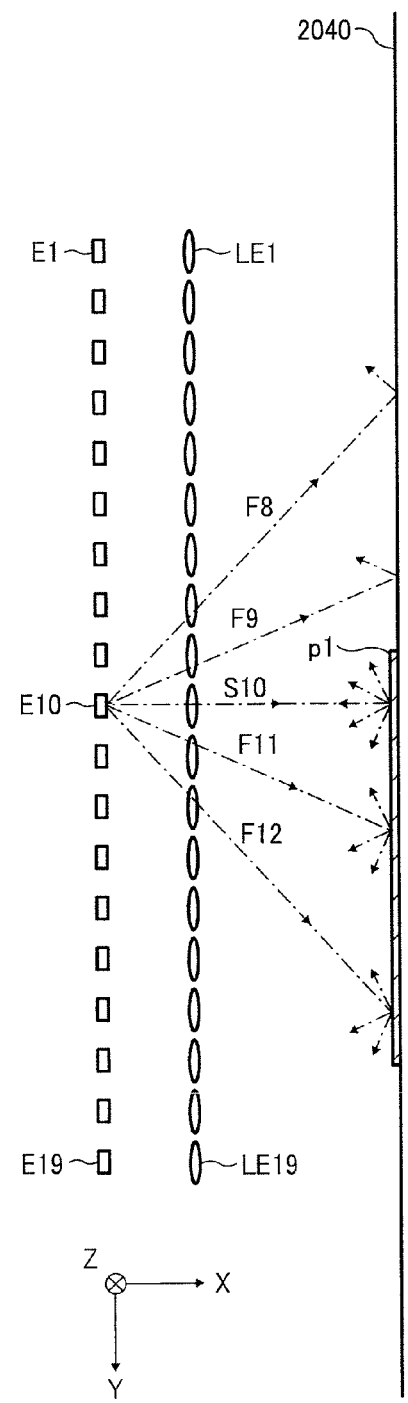
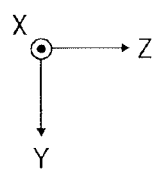
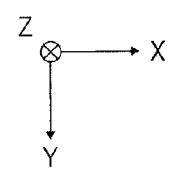

MOVING DIRECTION OF TRANSFER BELT

FIG. 71
FIG. 72
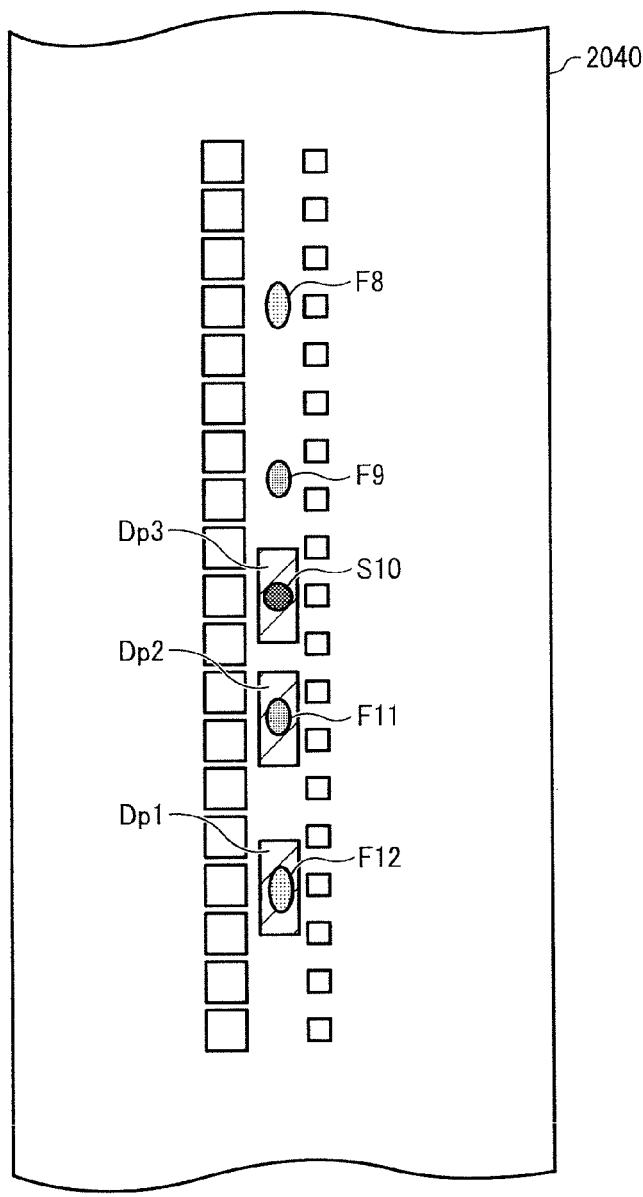
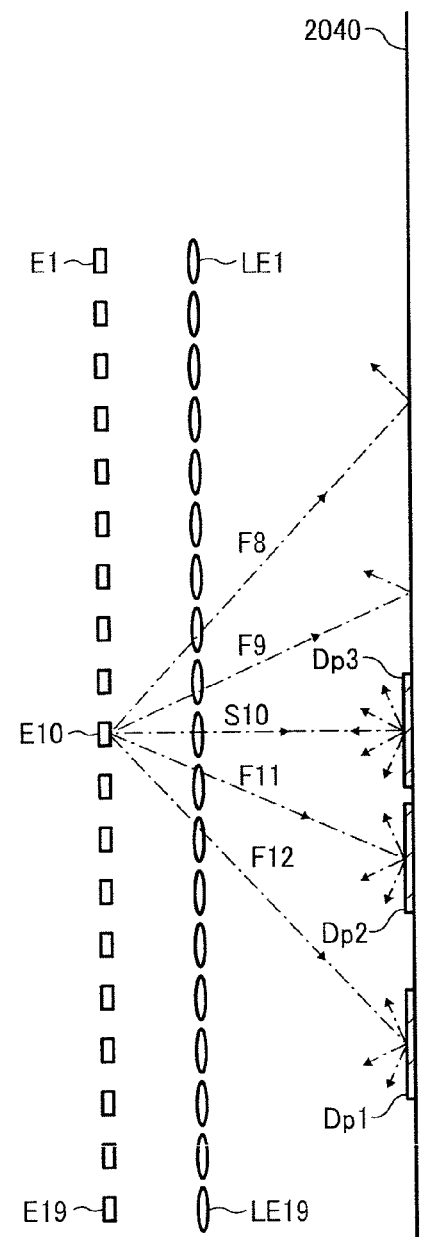

FIG. 73
FIG. 74
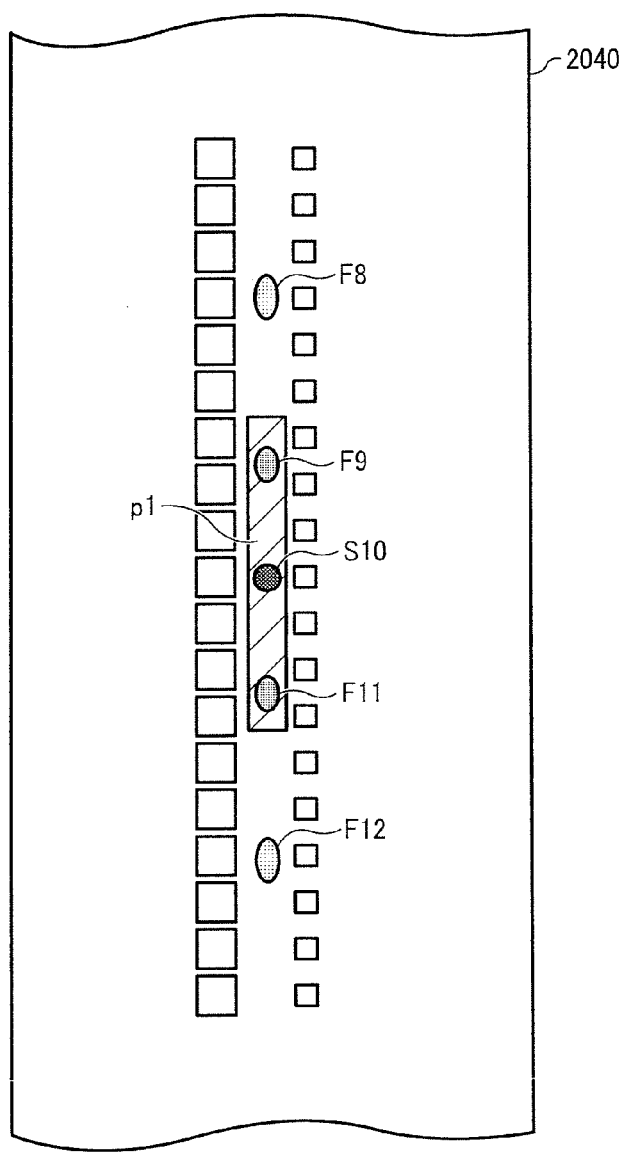
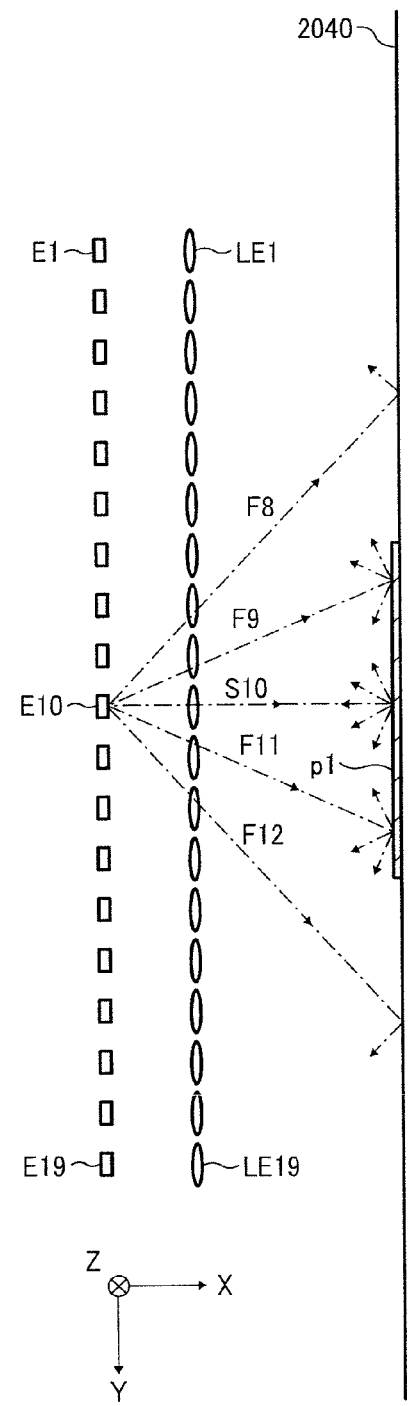

⊠ : SPECULARLY REFLECTED LIGHT + DIFFUSELY REFLECTED LIGHT
▣ : SPECULARLY REFLECTED LIGHT
▢ : DIFFUSELY REFLECTED LIGHT

FIG. 78
FIG. 79
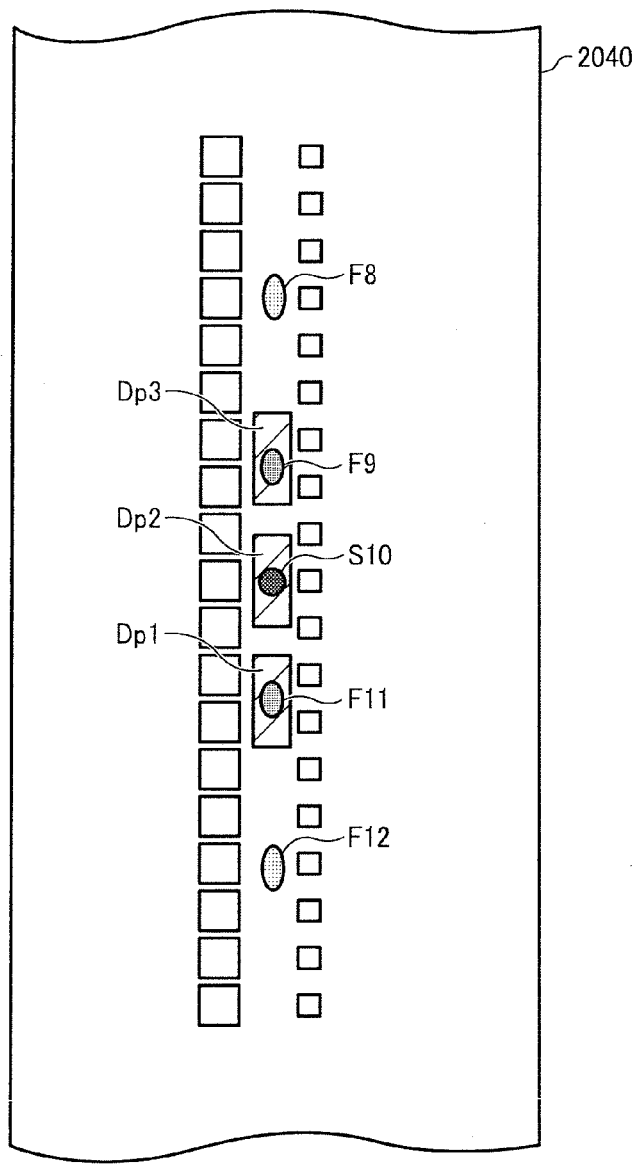
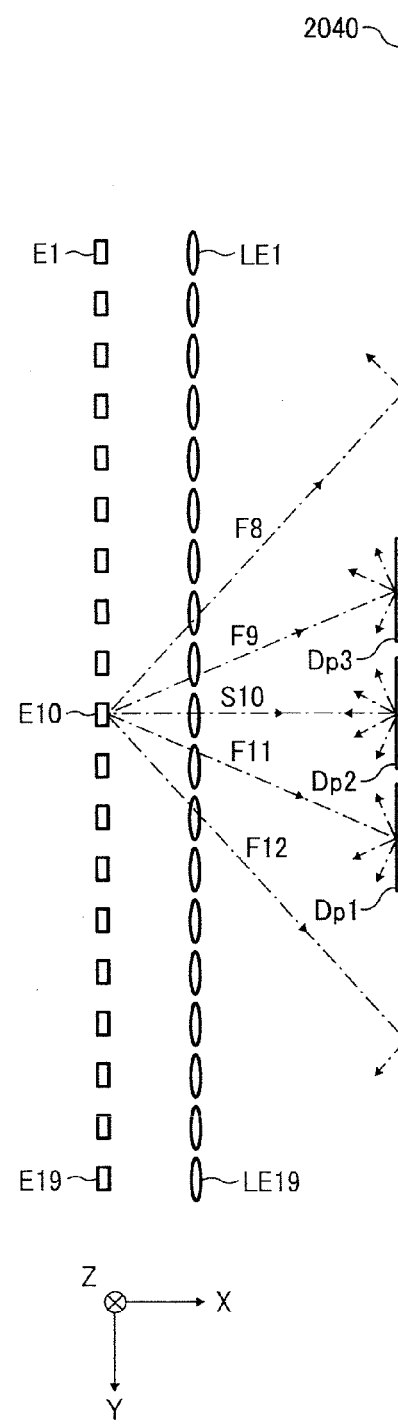

FIG. 80
FIG. 81
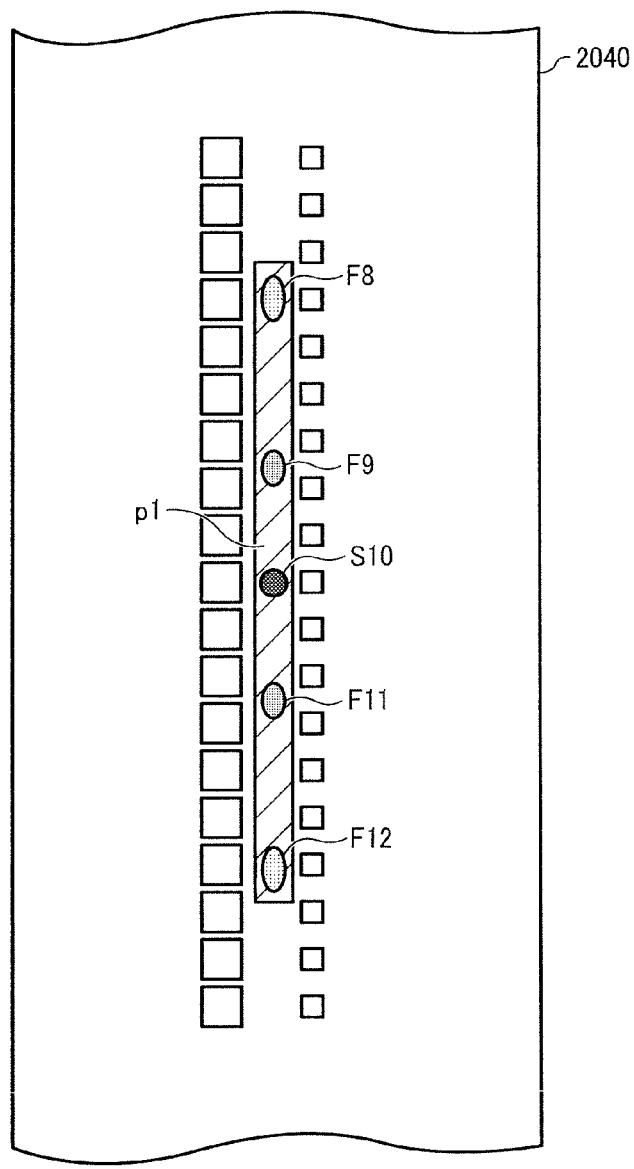
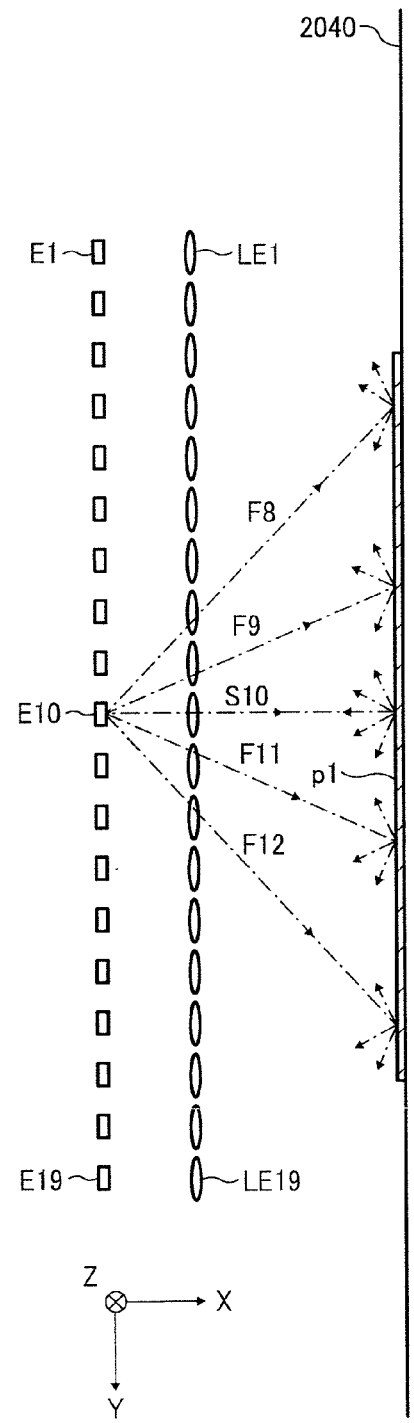

▨ : SPECULARLY REFLECTED LIGHT + DIFFUSELY REFLECTED LIGHT
▫ : SPECULARLY REFLECTED LIGHT
▨ : DIFFUSELY REFLECTED LIGHT

FIG. 85
FIG. 86
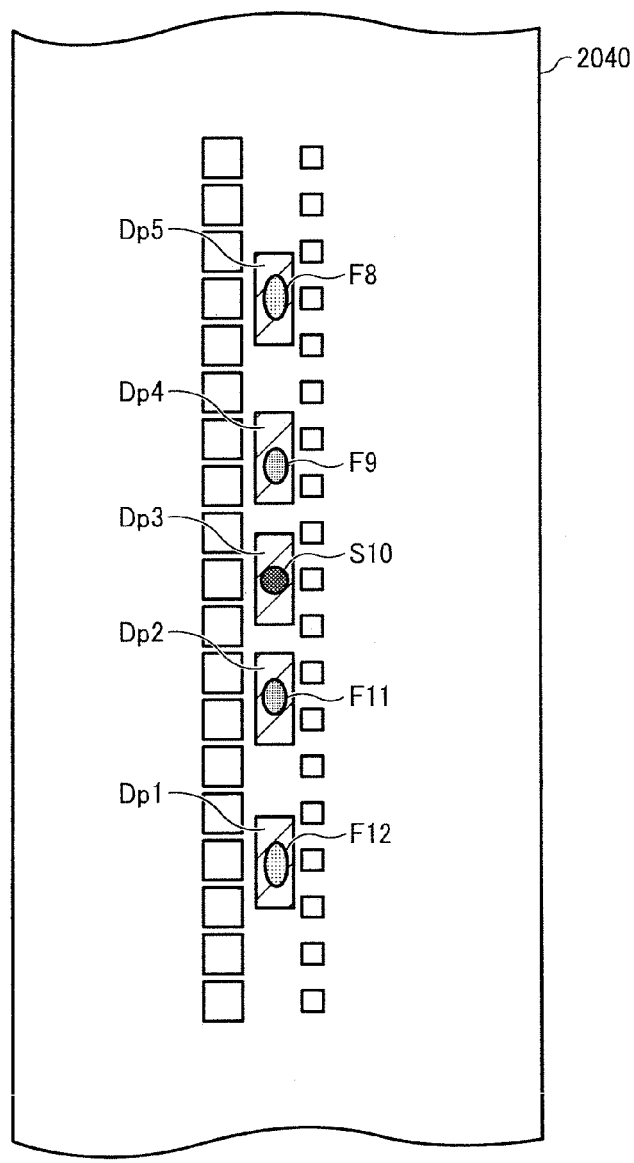
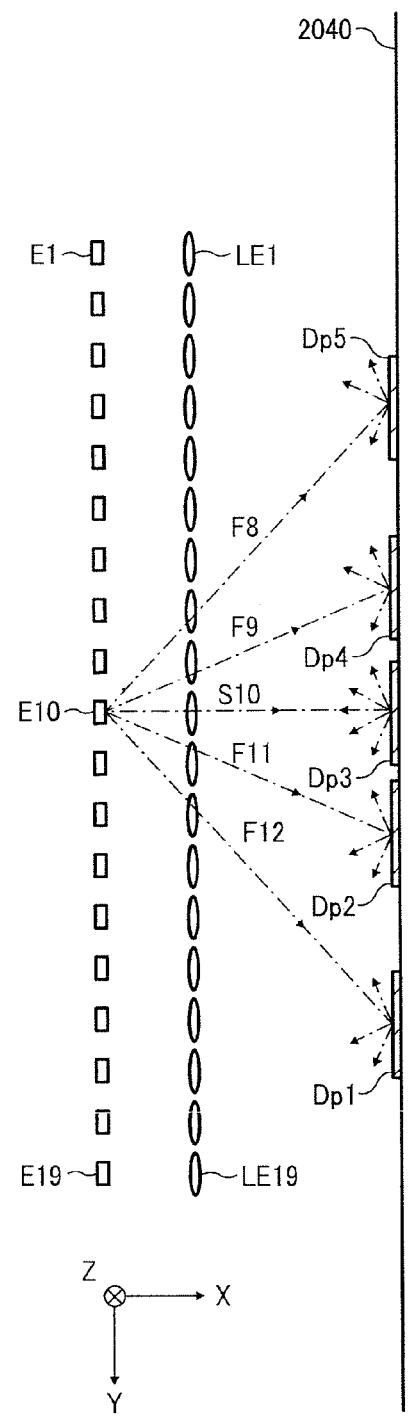

FIG. 87
FIG. 88
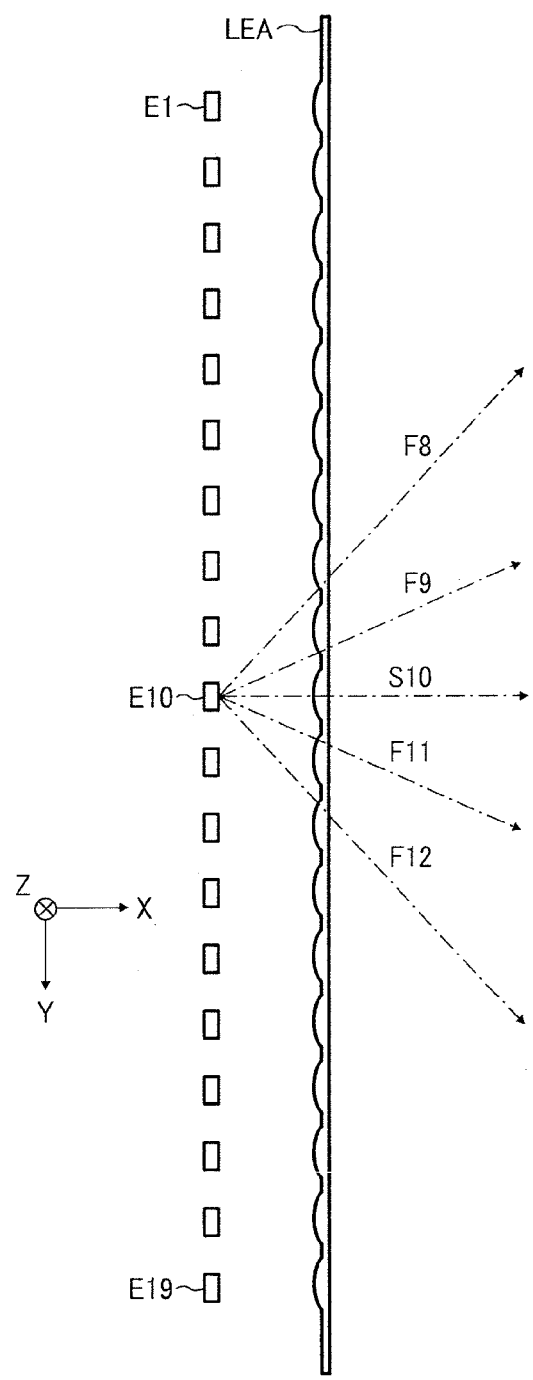
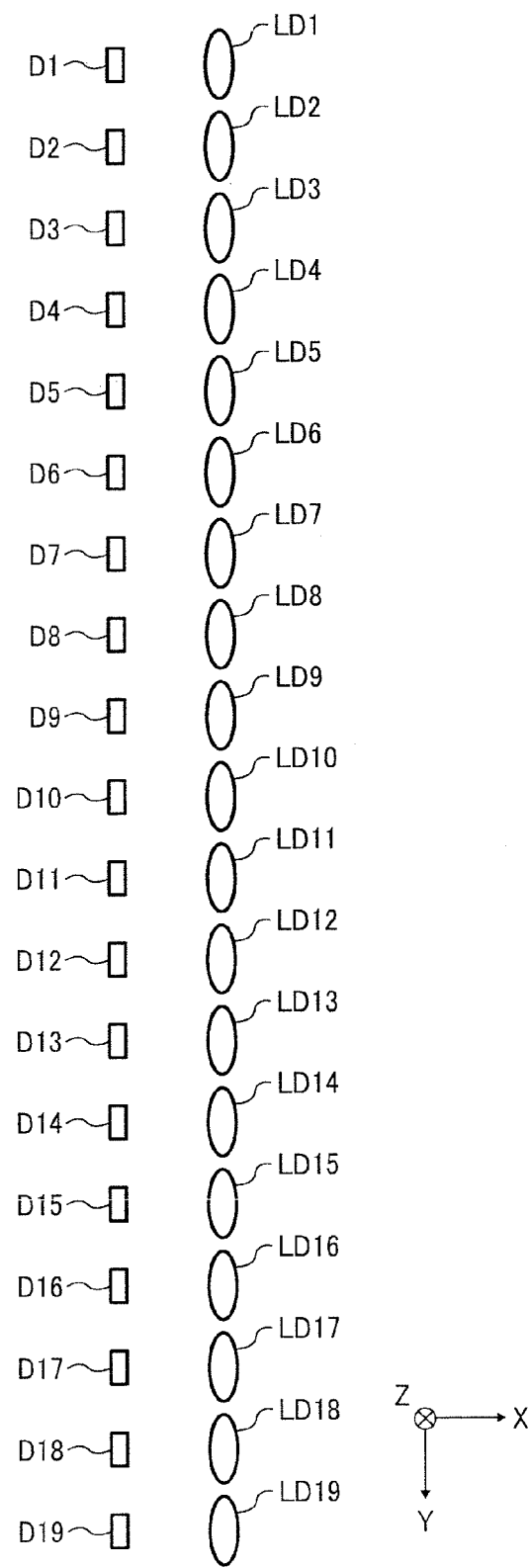

TONER-DENSITY CALCULATING METHOD, REFLECTIVE OPTICAL SENSOR, AND IMAGE FORMING APPARATUS

CROSS-REFERENCE TO RELATED APPLICATIONS

This is a continuation of U.S. patent application Ser. No. 12/763,695, filed Apr. 20, 2010, now U.S. Pat. No. 8,396,385 The entire disclosure of U.S. patent application Ser. No. 12/763,695 is incorporated herein by reference. Moreover, the present application claims priority to and incorporates by reference the entire contents of Japanese Patent Application No. 2009-101691 filed in Japan on Apr. 20, 2009 and Japanese Patent Application No. 2009-213665 filed in Japan on Sep. 15, 2009. The present application incorporates by reference the entire contents of Japanese Patent Application No. 2008-238487 filed in Japan on Sep. 17, 2008.

BACKGROUND OF THE INVENTION

1. Field of the Invention

The present invention relates to a toner-density calculating method, a reflective optical sensor that is used in the toner-density calculating method, and an image forming apparatus. The image forming apparatus is provided, for example, in a multifunction product (MFP) that includes the reflective optical sensor and works as at least one of a copier, a printer, a facsimile machine, and a plotter.

2. Description of the Related Art

A variety of image forming apparatuses use toner to form images, i.e., they form toner images. Example of such image forming apparatuses are analog image forming apparatuses, digital image forming apparatuses, black-and-white copiers, color copiers, printers, plotters, facsimile machines, and, multifunction printers (MFPs).

To form a good quality toner image, as is widely known, an electrostatic latent image needs to be developed with just an appropriate amount of toner. The electrostatic latent image can be developed with a two-component developer that contains toner and carrier or a single-component developer that contains only toner. An amount of the toner to be supplied to a developing unit that develops the electrostatic latent image is called, hereinafter, "toner density".

If the toner density is low, i.e., if the amount of the toner supplied to the electrostatic latent image is less than the necessary amount, a paler toner image will be formed. If the toner density is high, i.e., if the amount of the toner supplied to the electrostatic latent image is more than the necessary amount, a darker and difficult-to-see toner image will be formed. To form a good quality toner image, the toner density should be within an appropriate range.

To adjust the toner density to a value within the appropriate range, it is necessary to calculate the current toner density. In a typical method, the toner density is calculated from a change in a detection light reflected by a toner image that is formed dedicated to the toner-density calculation (hereinafter, "toner pattern"). An optical device that emits the detection light to the toner pattern and receives the detection light reflected by the toner pattern is called a reflective optical sensor.

Various types of reflective optical sensors are known in the art (see Japanese Patent Application Laid-open No. 2008-064953, Japanese Patent Application Laid-open No. S64-35466, Japanese Patent Application Laid-open No. 2004-21164, Japanese Patent Application Laid-open No. 2002-72612, Japanese Patent Application Laid-open No. 2004-309292, and Japanese Patent Application Laid-open No. 2004-309293).

Typical reflective optical sensors include a light-emitting unit and a light-receiving unit. The light emitting unit includes one, two, or three light-emitting elements having different wavelength characteristics. The light-receiving unit includes one or two light-receiving elements (e.g., photodiodes (PDs) or phototransistors).

Light-emitting diodes (LEDs) are typically used as the light-emitting elements. The LEDs emit the detection light of a spot size that is smaller than the toner pattern on the toner pattern.

The toner pattern is formed, for example, on a transfer belt. The toner pattern moves as the transfer belt rotates. A direction in which the transfer belt moves due to the rotation is called "sub-direction", and a direction perpendicular to the sub-direction on the transfer belt is called "main-direction". In a system in which electrostatic latent images are formed through optical scanning, the main-direction corresponds to the main-scanning direction, and the sub-direction corresponds to the sub-scanning direction.

An electrostatic latent image corresponding to a toner pattern is formed on a photosensitive member by optically scanning a surface of the photosensitive member with an electrostatic-latent-image forming unit, and the electrostatic latent image on the surface of the photosensitive member is then developed into the toner pattern. The toner pattern on the photosensitive member is then transferred onto the transfer belt, and is moved in the sub-direction with the rotation of the transfer belt. When the toner pattern enters a detection area, the toner pattern is exposed with a spot of the detection light from the reflective optical sensor.

The spot size of the spot of the detection light is typically about 2 millimeters (mm) to 3 mm.

In an ideal situation, the spot falls on the center of the toner pattern in the main-direction. However, it is difficult to always keep a relative position between the toner pattern and the reflective optical sensor in the main-direction the ideal state, due to various reasons. These reasons include fluctuation in an optical scanning area of the electrostatic-latent-image forming unit, the transfer belt meandering, which is positional shift of the reflective optical sensor in the main-direction from an initial installation position because of degradation while time passes.

If a portion of the spot falls in a region where there is no toner pattern because of the positional mismatch in the main-direction between the toner pattern and the reflective optical sensor, the reflected light received by the light-receiving unit represents wrong data, and therefore the calculated toner density is wrong. Assume, for example, that one light-emitting element emits one spot of the detection light, one light-receiving element receives the reflected light, and the toner density is calculated from a difference between specularly reflected light and diffusely reflected light. The light-receiving element is arranged to receive the specularly reflected light. If a first portion of the spot falls in a region where there is no toner pattern and a second portion falls on the toner pattern, the first portion of the detection light is reflected specularly while the second portion is reflected diffusely. As a result, in a configuration where the light-receiving element is arranged so as to receive the specularly reflected light, as compared to a case where the entire spot falls out of the toner pattern, intensity of the specularly reflected light that is received at the light-receiving element decreases due to the generation of the diffusely reflected light. The decrease in the intensity of the specularly reflected light can also occur when the toner amount at the toner pattern is low. Therefore, whether the decrease in the intensity of the specularly reflected light is due to low toner amount or mismatch between the spot and the toner pattern is always unclear.

To solve this problem, in the conventional techniques, the toner pattern of a size from about 15 mm to about 25 mm in both the main-direction and the sub-direction is formed so that the spot of the detection light cannot fall out of the toner pattern even in case of the positional mismatch.

In the image forming apparatuses, specifically, in the color image forming apparatus, the detection of the toner density by the reflective optical sensor using the toner pattern is performed to acquire so as to maintain high image quality as a maintenance activity necessary for an accurate image-forming process. Because the toner-density calculation is performed as the maintenance activity separated from the main activity, i.e., an image-forming process, the image forming operation cannot be performed during the toner-density calculation.

When the electrostatic latent image to be developed as the toner pattern is written by the optical scanning, a time period required for the optical scanning becomes longer as the size of the toner pattern become larger. In other words, the larger the toner pattern is, the lower the operating efficiency of the image formation becomes.

Moreover, because a total amount of the toner in the toner container or the like is fixed, as an amount of the toner to be used for the toner pattern increases, an amount of the toner to be used for the main activity also increases, i.e., the image formation decreases disadvantageously. The larger the toner pattern is, the more the toner amount is consumed for the toner pattern. In this manner, the conventional toner-density measuring methods have the two disadvantages, i.e., the low operating efficiency and the much toner-consumption amount for the toner pattern.

An array-type reflective optical sensor that solves the above problems is disclosed in Japanese Patent Application Laid-open No. 2008-070198 by the applicant of the present application.

The reflective optical sensor includes a light-emitting unit and a light-receiving unit. The light-emitting unit includes M number of light-emitting elements (M≥3) that each emits detection light to a supporting member. The light-emitting elements are aligned in a single direction intersecting with the sub-direction in such a manner that M number of spots of detection light fall on the supporting member and the distance between adjacent spots in the direction perpendicular to the sub-direction is less than or equal to the length of the toner pattern. The light-receiving unit includes N number of (N≥3) light-receiving elements. The light-receiving elements are aligned in a single direction on a plane opposed to the supporting member at positions corresponding to the light-emitting unit so as to receive the detection light reflected by the supporting member and/or the toner pattern.

The toner density is calculated on the basis of outputs from N number of the light-receiving elements that receive light emitted from the M number of light-emitting elements.

The supporting member is, typically, a transfer belt with a specular surface; therefore, light reflected from the transfer belt is specularly reflected light. Light reflected from the toner pattern includes both specularly reflected light and diffusely reflected light.

In Japanese Patent Application Laid-open No. 2008-070198, an embodiment is disclosed in which, when an arbitrary light-emitting element turns ON, the detection light reflected by the transfer belt (specularly reflected light) is received only at the light-receiving element corresponding to the on-state light-emitting element.

This means that, when an arbitrary light-emitting element turns ON and the detection light strikes the toner pattern, although the detection light is specularly and diffusely reflected by the toner pattern, specularly reflected light is received at only the light-receiving element corresponding to the on-state light-emitting element. M−1 number of the other light-receiving elements receive the diffusely reflected light.

Therefore, if the toner density is calculated with the above-described configuration on the basis of the amount of specularly reflected light, only those outputs are needed that are from the light-receiving element corresponding to an arbitrary on-state light-emitting element observed when light is reflected by the transfer belt and when light is reflected by the toner pattern. If the toner density is calculated on the basis of the amount of diffusely reflected light, in contrast, only those outputs are needed that are from the M−1 number of the light-receiving elements other than the light-receiving element corresponding to the on-state light-emitting element observed when light is reflected by the toner pattern.

However, the detection light reflected by the transfer belt (specularly reflected light) can be received not only by the light-receiving element corresponding to the on-state light-emitting element but also by some light-receiving elements near the corresponding light-receiving element (light-receiving elements not corresponding to the on-state light-emitting element).

Moreover, part of detection light that is specularly reflected by the toner pattern can be received not only by the light-receiving element corresponding to the on-state light-emitting element but also by some light-receiving elements not corresponding to the on-state light-emitting element.

If, in the above situation, only the output from the light-receiving element corresponding to the on-state light-emitting element is determined to be the output representing the light specularly reflected by the transfer belt and/or the toner pattern and the outputs from the light-receiving elements not corresponding to the on-state light-emitting element that are observed when the toner pattern is exposed to the light are determined to be the output representing the light diffusely reflected by the toner pattern, some of the outputs from the other light-receiving elements not corresponding to the on-state light-emitting element are partially not used in the toner-density calculation, which will lead to an inaccurate calculation result.

In other words, values of outputs (detection information) helpful to increase the sensitivity of the reflective optical sensor and the accuracy in the toner-density calculation are not properly used in the toner-density detection, resulting discarded uselessly.

SUMMARY OF THE INVENTION

It is an object of the present invention to at least partially solve the problems in the conventional technology.

According to an aspect of the present invention, there is provided a toner-density calculating method used in an image forming method for forming an image with toner, the toner-density calculating method including: forming a predetermined toner pattern on a supporting member that moves in a predetermined sub-direction; causing a light-emitting unit to illuminate the supporting member with detection light; receiving, at a light-receiving unit, the detection light reflected by the supporting member and/or the toner pattern; and calculating the toner density on a basis of difference between reflecting characteristics of the supporting member for the detection light and reflecting characteristics of the toner pattern for the detection light, wherein the light-emitting unit includes M number of light-emitting elements (M≥3) that emit the detection light, wherein the light-emitting elements are arranged in a direction intersecting with the sub-direction in such a manner that M number of spots of the detection light fall on the supporting member, and a distance between adjacent spots in a direction perpendicular to the sub-direction is less than or equal to a length of the toner pattern in the direction perpendicular to the sub-direction, the light-receiving unit includes N number of light-receiving elements (N≥3) that are arranged in a direction on a plane opposing to the supporting member, the light-receiving unit corresponding to the light-emitting unit so as to receive the detection light reflected by the supporting member and/or the toner pattern, an output from each of the N number of the light-receiving elements, obtained when the M number of the light-emitting elements emit the detection light, is separated into an amount of specularly reflected light and an amount of diffusely reflected light, and the toner density is calculated on a basis of the amount of specularly reflected light and the amount of diffusely reflected light.

According to another aspect of the present invention, there is provided a reflective optical sensor included in an image forming apparatus that forms an image with toner, in which a predetermined toner pattern is formed on a supporting member that moves in a predetermined sub-direction, a light-emitting unit illuminates the supporting member with detection light, a light-receiving unit receives the detection light reflected by the supporting member and/or the toner pattern, and the reflective optical sensor calculates the toner density on a basis of difference of reflecting characteristics of the supporting member reflecting the detection light and reflecting characteristics of the toner pattern reflecting the detection light, the reflective optical sensor including: the light-emitting unit that includes M number of light-emitting elements (M≥3) that are configured to turn ON and OFF individually or synchronously, the light-emitting elements being arranged in a direction; and the light-receiving unit that includes N number of light-receiving elements (N≥3) that are arranged in a direction at positions corresponding to the light-emitting unit, wherein an output from each of the N number of the light-receiving elements, obtained when the M number of the light-emitting elements emit the detection light, is separated into an amount of specularly reflected light and an amount of diffusely reflected light.

According to still another aspect of the present invention, there is provided an image forming apparatus that forms an image with toner, the image forming apparatus including: a reflective optical sensor, in which a predetermined toner pattern is formed on a supporting member that moves in a predetermined sub-direction, the reflective optical sensor including a light-emitting unit illuminates the supporting member with detection light, a light-receiving unit receives the detection light reflected by the supporting member and/or the toner pattern, and the reflective optical sensor calculates the toner density on a basis of difference of reflecting characteristics of the supporting member reflecting the detection light and reflecting characteristics of the toner pattern reflecting the detection light, the reflective optical sensor including: the light-emitting unit that includes M number of light-emitting elements (M≥3) that are configured to turn ON and OFF individually or synchronously, the light-emitting elements being arranged in a direction; and the light-receiving unit that includes N number of light-receiving elements (N≥3) that are arranged in a direction at positions corresponding to the light-emitting unit, wherein an output from each of the N number of the light-receiving elements, obtained when the M number of the light-emitting elements emit the detection light, is separated into an amount of specularly reflected light and an amount of diffusely reflected light.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 36 is a second schematic diagram illustrating the detection sensor;

FIG. 37 is a third schematic diagram illustrating the detection sensor;

FIG. 38 is a schematic diagram illustrating how rays of detection light illuminate;

FIG. 39 is a schematic diagram illustrating paths of a light ray emitted from a light-emitting element E10;

FIG. 40 is a schematic diagram illustrating how rays of detection light and flare light illuminate the transfer belt when the light-emitting element E10 turns ON;

FIG. 41 is a schematic diagram illustrating how light is reflected by the surface of the transfer belt when the light-emitting element E10 turns ON;

FIG. 44 is a schematic diagram that explains the relation between the light ray emitted from the light-emitting element E10 and the toner pattern, in which the toner pattern is formed at a specific position with a size appropriate to be exposed to no light other than the detection light S10;

FIG. 45 is a schematic diagram that explains how light is reflected in the situation shown in FIG. 44;

FIG. 48 is a schematic diagram that explains the relation between the light ray emitted from the light-emitting element E10 and the toner pattern, in which the toner pattern is formed at a specific position with a size appropriate to be exposed to the detection light S10 and the flare light F9;

FIG. 49 is a schematic diagram that explains how light is reflected in the situation shown in FIG. 48;

FIG. 53 is a schematic diagram that explains the relation between the light ray emitted from the light-emitting element E10 and the toner pattern shown in FIG. 52;

FIG. 54 is a schematic diagram that explains how light is reflected in the situation shown in FIG. 53;

FIG. 55 is a schematic diagram that explains the relation between the light ray emitted from the light-emitting element E10 and the toner pattern, in which the toner pattern is formed at a specific position with a size appropriate to be exposed to the detection light S10 and the flare light F11;

FIG. 56 is a schematic diagram that explains how light is reflected in the situation shown in FIG. 55;

FIG. 58 is a schematic diagram of a toner pattern that is a modification of FIG. 55;

FIG. 59 is a schematic diagram that explains how light is reflected in the situation shown in FIG. 58;

FIG. 60 is a schematic diagram that explains the relation between the light ray emitted from the light-emitting element E10 and the toner pattern, in which the toner pattern is formed at a specific position with a size appropriate to be exposed to the detection light S10 and the two rays of flare light (F8 and F9);

FIG. 61 is a schematic diagram that explains how light is reflected in the situation shown in FIG. 60;

FIG. 65 is a schematic diagram that explains the relation between the light ray emitted from the light-emitting element E10 and the toner pattern shown in FIG. 64;

FIG. 66 is a schematic diagram that explains how light is reflected in the situation shown in FIG. 65;

FIG. 67 is a schematic diagram that explains the relation between the light ray emitted from the light-emitting element E10 and the toner pattern, in which the toner pattern is formed at a specific position with a size appropriate to be exposed to the detection light S10 and the two rays of flare light (F11 and F12);

FIG. 68 is a schematic diagram that explains how light is reflected in the situation shown in FIG. 67;

FIG. 71 is a schematic diagram that explains the relation between the light ray emitted from the light-emitting element 510 and the toner pattern shown in FIG. 70;

FIG. 72 is a schematic diagram that explains how light is reflected in the situation shown in FIG. 71;

FIG. 73 is a schematic diagram that explains the relation between the light ray emitted from the light-emitting element 510 and the toner pattern, in which the toner pattern is formed at a specific position with a size appropriate to be exposed to the detection light S10 and the two rays of flare light (F9 and F11);

FIG. 74 is a schematic diagram that explains how light is reflected in the situation shown in FIG. 73;

FIG. 78 is a schematic diagram that explains the relation between the light ray emitted from the light-emitting element E10 and the toner pattern shown in FIG. 77;

FIG. 79 is a schematic diagram that explains how light is reflected in the situation shown in FIG. 78;

FIG. 80 is a schematic diagram that explains the relation between the light ray emitted from the light-emitting element E10 and the toner pattern, in which the toner pattern is formed at a specific position with a size appropriate to be exposed to the detection light S10 and the four rays of flare light (F8, F9, F11, and F12);

FIG. 81 is a schematic diagram that explains how light is reflected in the situation shown in FIG. 80;

FIG. 85 is a schematic diagram that explains the relation between the light ray emitted from the light-emitting element E10 and the toner pattern shown in FIG. 84;

FIG. 86 is a schematic diagram that explains how light is reflected in the situation shown in FIG. 84;

FIG. 87 is a schematic diagram of a system that includes nineteen detection-light collecting lenses as an integrated unit;

FIG. 88 is a first schematic diagram of a modified light-emitting system;

DETAILED DESCRIPTION OF THE PREFERRED EMBODIMENTS

Figure 1:
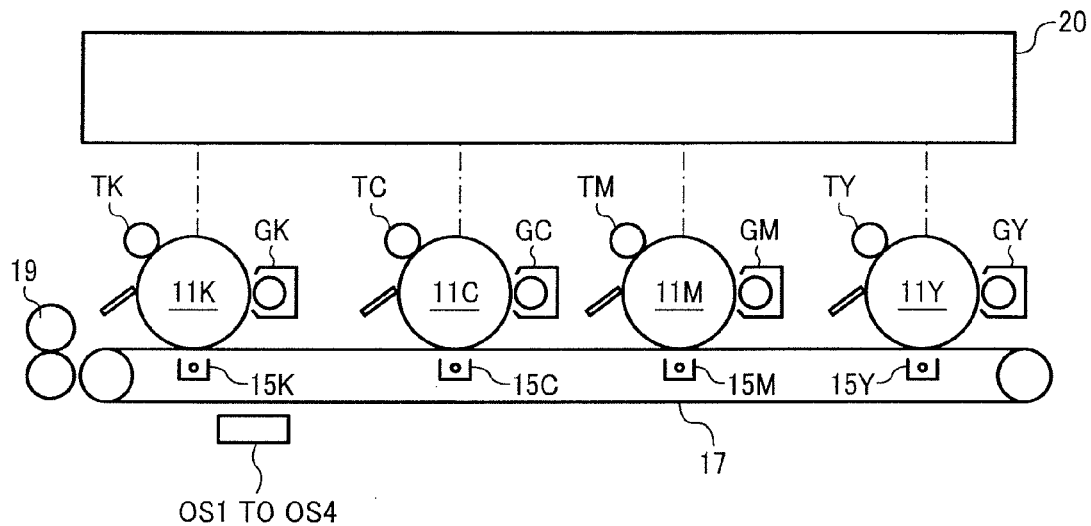
FIG. 1 is a schematic diagram of an image forming apparatus according to an example of a first embodiment.

Exemplary embodiments of the present invention are described in detail below.

A density calculating method according to the present embodiment involves, in a method of forming images with toner, forming a predetermined toner pattern on a supporting member moving in a predetermined sub-direction, causing a light-emitting unit to illuminate the supporting member with detection light, receiving the light reflected by the supporting member and/or the toner pattern at a light-receiving unit, and calculating the toner density using difference between characteristics of the supporting member reflecting the detection light and characteristics of the toner pattern reflecting the detection light.

The method of forming images with toner is used in the copiers, the printers, the plotters, the facsimile machines, the MFPs, etc. The method of forming images with toner includes the process of forming the electrostatic latent image and the process of developing the electrostatic latent image to the toner image. The process of forming the electrostatic latent image is, more particularly, the process of exposing a photoconductive latent-image carrier with an evenly-charged surface to a light by the optical scanner or the like.

The toner pattern is a toner image for the toner-density calculation. The toner pattern is formed by developing a predetermined electrostatic latent image. The toner pattern is on a supporting member in the calculation. In other words, the toner pattern is formed on the supporting member and then is moved in the sub-direction to the detection area.

The electrostatic latent image to be developed into the toner pattern can be formed by exposure of an image with a pattern having a predetermined density or by writing by the optical scanning.

As described above, the supporting member moves in the sub-direction while the toner-density is being detected, carrying the toner pattern thereon. The supporting member can be, for example, a latent-image carrier on which the electrostatic latent image is formed, a transfer belt, or an intermediate transfer belt that is used to transfer the toner image.

In the following description, "predetermined toner pattern" means that a shape of the toner pattern is fixed.

Features of a toner-density calculating method according to the present invention are described below.

A light-emitting unit includes M number of light-emitting elements (M≥3) each illuminates a supporting member with detection light. The light-emitting elements are aligned in a single direction intersecting with the sub-direction in such a manner that M number of spots of the detection light fall on the supporting member and the distance between adjacent spots in the direction perpendicular to the sub-direction is less than or equal to the length of the toner pattern. A light-receiving unit includes N number of light-receiving elements (N≥3). The light-receiving elements are aligned in a single direction on a plane opposed to the supporting member at positions corresponding to the light-receiving elements so as to receive the detection light reflected by the supporting member and/or the toner pattern.

The toner density is calculated on the basis of outputs from N number of the light-receiving elements that are observed when M number of the light-emitting elements emit light.

The output from each of N number of the light-receiving element of the light-receiving unit is separated into the amount of specularly reflected light and the amount of diffusely reflected light, so that the toner density is calculated on the basis of the amount of specularly reflected light and the amount of diffusely reflected light.

In the above description, "single direction intersecting with the sub-direction" includes the direction perpendicular to the sub-direction, i.e., the main-direction. "Distance between adjacent spots in a direction perpendicular to the sub-direction" means a distance between adjacent ones of spots formed on the surface of the supporting member aligned in the single direction perpendicular to the sub-direction, i.e., the main-direction when each of M number of the light-emitting elements emits the detection light. Moreover, "distance between adjacent spots" means not a distance between the centers of the adjacent spots in the main-direction but, if the adjacent spots are not overlapped with each other, the distance between the circumferences of the adjacent spots in the main-direction.

Specifically, it is assumed in the following description that M number of the light-emitting elements are aligned in the main-direction at a 3-mm pitch, and the diameter of the circular spots is 2 mm. In other words, the distance between adjacent spots is 1 mm in the main-direction. This 1-mm interval between the adjacent spots is not exposed to the detection light.

However, if the toner pattern is larger than the distance between the adjacent spots (1 mm) in the main-direction, at least a part of the toner pattern is exposed to any of the spots when the toner pattern passes through an area on which the spots are aligned. Therefore, it is enough for the toner pattern to be a little larger than 1 mm in the main-direction to be exposed to the spots of the detection light. In other words, a toner pattern that is much smaller than the conventional toner pattern (15 mm to 25 mm) in width in the main-direction is sufficient.

The distance between the adjacent spots in the direction perpendicular to the sub-direction should be set smaller than the width of the toner pattern in the main-direction. That is, the distance between the adjacent spots can be smaller than 1 mm, and, moreover, the adjacent spots can have an overlap in the main-direction. If the adjacent spots are overlapped, the distance between adjacent spots is a minus value, and the areas that are exposed to the spots of the detection light make a single area continuous in the main-direction. Therefore, the width of the toner pattern in the main-direction can be decreased infinitely, in principle.

Moreover, even if the spot size is smaller than the width of the toner pattern in the main-direction, it is possible to expose without fail the toner pattern to the detection light by adjusting the pitch between the adjacent spots in the main-direction to a value smaller than the width of the toner pattern in the main-direction. This is because, by the adjustment, the distance between the adjacent spots in the main-direction becomes smaller than the width of the toner pattern in the main-direction.

When the light-emitting unit emits the detection light to the supporting member, the detection light is reflected by the surface of the supporting member and/or the toner pattern, and is received by the light-receiving unit. The light-receiving unit includes three or more light-receiving elements. The intensity of the light received at each of the light-receiving elements varies depending on a positional relation between the spots of the detection lights and the toner pattern.

The toner density is calculated using outputs from the three or more light-receiving elements.

As is widely known, when the detection light strikes the toner pattern, the detection light is diffusely reflected. On the other hand, if the surface of the supporting member is specular and when the detection light strikes an area out of the toner pattern on a surface of the supporting member, the detection light is specularly reflected. The supporting member can be, for example, a photoconductive latent-image carrier. Accordingly, the reflection property when the detection light strikes the area out of the toner pattern on the surface of the supporting member shows the specular reflection, while the reflection property when the detection light strikes the toner pattern shows the diffuse reflection. The difference in the reflection properties causes a variation of the intensities of the light received at the three or more light-receiving elements. Therefore, a degree of the toner darkness (i.e., the toner density) can be calculated using outputs from the three or more light-receiving elements.

If a transfer belt or an intermediate transfer belt is used as the supporting member, the surface of the supporting member reflects, in some cases, the detection light substantially specularly almost as a mirror surface reflects, and reflects, in other cases, the detection light diffusely. Even in a case that the surface of the supporting member reflects the detection light diffusely, if there is a difference between the diffuse reflection from the area out of the toner pattern and the diffuse reflection from the toner pattern, a distribution of the intensities of the light received at the plural light-receiving elements when the detection light is diffusely reflected by the area out of the toner pattern differs from the distribution when the detection light is diffusely reflected by the toner pattern. Therefore, the toner density can be calculated correctly.

In the following description, it is assumed that both M, which is the number of the light-emitting elements that form the light-emitting unit, and N, which is the number of the light-receiving elements that form the light-emitting unit, are equal to or larger than three. It is allowable to set M equal to N (M=N) or different from N (M≠N).

Three or more LEDs aligned in a single direction can be used as the light-emitting elements of the light-emitting unit. If the LEDs have a lens function of collecting divergent light, the LEDs are arranged in such a manner that the detection light forms the spot with a desired size on the supporting member.

Alternatively, an LED array including three or more light-emitting elements can be used as the light-emitting unit. In this case, a light-collection optical system can be included in the light-emitting unit to collect the light emitted from the LED array.

PDs can be used as the light-receiving elements of the light-receiving unit. Alternatively, a PD array including three or more PDs (e.g., charge-coupled device (CCD) line sensor) can be used as the light-receiving unit.

The lower limit of M or N is, as described above, three. The upper limit of M or N is set appropriately based on the practical size of the reflective optical sensor (reflective optical element) for the toner-density calculation. The upper limit of M is, preferably, about 500. The upper limit of N can be several thousands as large as the number of PDs in the above-described PD array.

The light-emitting elements in total of M can be tuned ON/OFF in various manners. For example, all the light-emitting elements turn ON/OFF, simultaneously. Alternatively, M number of the light-emitting elements is separated into some groups. The light-emitting elements of each group turn ON/OFF in sequence beginning with the light-emitting element on its separation point. Still alternatively, the light-emitting elements turn ON/OFF, sequentially one after another.

The present embodiment is described in detail below. An image forming apparatus according to a first embodiment is described with reference to FIG. 1. The image forming apparatus shown in FIG. 1 is an image forming apparatus that forms "color images". A color image is formed with four toners including yellow (Y), magenta (M), cyan (C), and black (K).

The reference numeral 20 shown in FIG. 1 is an "optical scanning device". The optical scanning device 20 can be any widely-known scanner. The reference numerals 11Y, 11M, 11C, and 11K are drum-shaped photosensitive elements. Each of the photosensitive elements 11Y, 11M, 11C, and 11K corresponds to "photoconductive latent-image carriers". The photosensitive element 11Y is used for forming a yellow toner image, the photosensitive element 11M is for a magenta toner image, the photosensitive element 11C is for a cyan toner image, and the photosensitive element 11K is for a black toner image.

The optical scanning device 20 writes images onto the photosensitive elements 11Y, 11M, 11C, and 11K by the optical scanning. The photosensitive elements 11Y, 11M, 11C, and 11K are rotated in a clockwise direction at a constant speed, charged evenly by charging rollers TY, TM, TC, and TK as charging units, and scanned by the optical scanning device 20. Thus, electrostatic latent images (negative latent images) for yellow, magenta, cyan, and black are written onto the photosensitive elements 11Y, 11M, 11C, and 11K, respectively.

Those electrostatic latent images are developed by developing devices GY, GM, GC, and GK, and thus the yellow toner image, the magenta toner image, the cyan toner image, and the black toner image are formed on the photosensitive elements 11Y, 11M, 11C, and 11K, respectively as positive images.

The toner images are transferred onto a recording sheet (not shown) (e.g., transfer paper and plastic sheet for overhead projector) via a transfer belt 17.

The recording sheet is conveyed from a sheet table (not shown) that is arranged under the transfer belt 17 to an upper-right circumference of the transfer belt 17 shown in FIG. 1. After that, the recording sheet is attached to the transfer belt 17 by the exertion of the electrostatic force, and is conveyed to the left side of FIG. 1 by counterclockwise rotation of the transfer belt 17. The recording sheet sequentially receives, while being conveyed, the yellow toner image from the photosensitive element 11Y by a transfer member 15Y, the magenta toner image from the photosensitive element 11M by a transfer member 15M, the cyan toner image from the photosensitive element 11C by a transfer member 15C, and the black toner image from the photosensitive element 11K by a transfer member 15K.

In this manner, a full-color image is formed on the recording sheet in a superimposed manner. After that, the full-color image is fixed onto the recording sheet by a fixing device 19. The recording sheet with the full-color image is discharged out of the image forming apparatus. The full-color image can be formed onto an intermediate transfer belt in the superimposed manner and then transferred from the intermediate transfer belt to the recording sheet, instead of directly being formed on the recording sheet.

The reference numerals OS1 to OS4 shown in FIG. 1 are reflective optical sensors. In the image forming apparatus, the images are written onto the photosensitive elements 11Y, 11M, 11C, and 11K by the optical scanning as described above. The main-scanning direction in the optical scanning is a direction perpendicular to the drawing of FIG. 1 called "main-direction". A method of calculating the toner density by using the reflective optical sensors OS1 to OS4 is described below.

The optical scanning device 20 writes a certain electrostatic latent image onto each of the photosensitive elements 11Y, 11M, 11C, and 11K; the developing devices GY, GM, GC, and GK develop the electrostatic latent images to the toner images; the toner images are transferred from the photosensitive elements 11Y, 11M, 11C, and 11K directly to the surface of the transfer belt 17. Thus, the toner pattern is formed.

It is clear from the above description that the transfer belt 17 corresponds to the supporting member. This is why, hereinafter, the transfer belt 17 is called "supporting member 17", appropriately. The toner pattern is formed on the transfer belt 17, the formed toner pattern is moved by the rotation of the transfer belt 17, and the toner-density calculation is performed using the reflective optical sensors OS1 to OS4.

The toner pattern is removed from the surface of the transfer belt 17 by a cleaning device (not shown) arranged right, i.e., downstream of the reflective optical sensors OS1 to OS4.

Figure 2:
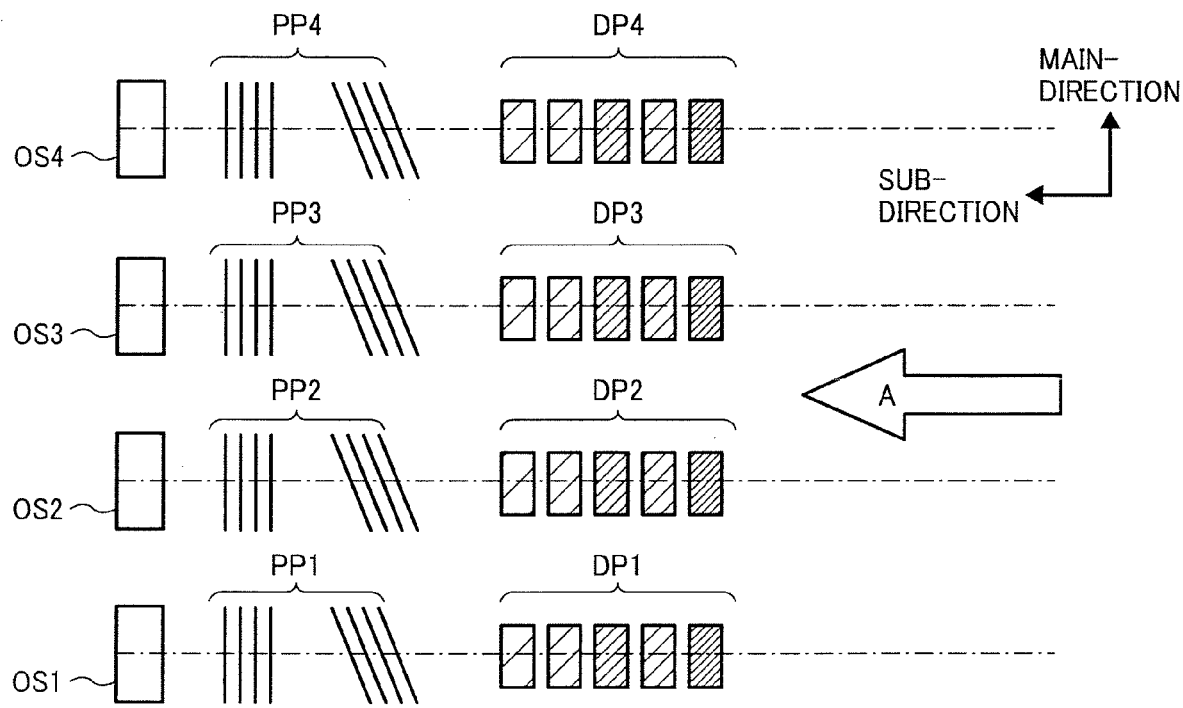
FIG. 2 is a schematic diagram that explains how a toner pattern is detected by a reflective optical sensor.

FIG. 2 is a schematic diagram that explains the relation among the toner pattern that is formed on the transfer belt 17, i.e., the supporting member, and the reflective optical sensors OS1 to OS4. The up-and-down direction of FIG. 2 corresponds to the main-direction, i.e., the direction perpendicular to the paper of FIG. 1. The direction from the right side to the left side of FIG. 2 (indicated by the arrow A shown in FIG. 2) corresponds to the sub-direction, i.e., the moving direction of the surface of the transfer belt 17.

The reference numerals PP1 to PP4 shown in FIG. 2 are position detecting patterns that are used to detect positions of the toner images in yellow to black, respectively. The reference numerals DP1 to DP4 are toner patterns that are used to calculate the toner density.

The toner pattern DP1 is used for calculation for the yellow toner density, the toner pattern DP2 is for the magenta toner density, the toner pattern DP3 is for the cyan toner density, and the toner pattern DP4 is for the black toner density.

In other words, the reflective optical sensors OS1 to OS4 detect positions of the toner images at four points aligned in the main-scanning direction. Moreover, the reflective optical sensor OS1 calculates the yellow toner density, the reflective optical sensor OS2 calculates the magenta toner density, the reflective optical sensor OS3 calculates the cyan toner density, and the reflective optical sensor OS4 calculates the black toner density.

In the example shown in FIG. 2 the toner patterns DP1 to DP4 are aligned in the main-direction; however, it is possible to align the toner patterns DP1 to DP4 in the sub-direction. In the later case, the reflective optical sensor OS1 sequentially calculates the various toner densities. It is allowable to stop operation of the reflective optical sensor OS4 and detect the position detecting patterns PP1 to PP3 at the three points aligned in the main-scanning direction by using the other three reflective optical sensors OS1 to OS3.

As shown in FIG. 2, the position detecting patterns PP1 to PP4 are formed on certain positions of the transfer belt 17 to be opposed to the reflective optical sensors OS1 to OS4, respectively. Each of the position detecting patterns PP1 to PP4 includes four pairs of line patterns. Each pair includes a parallel line parallel to the main-direction and a slant line incline not parallel to the main-direction. The four pairs are formed with the yellow toner, the magenta toner, the cyan toner, and the black toner.

Although the reflective optical sensor detects the toner pattern that is formed on the transfer belt 17 that is used to convey the recording sheet and transfer the toner image onto the recording sheet in the first embodiment, the reflective optical sensor can be configured to detect the toner pattern that is formed on the photosensitive element as the latent-image carrier or the intermediate transfer belt (or intermediate transfer medium).

The reflective optical sensors OS1 to OS4 and the detection for the toner pattern are described below.

Figure 3A:
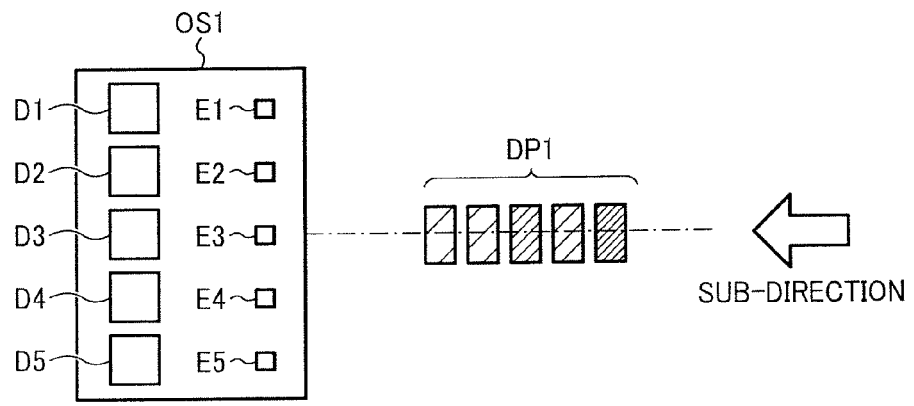
FIGS. 3A to 3F are schematic diagrams that explain how the toner pattern is detected by the reflective optical sensor.

FIG. 3A is a schematic diagram of the reflective optical sensor OS1. The four reflective optical sensors OS1 to OS4 have the same structure, and therefore only the reflective optical sensor OS1 is described.

The up-and-down direction in FIG. 3A corresponds to the "main-direction"; the side-to-side direction corresponds to the "sub-direction". The reflective optical sensor OS1 includes a light-emitting unit and a light-receiving unit. The light-emitting unit and the light-receiving unit are accommodated in a housing as a unit. The light-emitting unit includes M number of light-emitting elements E1 to E5 (M=5) that emit detection light. The light-emitting elements E1 to E5 are aligned parallel to the main-direction at an equal pitch. The light-receiving unit includes N number of light-receiving elements D1 to D5 (N=5) that receive reflected light. The light-receiving elements D1 to D5 are also aligned parallel to the main-scanning direction at an equal pitch, corresponding to the light-emitting elements E1 to E5. The reflective optical sensor OS1 is arranged at the lower position on the transfer belt 17 as shown in FIG. 1.

The light-emitting elements E1 to E5 together forming the light-emitting unit are aligned, with respect to the main-direction, to the light-receiving elements D1 to D5 together forming the light-receiving unit, respectively. It means that the pitch of the light-receiving elements D1 to D5 is equal to the pitch of the light-emitting elements E1 to E5.

It is assumed that the surface of the transfer belt 17 is specular. When the detection light is emitted from each light-emitting element, light specularly reflected by the surface of the transfer belt is received at three light-receiving elements, which are the corresponding light-receiving element and two light-receiving elements adjacent to the corresponding light-receiving element. In the example shown in FIG. 3B, when the light-receiving element E3 turns ON and the detection light coming from the light-emitting element E3 is reflected by the surface of the transfer belt, the specularly reflected light is received at the light-receiving element D3 which is the one corresponding to the light-emitting element E3, and the light-receiving elements D2 and D4 which are adjacent to the light-receiving element D3, while no light specularly reflected is received at the light-receiving elements D1 and D5. As a result, the output from each of the three light-receiving elements D2, D3, and D4 is larger than zero, while the output from each of the two light-receiving elements D1 and D5 is zero.

The light-emitting elements E1 to E5 are, for example, LEDs. The light-receiving elements D1 to D5 are, for example, PDs.

The pitch of the light-emitting elements E1 to E5 is set to such a value that, when the light-emitting elements E1 to E5 emit the detection light and five spots of the detection light are formed on the surface of the transfer belt 17 aligned in the main-scanning direction, a distance between adjacent ones of the spots is smaller than a width of the toner pattern DP1 in the main-direction.

As described above, the toner pattern DP1 shown in FIG. 3A is formed with the yellow toner. The toner pattern DP1 includes various rectangular toner patterns (five patterns in FIG. 2) having different gradated densities. In other words, the toner pattern DP1 is a collection of the five rectangular having different toner densities. Those rectangular toner patterns having different toner densities are formed by adjusting a laser power in the optical scanning, a duty in the emission light, or a developing bias.

Figure 3B:
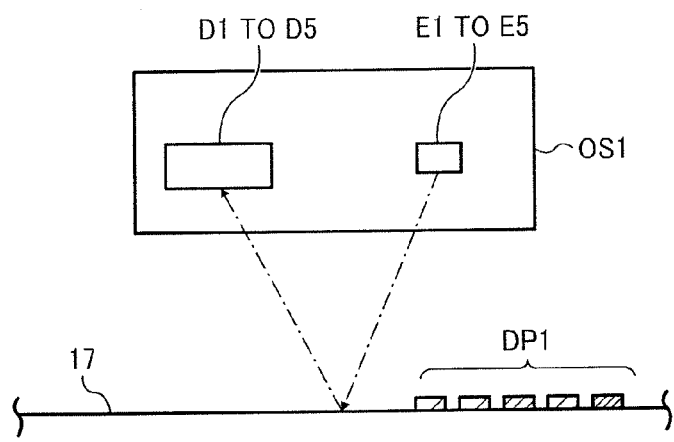

As shown in FIGS. 3A and 3B, the toner pattern DP1 is formed on the surface of the transfer belt 17 as the supporting member, and then moved in the sub-direction to the distance to detect of the reflective optical sensor OS1. Timing when the toner pattern DP1 is formed and time required for the toner pattern DP1 to move to the detection area are substantially fixed. When the toner pattern DP1 approaches to the distance to detect, the light-emitting elements E1 to E5 start ON/OFF. The detection of the position detecting pattern. PP1 is performed before the detection of the toner pattern DP1. The detection of the position detecting pattern PP1 will be described later.

The size of the spot, which are formed on the surface of the transfer belt 17 when the light-emitting elements E1 to E5 emit the detection light, is set to, for example, 2 mm smaller than the pitch of the light-emitting elements E1 to E5 of, for example, 3 mm. The five spots are aligned in contact with each other in the main-direction on the transfer belt 17.

The width of each of the rectangular toner patterns of the toner pattern DP1 in the main-direction is set to, for example, 2.5 mm smaller than the pitch of the light-emitting elements E1 to E5 of, for example, 3 mm. That is, the distance between the adjacent spots in the main-direction is 2 mm, which is smaller than the width of the rectangular toner pattern in the main-direction of 2.5 mm.

The light-emitting elements E1 to E5 turn ON/OFF, sequentially starting from the light-emitting element E1 to the light-emitting element E5. More particularly, the light-emitting element E1 turns ON and then OFF, firstly. The light-emitting element E2 turns ON and then OFF, secondly. After that, the light-emitting element E3 turns ON and then OFF, thirdly. Subsequently, the light-emitting element E4 and then the light-emitting element E5 turn ON/OFF, in the same manner. The ON/OFF operation of those light-emitting elements E1 to E5 is repeated at a high speed. Thus, the surface of the transfer belt 17 is scanned in the main-direction over and over with the five spots of the detection light. This operation is called, hereinafter, "spot scanning with the detection light".

As described above, the surface of the transfer belt 17 is specular. If the detection light strikes an area out of the toner pattern, the reflected light is specularly reflected light.

Figure 4:
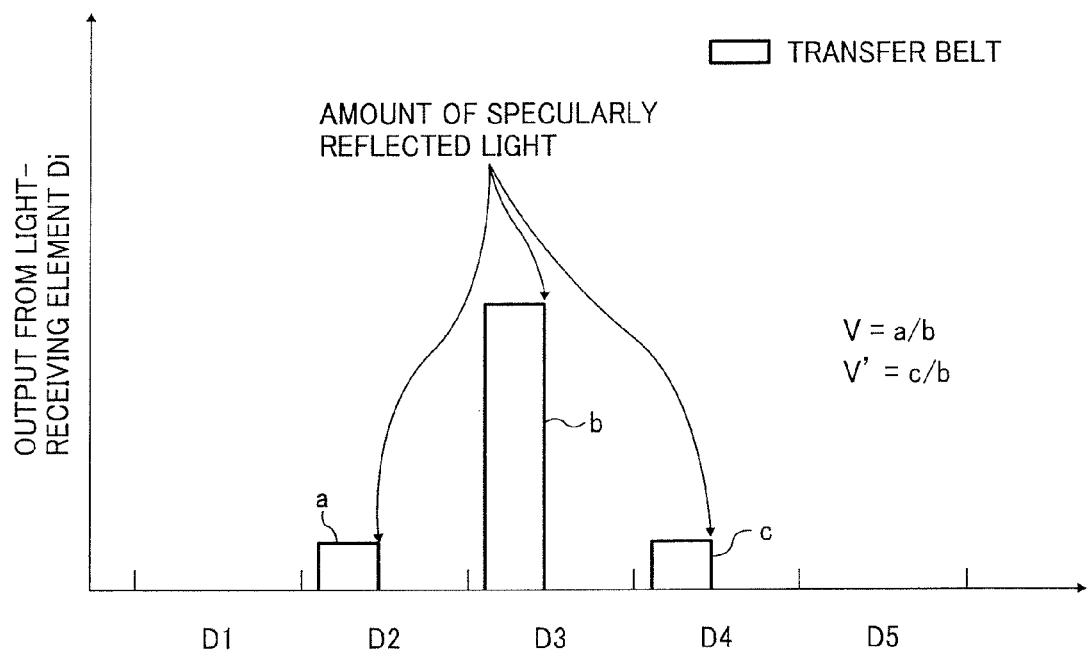
FIG. 4 is a graph of output due to light specularly reflected by a transfer belt, in which the graph is used to explain detection by the reflective optical sensor.

When the detection light is emitted from each light-emitting element, light specularly reflected by the surface of the transfer belt is received at only three light-receiving elements that include the corresponding light-receiving element and two light-receiving elements adjacent to the corresponding light-receiving element (light-receiving elements not corresponding to the on-state light-emitting element). This behavior is described with reference to FIG. 4. FIG. 4 is a graph of output from individual light-receiving elements due to the specularly reflected light that are observed when the light-emitting element E3 turns ON and the detection light from the light-emitting element E3 is reflected by the transfer belt 17. The horizontal axis is the light-receiving elements; the vertical axis is the magnitude of the output. It is clear from the graph that the outputs from the light-receiving elements D1 and D5 are zero.

Suppose, with this configuration, there is the case where the center of the toner pattern DP1 in the main-direction is on the spot of the detection light emitted from the light-emitting element E3. The detection light emitted from the light-emitting element E1 is specularly reflected by the surface of the transfer belt 17, and the specularly reflected light is received at the light-receiving elements D1 and D2. If the light-emitting element E1 turns ON/OFF solely, the output from the corresponding light-receiving element D1 is substantially equal to the output from the light-receiving element D3, while the output from the light-receiving element D2 is substantially equal to the output from the light-receiving element D4.

When the detection light is emitted from the light-emitting element E2, the detection light is specularly reflected by the surface of the transfer belt 17 and the specularly reflected light is received at the light-receiving elements D2 and D3. When the detection light is emitted from the light-emitting element E4, the detection light is specularly reflected by the surface of the transfer belt 17 and the specularly reflected light is received at the light-receiving elements D3, D4, and D5. When the detection light is emitted from the light-emitting element E5, the detection light is specularly reflected by the surface of the transfer belt 17, and the specularly reflected light is received at the light-receiving elements D4 and D5. If the light-emitting element E2 is ON solely, the output from the corresponding light-receiving element D2 is substantially equal to the output from the light-receiving element D3, while the output from the light-receiving element D1 is substantially equal to the output from the light-receiving element D2, and the output from the light-receiving element D3 is substantially equal to the output from the light-receiving element D4. If the light-emitting element E4 turns ON/OFF solely, the output from the corresponding light-receiving element D4 is substantially equal to the output from the light-receiving element D3, while the output from the light-receiving element D3 is substantially equal to the output from the light-receiving element D2, and the output from the light-receiving element D5 is substantially equal to the output from the light-receiving element D4.

If the light-emitting element E5 turns ON/OFF solely, the output from the corresponding light-receiving element D5 is substantially equal to the output from the light-receiving element D3, while the output from the light-receiving element D4 is substantially equal to the output from the light-receiving element D2.

Figure 3C:
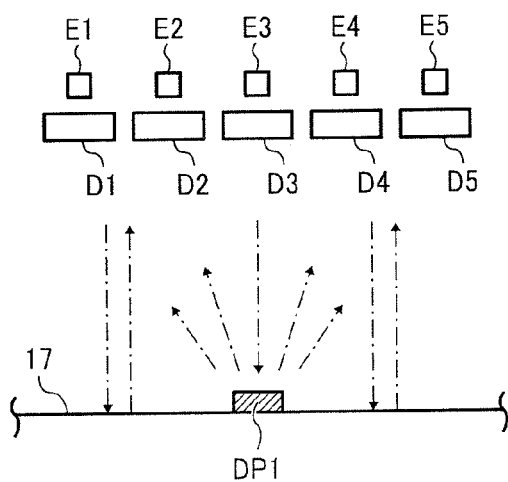

In contrast, when the light-emitting element E3 turns ON and the detection light strikes the toner pattern DP1 as shown in FIG. 3C, the detection light is specularly and diffusely reflected by the toner pattern DP1.

Figure 5:
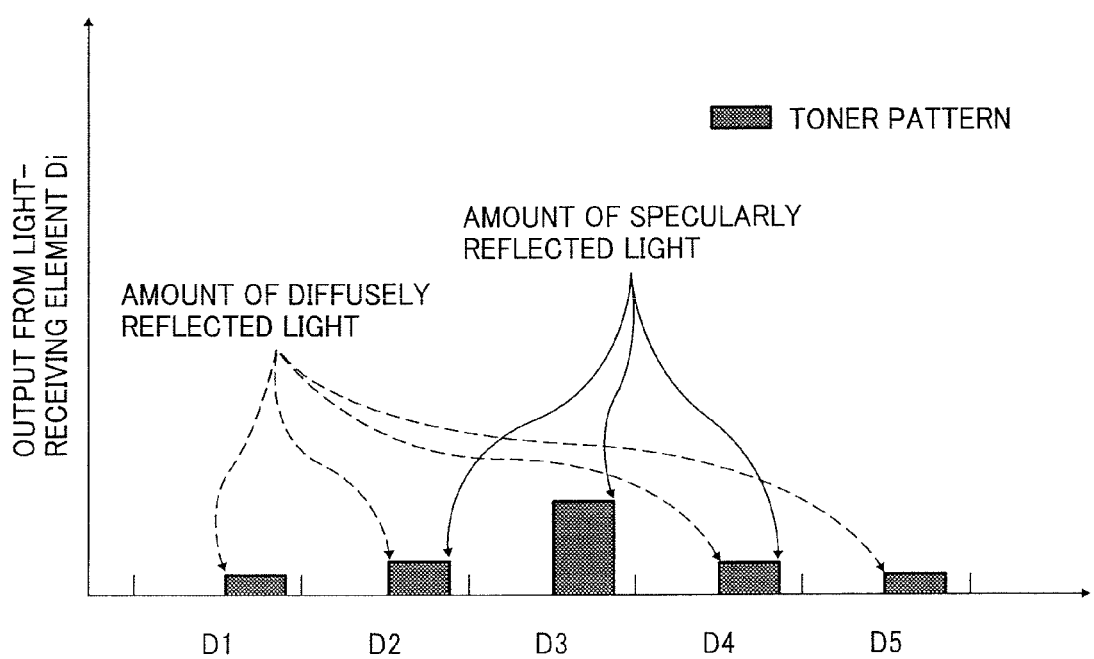
FIG. 5 is a graph of output due to light specularly reflected by the toner pattern and light diffusely reflected by the toner pattern, in which the graph is used to explain detection by the reflective optical sensor.

The distribution of the outputs from the individual light-receiving elements is shown in FIG. 5. The output from each of the light-receiving elements D1 and D5 is completely due to light diffusely reflected by the toner pattern. The output from the light-receiving element D3 is completely due to light specularly reflected by the toner pattern. The output from each of the light-receiving elements D2 and D4 is due to both light diffusely reflected by the toner pattern and light specularly reflected by the toner pattern.

When checking the outputs from the light-receiving elements D1 to D5 that are observed when the toner pattern DP1 on the transfer belt is exposed to the detection light, it is found that the amount of light received at the light-receiving element D3 decreases when compared with the case where the area out of the toner pattern on the surface of the transfer belt 17 is exposed to the detection light. It is also found that the outputs from the light-receiving element other than the light-receiving element D3 are larger than zero. This result suggests that the toner pattern DP1 (one of the rectangular toner patterns of the toner pattern DP1) is on the position to receive light coming from the light-emitting element E3. If the toner pattern is between the light-emitting elements E3 and E4, when the light-emitting element E3 turns ON, the output from the light-receiving element D3 is low, and when the light-emitting element E4 turns ON, the output from the light-receiving element D4 is low. This result suggests that the toner pattern is between the light-emitting elements E3 and E4 in the main-direction. If the output from the light-receiving element D3 is lower than the output from the light-receiving element D4, the toner pattern is closer to the light-emitting element E4.

In this manner, the position of the toner pattern DP1 in the main-direction can be detected accurately down to "the pitch of the light-emitting elements Ei (i=1 to 5)".

It means that, if, for example, 100 light-emitting elements E1 to EM (M=100) are aligned at a 100-μm pitch in the main-direction, the arrangement width is 10 mm. One hundred of light-receiving elements D1 to DN (N=100) are aligned in the main-direction at the 100-μm pitch. When the light-emitting element Ei (i=1 to 100) emits the detection light, the spot of the detection light with the diameter 80 μm is formed on the surface of the supporting member. The detection light is specularly reflected by the supporting member and then received at some light-receiving elements Dj (j=i−1, i, and i+1). Suppose, for example, there is the case where the length of the toner pattern in the main-direction is set equal to the pitch of the light-emitting elements, i.e., 100 μm and the light-emitting element Ei turns ON and OFF in sequence from the light-emitting elements E1 to E100. When checking change in the output from the light-receiving element Di (i=1 to 100), it is found that, when the light-emitting elements Ei and Ei+1 are ON, the outputs from the light-receiving elements Di and Di+1 are low, the toner pattern is determined to be "a position between the light-emitting elements Ei and Ei+1". It means that the main-directional position of the toner pattern with the width 100 μm in the sub-direction can be detected accurately by 100 μm each.

It is easy to implement the arrangement of 100 light-emitting elements at the 100-μm pitch, if an LED array is used. Moreover, it is easy to implement the arrangement of 100 light-receiving elements at the 100-μm pitch, if a PD array is used. Even several tens- to several hundreds-μm pitch LED and PD arrays are available.

The reflective optical sensor that is described with reference to FIGS. 3A to 3F can be fabricated by densely arranging individual LEDs as the light-emitting elements E1 to E5 and light-receiving elements D1 to D5 as individual PDs, for example, by resin-molding or surface-mounting on a substrate. If extremely small LEDs and PDs dimensions of which can be adjusted in the millimeter are used, the pitch can be decreased to about 1 mm. By using extremely small LEDs and PDs, the position of "the toner pattern with the length about 1 mm in the main-direction" can be detected accurately in millimeter order.

As described above, the toner pattern DP1 is used to calculate the yellow toner density. The toner pattern DP1 includes the five rectangular toner patterns having differently gradated densities aligned in the sub-direction at the predetermined pitch.

If, for example, the spot of the detection light emitted from the light-emitting element E3 strikes the toner pattern while the light-emitting elements E1 to E5 turn ON/OFF sequentially, the amount of the specularly reflected light received at the light-receiving element D3 decrease while the outputs of the other light-receiving elements increase by the amount of the diffusely reflected light. The amount of the specularly reflected light is inversely proportional to the toner density, while the amount of the diffusion reflection light is directly proportional to the toner density.

Because the toner density is calculated based on the difference between reflection characteristics of the transfer belt and reflection characteristics of the toner pattern, it is necessary to analyze the specularly reflected light and the diffusely reflected light. From the viewpoint of, for example, the diffusely reflected light, the amount of light diffusely reflected by the toner pattern is proportional to the toner density. If light strikes the transfer belt, because the entire light is specularly reflected by the transfer belt, the amount of diffusely reflected light is zero.

Accordingly, the difference between the reflection characteristics of the transfer belt and the reflection characteristics of the toner pattern is small when the toner density is low. The difference between the reflection characteristics of the transfer belt and the reflection characteristics of the toner pattern is large when the toner density is high.

An algorithm that improves the accuracy in the toner-density calculation using the above-described toner pattern DP1 is described with reference to FIGS. 4 and 5.

Suppose, for example, that no toner pattern is formed on the transfer belt. When the light-emitting element E3 is ON and the detection light strikes the surface of the transfer belt 17, if light reflected by the surface of the transfer belt 17 is detected using the five light-receiving elements D1 to D5, the outputs from the three light-receiving elements D2 to D4 are larger than zero, while the outputs from the light-receiving elements D1 and D5 are zero. If the output from the light-receiving element D2 is assumed to "a", the output from the light-receiving element D3 is assumed to "b", and the output from the light-receiving element D4 is assumed to "c", then the reflection characteristics of the transfer belt is expressed by (a+b+c).

It is possible to calculate the ratio between the output from the light-receiving element D3 corresponding to the on-state light-emitting element E3 and the output from a light-receiving element, except the light-receiving element D3, on a position to receive light specularly reflected by the transfer belt (i.e., the light-receiving element D2 or D4 in this example). A ratio V between the light-receiving elements D3 and D2 is calculated using V=a/b. A ratio V' between the light-receiving elements D3 and D4 is calculated using V'=c/b.

Suppose, for example, that the toner pattern is formed on the transfer belt. When the light-emitting element E3 is ON and the detection light strikes the toner pattern DP1 on the transfer belt, the detection light is reflected both specularly and diffusely. Because the light-receiving element D3 receives only light specularly reflected, the output is completely due to specularly reflected light. In contrast, all the outputs from the four light-receiving elements other than the light-receiving element D3 are partially or completely due to diffusely reflected light.

It is noted that the outputs from the two light-receiving elements D1 and D5 are completely due to diffusely reflected light. This is drawn from the result that, when the detection light strikes the transfer belt, the specularly reflected light from the transfer belt is received at only the three light-receiving elements D2 to D4. In contrast, the outputs from the two light-receiving elements D2 and D4 are due to both light specularly reflected by the toner pattern and light diffusely reflected by the toner pattern.

Figure 6:
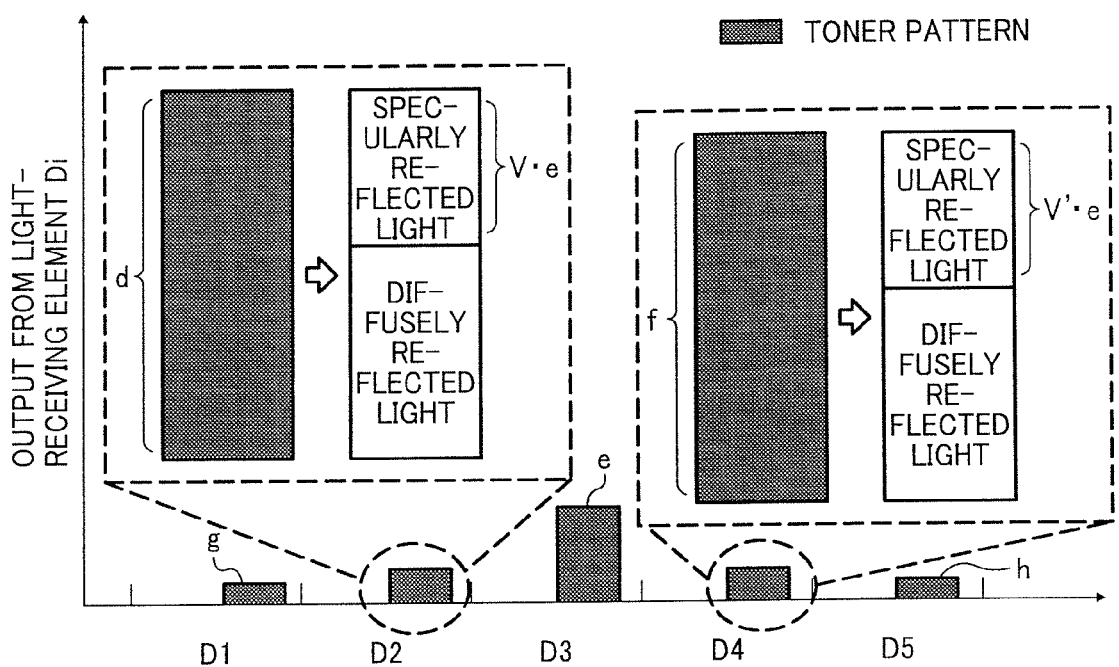
FIG. 6 is a schematic diagram that explains how the outputs from individual light-receiving elements shown in FIG. 5 are separated into an amount of specularly reflected light and an amount of diffusely reflected light.

The manner of calculating the ratio between the specularly reflected light and the diffusely reflected light is described below with reference to FIG. 6. If the output from the light-receiving element D2, which is observed when the detection light emitted from the light-emitting element E3 is reflected by the toner pattern on the transfer belt, is assumed to "d", the output from the light-receiving element D3 is assumed to "e", and the output from the light-receiving element D4 is assumed to "f", then V·e is the amount of light specularly reflected by the toner pattern contained in the output d, and the remaining (d−V·e) is the amount of light diffusely reflected by the toner pattern. In the same manner, V'·e is the amount of light specularly reflected by the toner pattern contained in the output f, and the remaining (d−V'·e) is the amount of light diffusely reflected by the toner pattern. In this manner, the outputs from the light-receiving elements D2 and D4 are separated into the amount of specularly reflected light and the amount of diffusely reflected light.

When the light-emitting element E3 is ON, solely and the toner pattern is exposed to the detection light, the sum of the amounts of light specularly reflected by the toner pattern extracted from the outputs from all the light-receiving elements D1 to D5 is e·(1+V+V'). It means that when compared with the case where only the output from the light-receiving element D3 is used for the toner-density calculation, the total amount is increased by e·(V+V'). The sum of the amounts of light diffusely reflected by the toner pattern extracted from the outputs from all the light-receiving elements D1 to D5 is g+h+(d−V·e)+(f−V'·e), in which g is the output from the light-receiving element D1 and h is the output from the light-receiving element D5. It means that, when compared with the case where only the outputs from the light-receiving elements D1 and D5 are used for the toner-density calculation, the total amount is increases by (d−V·e)+(f−V'·e).

Figure 7:
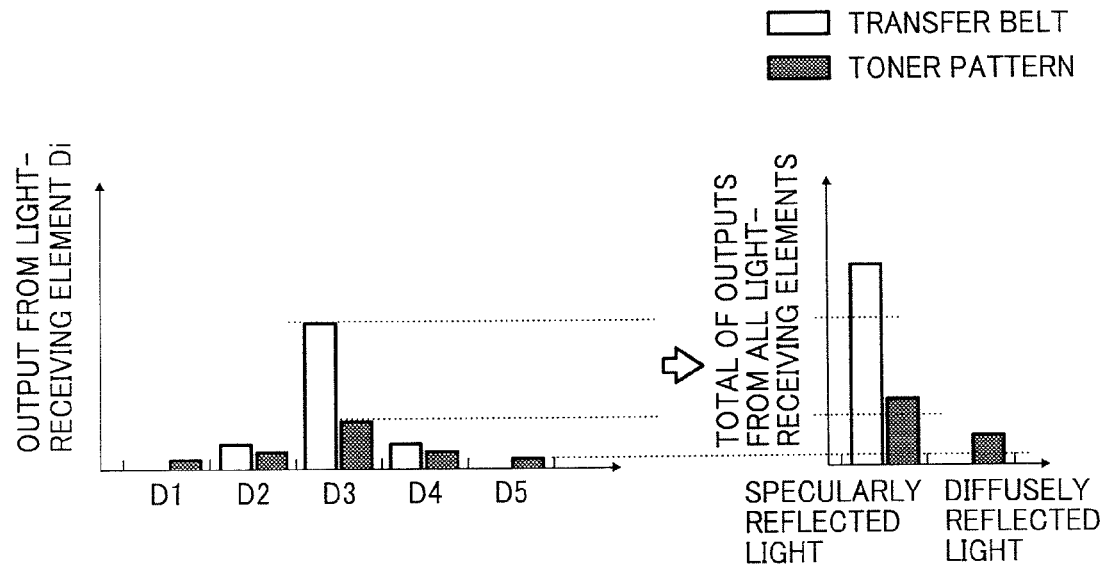
FIG. 7 is a graph of the sum of the amounts of specularly reflected light and the sum of the amounts of diffusely reflected light that are plotted in FIGS. 4 and 5.

As described above, the output from the light-receiving elements D2 and D4 are separated into the amount of specularly reflected light and the amount of diffusely reflected light. As shown in FIG. 7, the sum of the amounts of light specularly reflected by the toner pattern extracted from the outputs from all the light-receiving elements D1 to D5 and the sum of the amounts of light diffusely reflected by the toner pattern extracted from the outputs from all the light-receiving elements D1 to D5 are calculated as the reflection characteristics of the toner pattern. The toner density is calculated on the basis of the difference between the reflection characteristics of the toner pattern and the reflection characteristics of the transfer belt. In this manner, the reflected light is efficiently used.

Therefore, if the above-described algorithm is used in the toner-density calculating method, the outputs from the light-receiving elements are improved. This results in a decrease in the consumed power of the light-receiving elements and an increase in the lifetime of the light-receiving elements.

Although the algorithm is described with the simple example M=N=5, the algorithm is applicable to the example where M and N are set to, for example, 100, i.e., one hundred of the light-emitting elements E1 to E100 and one hundred of the light-receiving elements D1 to D100 are provided.

Suppose, for example, that the center of the toner pattern DP1 in the main-direction is on the spot of the detection light coming from the light-emitting element E50.

Firstly, it is identified, on the basis of the outputs from the light-receiving elements that are observed when the detection light from the light-emitting element E50 strikes the area out of the toner pattern on the transfer belt 17, which light-receiving elements will receive light specularly reflected by the toner pattern and which light-receiving elements will not receive light specularly reflected by the toner pattern. The ratio (i.e., V and V') is then calculated between the output from the light-receiving element D50 corresponding to the light-emitting element E50 and the output from each light-receiving element, except the light-receiving element D50, on a position to receive light specularly reflected by the transfer belt.

After that, when the center of the toner pattern DP1 in the main-direction is on the spot of the detection light from the light-emitting element E50, the amount of light specularly reflected by the toner pattern that is formed on the transfer belt 17 and the amount of light diffusely reflected by the toner pattern are extracted from an output from each light-receiving element. The output from the light-receiving element D50, which is the one corresponding to the light-emitting element E50, is completely due to specularly reflected light. By using the output from the light-receiving element D50, the outputs from the light-receiving elements other than the light-receiving element D50, and the above-described ratios, the output from each light-receiving element, except the light-receiving element D50, is separated into the amount of light specularly reflected by the toner pattern and the amount of light diffusely reflected by the toner pattern.

In this manner, even if there are provided with one hundred of light-emitting elements and one hundred of light-receiving elements, the above-described algorism is applicable. Although the description is not made, the algorism is also applicable to even the case of MSN (M does not differ to N).

Moreover, the algorism is applicable to the case where the transfer belt is not a specular material but a diffusing material. The case is described in detail below. To make the description simpler, M and N are set to seven (M=N=7).

Figure 8:
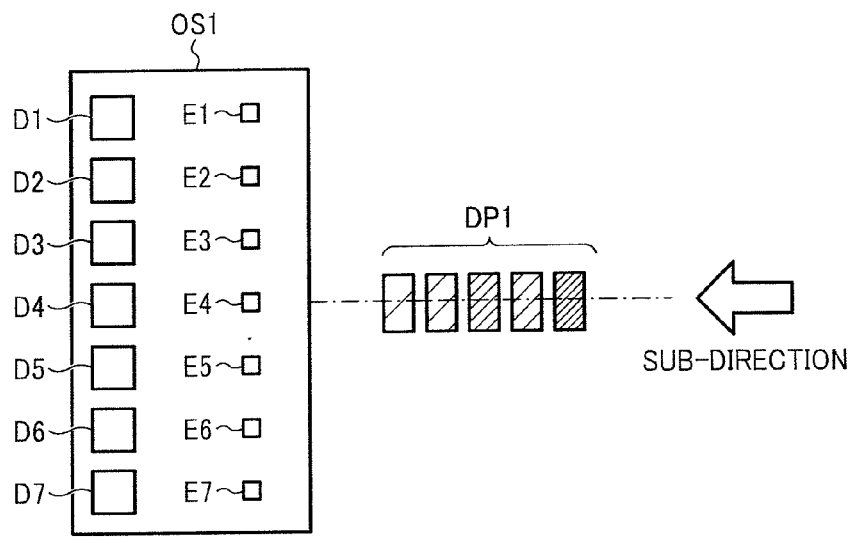
FIG. 8 is a plan view that explains how the toner pattern is detected if a supporting member is made of a diffusing material.
Figure 9:
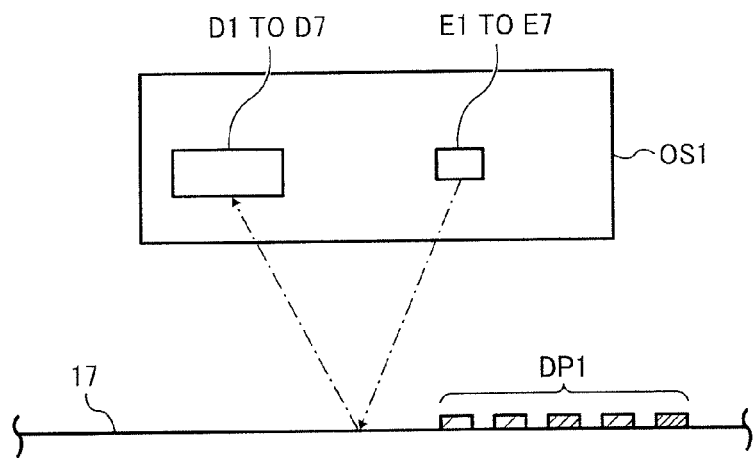
FIG. 9 is a longitudinal cross-sectional view that explains how the toner pattern is detected if the supporting member is made of the diffusing material.
Figure 9:
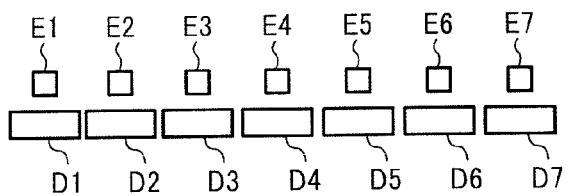
Figure 10:
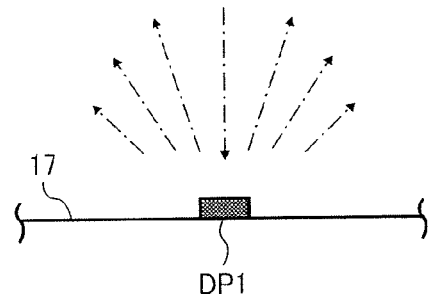
FIG. 10 is a schematic diagram that explains, during the toner-pattern detecting process, how detection light is reflected by the toner pattern if the supporting member is made of the diffusing material.

A reflective optical sensor, including seven light-emitting elements and seven light-receiving elements, is shown in FIG. 8. Although the reflective optical sensor shown in FIG. 8 is different from the reflective optical sensor shown in FIG. 3A in the number of the light-emitting elements and the number of the light-receiving elements, they have the same mechanism. FIG. 9 is a side view of the reflective optical sensor shown in FIG. 8. FIG. 10 is a schematic diagram that explains how the detection light is reflected by the toner pattern DP1 when the center of the toner pattern DP1 is on the spot of the detection light coming from the light-emitting element E4.

For more actuality, it is assumed that the transfer belt 17 is made of a diffusing material. When the detection light, coming from a light-emitting element, strikes the surface of the transfer belt, the reflected light is received at the light-receiving element corresponding to the on-state light-emitting element, the two light-receiving elements adjacent to the corresponding light-receiving element, and the light-receiving elements adjacent to the adjacent light-receiving elements.

In the example shown in FIG. 9, when the light-emitting element E4 turns ON, the detection light reflected by the surface of the transfer belt is received at the five light-receiving elements that include the light-receiving element D4 which is the one corresponding to the light-emitting element E4, the light-receiving elements D3 and D5 that are adjacent to the light-receiving element D4, and the light-receiving elements D2 and D6 that are adjacent to the light-receiving elements D3 and D5, while no light is received at the light-receiving elements D1 and D7.

In other word, the outputs from the five light-receiving elements D2 to D6 are larger than zero, while the outputs from the two light-receiving elements D1 and D7 are zero. The light-emitting elements E1 to E7 are, for example, LEDs. The light-receiving elements D1 to D7 are, for example, PDs.

Figure 11:
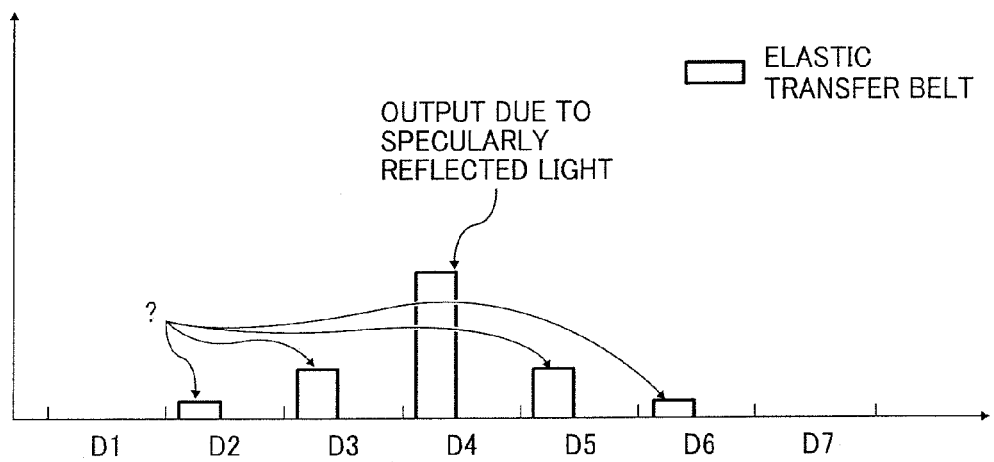
FIG. 11 is a graph of output distribution observed when the supporting member is made of the diffusing material.

If no toner pattern is formed on the transfer belt made of a diffusing material (hereinafter, "elastic transfer belt"), when the light-emitting element E4 turns ON, the detection light reflected by the surface of the elastic transfer belt is received at the seven light-receiving elements D1 to D7, in some cases, as shown in FIG. 11, the outputs from the five light-receiving elements D2 to D6 are larger than zero, while the outputs from the light-receiving elements D1 and D7 are zero. The output from the light-receiving element D4 is estimated to be completely due to light specularly reflected by the elastic transfer belt; however, it is impossible to determine whether the outputs from the four light-receiving elements D2, D3, D5, and D6 are completely due to light specularly reflected by the elastic transfer belt, completely due to light diffusely reflected, or due to both light specularly reflected and light diffusely reflected.

Figure 12:
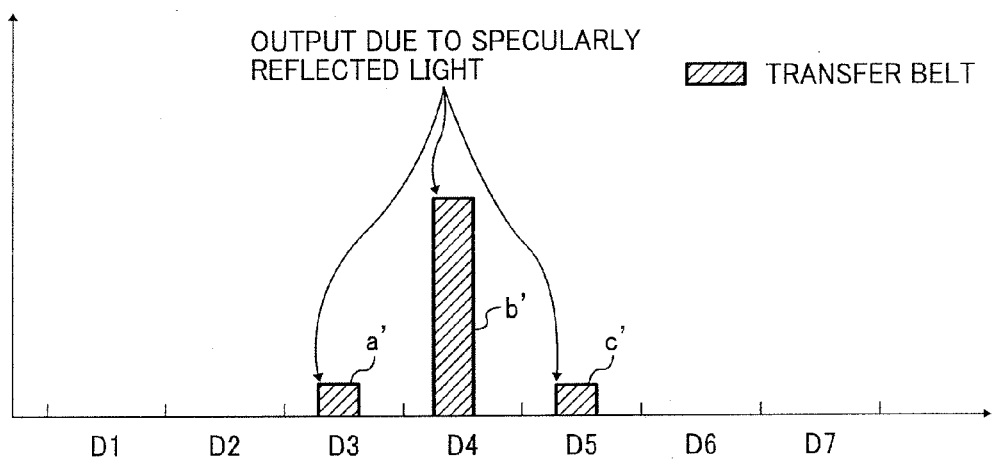
FIG. 12 is a graph of output distribution observed when the supporting member is the transfer belt that is made of the specular material.

Before obtaining the PD output distribution observed when the detection light strikes the elastic transfer belt, it is necessary to obtain a PD output distribution observed when the detection light strikes the transfer belt made of a specular material (hereinafter, "transfer belt", in short) as a sample. If the graph shown in FIG. 12 is obtained as the PD output distribution, the outputs from the light-receiving elements D2 and D6 shown in FIG. 11 are determined to be completely due to light diffusely reflected by the elastic transfer belt.

Figure 13:
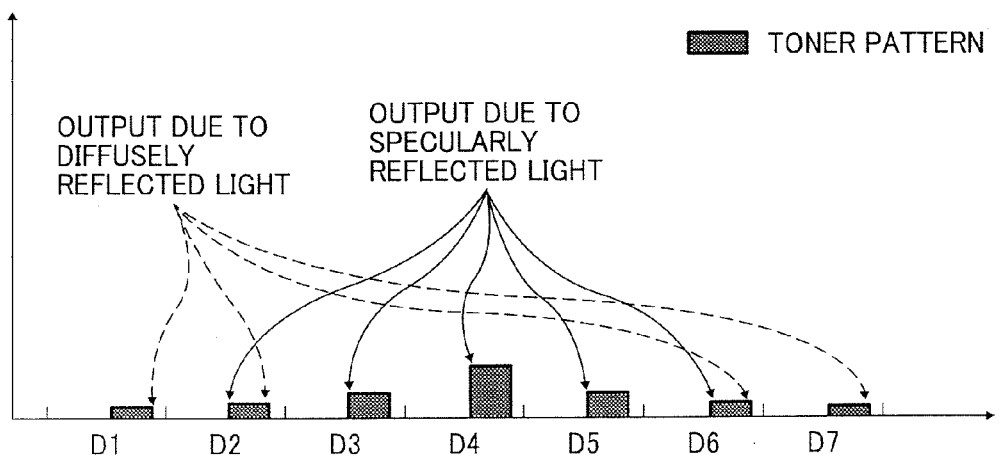
FIG. 13 is a graph of output distribution observed when the detection light strikes the toner pattern that is formed on the supporting member made of the diffusing material.

Accordingly, it is determined that the output from each of the light-receiving elements D3 and D5 shown in FIG. 11 is due to both light specularly reflected by the elastic transfer belt and light diffusely reflected by the elastic transfer belt. Therefore, if a' is the output from the light-receiving element D2, b' is the output from the light-receiving element D3, and c' is the output from the light-receiving element D4 observed when the detection light strikes the transfer belt, then it is possible to separate the output from each of the light-receiving elements D3 and D5 shown in FIG. 11 into the amount of specularly reflected light and the amount of diffusely reflected light in the same manner as described with reference to FIGS. 3A to 3F. Even when the PD output distribution shown in FIG. 13 is obtained when the detection light strikes the toner pattern formed on the elastic transfer belt, by using the PD output distribution obtained when the detection light strikes the transfer belt (shown in FIG. 12), it is possible to calculate the ratio of each light-receiving element between the amount of light specularly reflected by the toner pattern and the amount of light diffusely reflected by the toner pattern.

In this manner, although it is necessary to obtain the PD output distribution using the specular material as a sample, the above-described algorithm is applicable to a transfer belt made of a diffusing material.

As described above, with this algorithm, the detection light can accurately strike the toner pattern and the correct toner density is calculated using the reflective optical sensor. Moreover, the efficiency in the toner-density calculation is improved. Moreover, because the light-emitting elements and the light-receiving elements are aligned at an extremely small pitch, even if the length of the toner pattern in the main-direction is small, the position of the toner pattern in the main-direction is detected accurately by such small unit the same as the pitch.

In the embodiment described with reference to FIG. 15, if independent extremely small LEDs and PDs aligned at about 1-mm pitch are used as the light-emitting elements E1 to E5 and the light-receiving elements D1 to D5, the length of the toner pattern DP1 in the main-direction is enough to about 1 mm. If the toner pattern DP1 includes the five rectangular toner patterns as shown in FIG. 3A, the width of each toner pattern in the sub-direction is enough to smaller than about 1 mm and the area of the toner pattern DP1 is 5 mm$^2$.

That is, the area needed for the toner pattern decreases to ⅕₂₅ of the conventional toner pattern with 25 mm×25 mm. Because such a toner image with a small area can be formed in a short time, the operating efficiency of the image formation will not decrease. Moreover, the amount of the toner for the toner pattern remarkably decreases to ⅕₂₅ in the same ratio as the area of the toner pattern decreases.

Figure 3D:
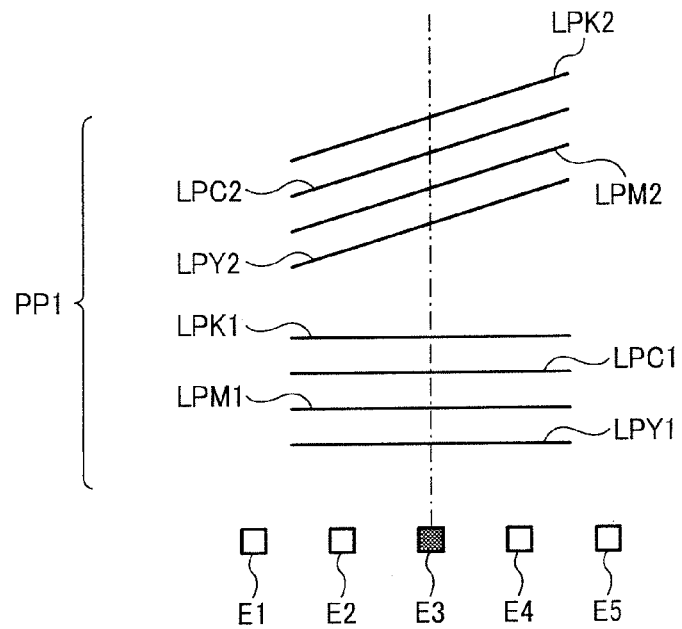
Figure 3E:
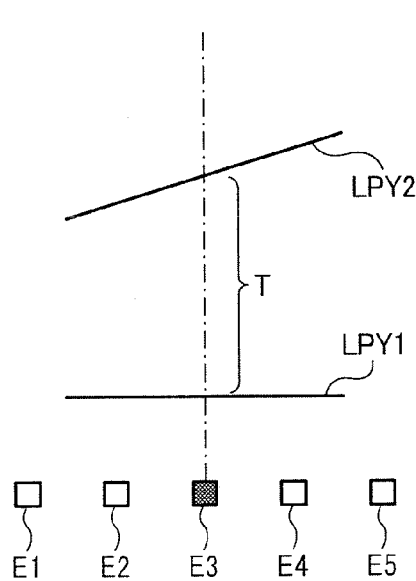
Figure 3F:
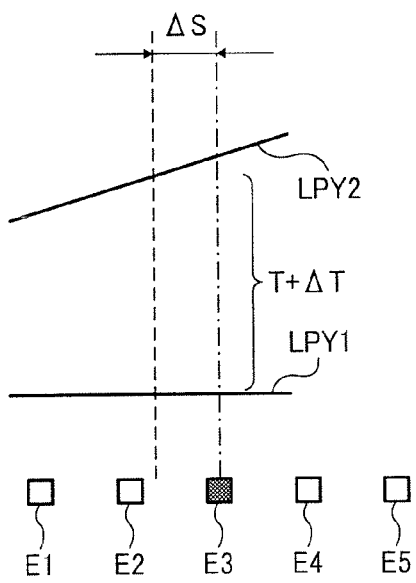

FIGS. 3D to 3F are schematic diagrams that explains the position detection using the position detecting pattern PP1.

The position detecting pattern PP1 includes parallel line patterns LPY1, LPM1, LPC1, and LPK1 each parallel to the main-direction, and slant line patterns LPY2, LPM2, LPC2, and LPK2 each not parallel to the main-direction. The line patterns LPY1 and LPY2 make a pair, and are formed with the yellow toner. The line patterns LPM1 and LPM2 make a pair, and are formed with the magenta toner. The line patterns LPC1 and LPC2 make a pair, and are formed with the cyan toner. The line patterns LPK1 and LPK2 make a pair, and are formed with the black toner.

The four pairs of the line patterns are formed in such a manner that the pairs are to be aligned in the sub-direction at a fixed interval. If the pairs are actually aligned at the fixed interval in the sub-direction, it is determined that the positional relation among the yellow toner image, the magenta toner image, the cyan toner image, and the black toner is correct in the sub-direction.

To determine whether the positional relation in the sub-direction is correct, for example as shown in FIG. 3F, the light-emitting element E3 turns ON when the position detecting pattern PP1 comes close to the detection area of the reflective optical sensor. The light-emitting element E3 is ON for a continuous time. As the position detecting pattern PP1 moves, the spot of the detection light emitted from the light-emitting element E3 relatively moves in the sub-direction on the supporting member, thereby illuminating the line patterns LPY1 to LPK1 one by one.

When the detection light strikes any of the line patterns, the time interval for the detection light to move between each of the four pairs of line patterns is calculated by analyzing temporal change in the outputs from the light-receiving elements D1 to D5. If the time intervals are equal, it is determined that the positional relation among the toner images in the sub-direction is correct. If the time intervals are not equal, it is determined that the positional relation is not correct. Moreover, a deviation amount in the positional relation can be calculated from the change in the outputs. If the positional relation is not correct, the timing to start the optical scanning is adjusted based on the deviation amount.

On the other hand, the positional relation in the main-direction among the toner images is determined in the following manner. In the following description, the position of the yellow toner image is detected with reference to FIGS. 3E and 3F as an example.

FIG. 3E is a schematic diagram of the yellow toner image that is arranged in the correct position in the main-direction (the side-to-side direction of FIG. 3E). It takes time T for the spot of the detection light to move from the line pattern LPY1 to the line pattern LPY2. FIG. 3F is a schematic diagram of the yellow toner image that is arranged in an incorrect position deviated by ΔS in the main-direction. Because the line pattern LPY2 is not parallel to the line pattern LPY1, time required for the spot of the detection light to move from the line pattern LPY1 to the line pattern LPY2 is longer, i.e., T+ΔT. Therefore, the deviation amount is calculated from ΔT that is a difference between T and T+ΔT.

More particularly, the relation between ΔS and ΔT is as follows:

$$\Delta S \cdot \tan \theta = V \cdot \Delta T$$

where θ is angle between the line pattern LPY2 and the main-direction, and V is velocity of the transfer belt 17 as the supporting member in the sub-direction. Therefore, ΔS is calculated as follows:

$$\Delta S = V \cdot \Delta T \cdot \cot \theta$$

As described with reference to FIGS. 3A to 3C, in the reflective optical sensor OS1, the light-emitting elements E1 to E5 turn ON/OFF sequentially to detect the toner patterns. It takes a certain time from the ON/OFF of the light-emitting element E1 to the ON/OFF of the light-emitting element E5. The certain time is called "scanning time".

The toner pattern (i.e., individual rectangular toner patterns) should be within an area to be subjected to the spot scanning by the reflective optical sensor (i.e., area where the sequentially flashing spots of the detection light falls) (hereinafter, "scanning area") during the scanning time. In other words, the sequential ON/OFF of the light-emitting elements E1 to E5 are performed while the toner pattern is within the scanning area.

If M, which is the number of the light-emitting elements of the reflective optical sensor, is small, the scanning time will be short. However, as described above, to maintain the operating efficiency of the image formation by decreasing the time to form the toner pattern and efficiently reduce the amount of the toner for the toner pattern, decrease in the area of the toner pattern is required. To correctly exposing the small toner pattern to the detection light, thereby calculating the correct toner density, it is necessary to decrease the pitch of the light-emitting elements and the light-receiving elements by an amount that corresponds to the decrease in the length of the toner pattern in the main-direction. The length of the arrangement area of the light-emitting elements and the light-receiving elements is required to be about 10 mm in consideration for the miss-match between the toner pattern and the reflective optical sensor in the main-direction. As the pitch decreases, M, which is the number of the light-emitting elements, increases to a remarkably large number. As M increases, the scanning time increases.

The supporting member with the toner pattern formed thereon moves by a distance V·st in the sub-direction for the scanning time, where st is scanning time and V is velocity of the supporting member moving in the sub-direction.

If M is too large while V is unchanged, the scanning time becomes longer than time required for the toner pattern to pass through the scanning area. If so, it is difficult to calculate the correct toner density.

Figure 14A:
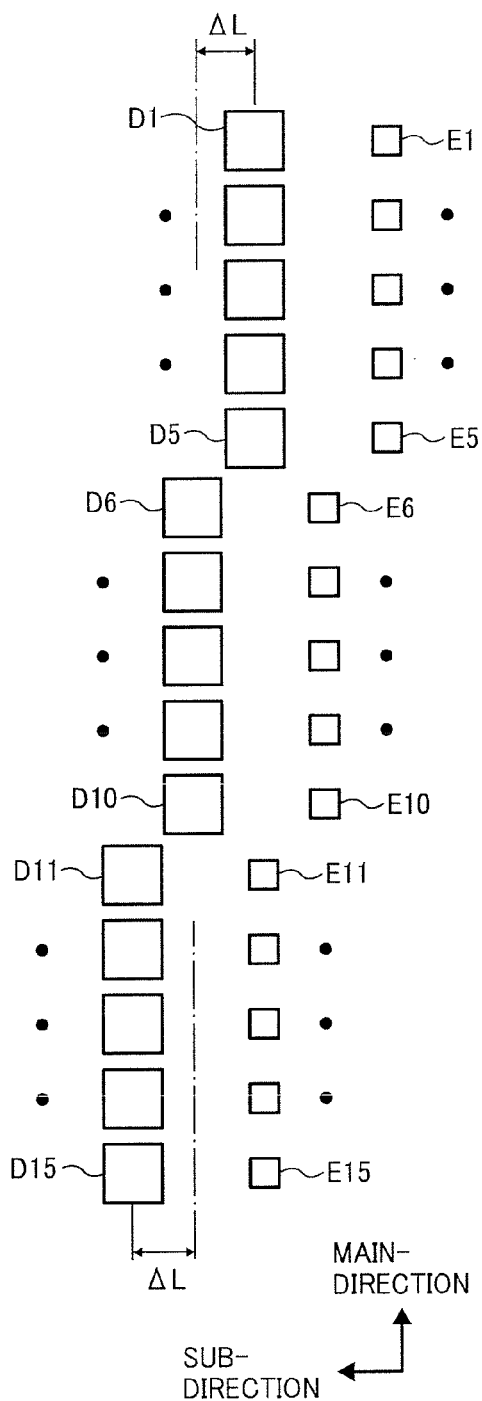
FIGS. 14A and 14B are schematic diagrams of two examples of arrangement of light-emitting elements and light-receiving elements included in the reflective optical sensor.
Figure 14B:
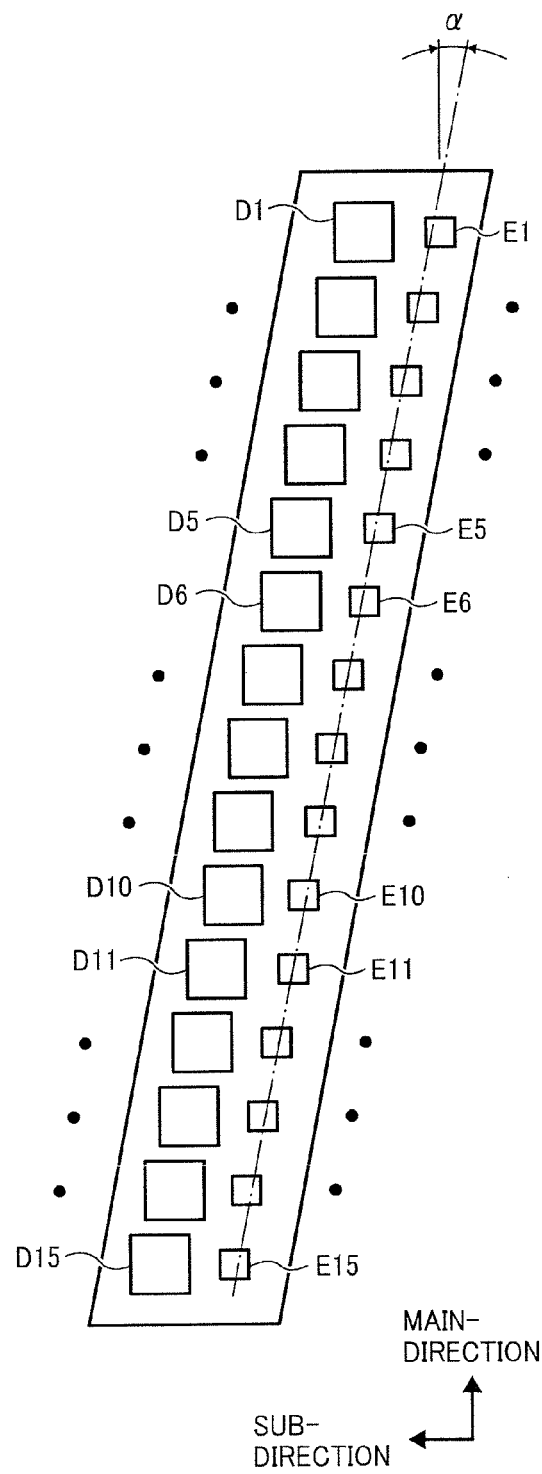

FIGS. 14A and 14B are schematic diagrams of embodiments that give a solution to the above problem. Reflective optical sensors according to the embodiments shown in FIGS. 14A and 14B include 15 light-emitting elements E1 to E15 and 15 light-receiving elements D1 to D15. The light-emitting elements E1 to E15 corresponds the light-receiving elements D1 to D15, respectively in the one-to-one manner. The numbers of the light-emitting elements and the light-receiving elements shown in FIGS. 14A and 14B are set to fifteen to make the description simpler. Several tens to several hundreds of the light-emitting elements and the light-receiving elements will be used in practice.

In the embodiment shown in FIG. 14A, the light-emitting elements E1 to E15 and the light-receiving elements D1 to D15 are aligned in a single direction (the up-and-down direction of FIG. 14A). Moreover, the light-emitting elements E1 to E15 and the light-receiving elements D1 to D15 that are divided into a first group, a second group, and a third group. The first group includes the light-emitting elements E1 to E5 and the light-receiving elements D1 to D5; the second group includes the light-emitting elements E6 to E10 and the light-receiving elements D6 to D10; and the third group includes the light-emitting elements E11 to E15 and the light-receiving elements D11 to D15. The light-emitting elements of each group are aligned in a single line, and the light-receiving elements of each group are aligned in a single line. When the reflective optical sensor is in position to calculate the toner density, the line of the second group is shifted by ΔL from the line of the first group in the sub-direction (the side-to-side direction of FIG. 14A), and the line of the third group is shifted by ΔL from the line of the second. The distance ΔL is set based on the velocity of the supporting member moving in the sub-direction.

The light-emitting elements E1 to E15 turn ON/OFF sequentially while the toner pattern is moving in the sub-direction at the velocity of V. Time required for ON/OFF of the light-emitting elements E1 to E5, time required for ON/OFF of the light-emitting elements E6 to E10, and time required for ON/OFF of the light-emitting elements E11 to E15 are equal, more particularly, st/3, where st is scanning time.

The toner pattern moves by distance V·st/3 in the sub-direction in time st/3. Therefore, if ΔL is set as follows:

$$\Delta L = V \cdot st/3$$

then the spot scanning of the toner pattern by the light-emitting elements E1 to E15 is completed within the scanning time.

In the embodiment shown in FIG. 14B, when the reflective optical sensor is in position to calculate the toner density, the light-emitting elements E1 to E15 and the light-receiving elements D1 to D15 are aligned in a single direction that makes an angle α with the main-direction (the up-and-down direction of FIG. 14B). The angle α is set according to the velocity V of the supporting member moving in the sub-direction (toward the left side of FIG. 14B).

More particularly, if the angle α satisfies the following Equation:

$$Z \cdot \tan \alpha = V \cdot st$$

where st is scanning time, Z is the length in the main-direction of lines on which the light-emitting elements E1 to E15 and the light-receiving elements D1 to D15 are aligned, then the spot scanning of the toner pattern by the light-emitting elements E1 to E15 is completed within the scanning time.

Figure 15:
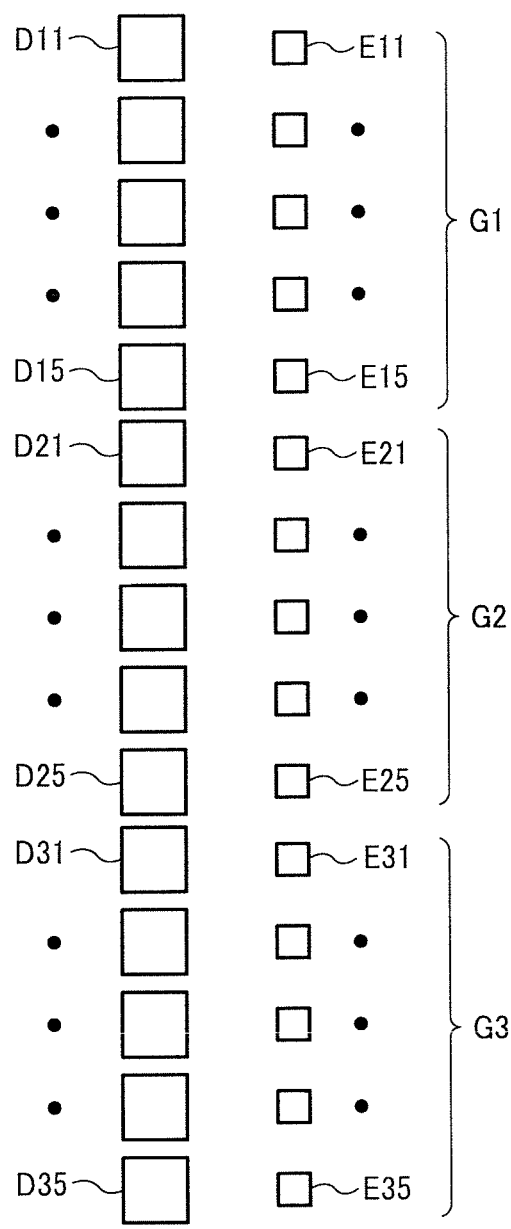
FIG. 15 is a schematic diagram of an example that solves properly a problem in the spot scanning.

In an embodiment as shown in FIG. 15, the spot scanning is optimized as follows.

A reflective optical sensor according to the embodiment shown in FIG. 15 also includes 15 light-emitting elements and 15 light-receiving elements. The light-emitting elements correspond to the light-receiving elements, respectively in the one-to-one manner. To make the description simpler, the numbers of the light-emitting elements and the light-receiving elements shown in FIG. 15 are set to fifteen. Several tens to several hundreds of the light-emitting elements and the light-receiving elements will be used in practice.

When the reflective optical sensor is in position to calculate the toner density according to the embodiment shown in FIG. 15, the single direction in which the 15 light-emitting elements are aligned and the single direction in which the 15 light-receiving elements are aligned are substantially parallel to the main-direction (the up-and-down direction of FIG. 15).

Each of the 15 light-emitting elements makes a pair with a corresponding one of the 15 light-receiving elements. The light-emitting elements and the light-receiving elements are divided into three groups G1, G2, and G3. The groups G1, G2, and G3 are aligned in a single line extending in the main-direction.

The group G1 includes five pairs, more particularly, the light-emitting elements E11 to E15 and the light-receiving elements D11 to D15. The group G2 includes five pairs, more particularly, the light-emitting elements E21 to E25 and the light-receiving elements D21 to D25. The group G3 includes five pairs, more particularly, the light-emitting elements E31 to E35 and the light-receiving elements D31 to D35.

All the three groups G1, G2, and G3 have the same configuration.

When the reflective optical sensor is in position to calculate the toner density, 15 light-emitting elements turns ON/OFF sequentially in such a manner that three corresponding light-emitting elements selected from the groups G1, G2, and G3 turn ON simultaneously.

During the spot scanning, the first light-emitting element of each group, i.e., the light-emitting elements E11, E21, and E31 turn ON/OFF simultaneously. Then, the second light-emitting element of each group, i.e., the light-emitting elements E12, E22, and E32 turn ON/OFF simultaneously. After that, the light-emitting elements E13, E23, and E33, the light-emitting elements E14, E24, and E34, and the light-emitting elements E15, E25, and E35 turn ON/OFF sequentially.

With this configuration, the scanning time can be decreased to one-third of the scanning time (st/3) in the embodiments shown in FIGS. 14A and 14B. Therefore, the spot scanning is completed while the toner pattern is passing through the scanning area.

As a variation of the embodiment shown in FIG. 15, it is allowable to shift the light-emitting elements and the light-receiving elements other than the light-emitting elements E11, E21, and E31 and the light-receiving elements D11, D21, and D31 in the sub-direction (toward the left side of FIG. 15) with the light-emitting elements E11, E21, E31 and the light-receiving elements D11, D21, D31 maintained at their respective positions shown in FIG. 15 in such a manner that the light-emitting elements and the light-receiving elements are aligned in a direction that makes a certain angle with the main-direction (toward the left side of FIG. 15) in the same manner as in the embodiment shown in FIG. 14B. The certain angle is set according to the speed at which the supporting member moves in the sub-direction.

More light-emitting elements and light-receiving elements are used in the embodiments shown in FIGS. 14A, 14B, and 15. If the pitch is unchanged, the length of the reflective optical sensor in the main-direction, i.e., the sensing area increases. In other words, an allowable extent of the positional miss-match in the main-direction between the toner pattern and the reflective optical sensor increases. On the other hand, if the length of the reflective optical sensor is unchanged, the pitch between adjacent light-emitting elements and light-receiving elements decreases. This results in an increase in the spatial resolution in the main-direction.

As described above, M, which is the number of the light-emitting elements, can be set unequal to N, which is the number of the light-receiving elements. Three embodiments with M unequal to N are shown in FIGS. 16A to 16C.

Figure 16A:
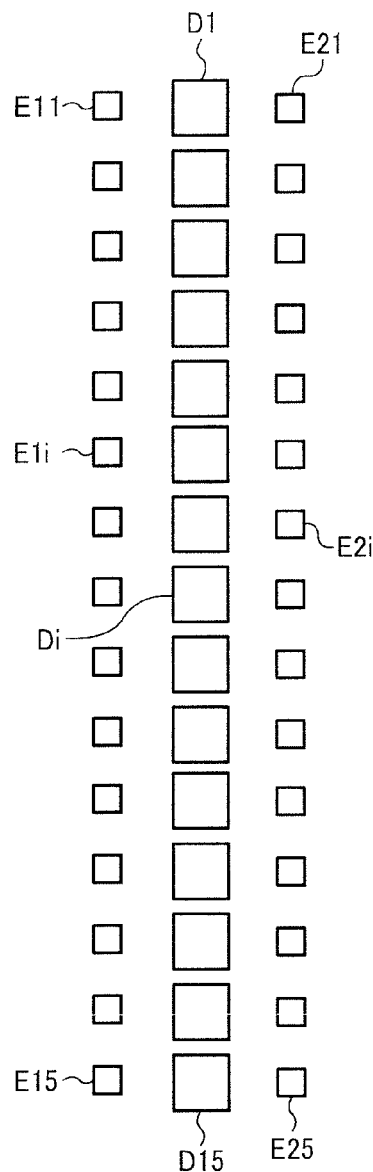
FIGS. 16A to 16C are schematic diagrams of three examples of arrangement of light-emitting elements and light-receiving elements included in the reflective optical sensor.
Figure 16B:
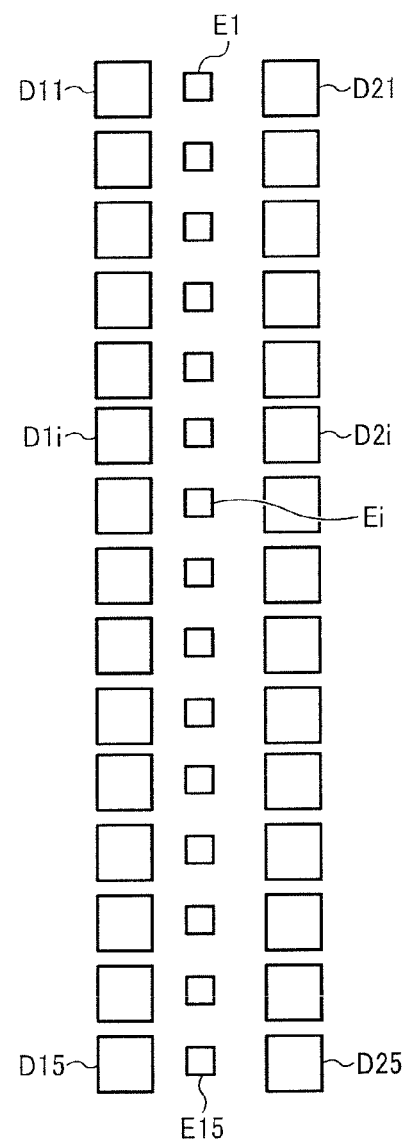
Figure 16C:
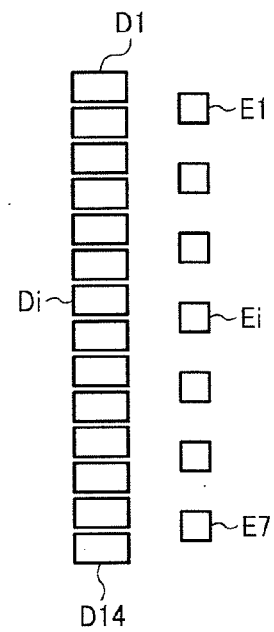

In the embodiment shown in FIG. 16A, N is 15 and M is 30. The light-emitting unit includes 15 light-emitting elements E11, . . . , E1i . . . , and E15 that are aligned in a single line extending in the main-direction at an equal pitch, and 15 light-emitting elements E21, . . . , E2$i$ . . . , and E25 that are aligned in another single line extending in the main-direction at an equal pitch. Positions of the light-emitting elements E21, . . . , E2$i$ . . . , and E25 in the main-direction are the same as positions of the light-emitting elements E11, . . . , E1$i$ . . . , and E15, respectively.

The light-receiving unit includes 15 light-receiving elements D1, . . . , D$i$ . . . , and D15 that are aligned in a line extending in the main-direction at an equal pitch between the two lines of the light-emitting elements. Positions of the light-receiving elements D1, . . . , D$i$ . . . , and D15 are the same in the main-direction as the positions of the light-emitting elements E11, . . . , E1$i$ . . . , and E15, respectively, i.e., the same in the main-direction as the positions of the light-emitting elements E21, . . . , E2$i$ . . . , and E25, respectively. The light-emitting elements E11 and E21, which are aligned in the same position in the main-direction, turn ON/OFF simultaneously. After that, the light-emitting elements E1$i$ and E2$i$ turn ON/OFF, simultaneously. The ON/OFF operation is repeated in the same manner until the light-emitting elements E15 and E25 turn ON/OFF. Thus, the output of the detection light that illuminates the supporting member and the toner pattern becomes about double.

The output of the LEDs, which are used as the light-emitting elements, in general, depends on not the light-emitting-element area but the applied current density. If the applied current density increases, the output increases but the lifetime of the LEDs decreases. To maintain the lifetime, the applied current density is preferably lower than a certain level. If the light-emitting-element area increases (with the applied current density unchanged), the applied current amount increases. However, an increase in the light-emitting-element area results in an increase of spots for illuminating the supporting member and the toner pattern. To solve this problem, it is preferable to double the output of the light. This has been achieved by arranging the two lines of light-emitting elements, as shown in FIG. 16A, with both the light-emitting-element area and the current density unchanged.

In the embodiment shown in FIG. 16B, N is 30 and M is 15. The light-receiving unit includes 15 light-receiving elements D11, . . . , D1$i$ . . . , and D115 that are aligned in a single line extending in the main-direction at an equal pitch, and 15 light-receiving elements D21, . . . , D2$i$ . . . , and D215 that are aligned in another single line extending in the main-direction at an equal pitch. The light-emitting unit includes 15 light-emitting elements E1, . . . , E$i$ . . . , and E15 that are aligned in a single line extending in the main-direction at an equal pitch between the two lines of the light-receiving elements. Positions of the light-emitting element E$i$, the light-receiving element D1$i$, and the light-receiving element D2$i$, where i is an arbitrary integer from 1 to 15, are the same in the main-direction.

Because PDs, which receive the detection light (reflected light), are aligned in the two lines, the light-receiving sensitivity becomes double. Alternatively, if the light-receiving-element area in the sub-direction is increased to double with the PDs being aligned in a single line, the light-receiving sensitivity increases. However, the increase in the light-receiving sensitivity is relatively small, especially when the size of the spot of the detection light reflected from the supporting member and the toner pattern is small. From the viewpoint of the improvement of the light-receiving sensitivity, it is more effective to arrange the PDs in the two lines symmetrically in the sub-scanning direction and the LEDs between the two lines, as shown in FIG. 16B.

In the embodiments as described with reference to FIGS. 2 to 16B, the light-emitting elements and the light-receiving elements are aligned at the equal pitches, and the pitch of the light-emitting elements is equal to the pitch of the light-receiving elements. However, it is possible to set the pitch of the light-emitting elements different from the pitch of the light-receiving elements.

The embodiment shown in FIG. 16C is described below. In this embodiment, there are seven light-emitting elements E1, . . . , E$i$, . . . , and E7 and 14 light-receiving elements D1, . . . , D$i$, . . . , and D14. The light-receiving elements are aligned at a pitch half of the pitch of the light-emitting elements. Each of the light-emitting elements E1 to E7 corresponds to two light-receiving elements.

In this manner, the spatial resolution in the main-direction in increased by decreasing the pitch of the PDs. In this case, the light-emitting element E$i$ corresponds to the light-receiving elements D$j$ and D$j$+1 (j=2i−1).

If the reflective optical sensor is arranged in a line not parallel to the main-scanning direction, the higher spatial resolution in the main-direction is obtained. Assume, more particularly, that the reflective optical sensor is arranged in such a manner that an angle between the main-scanning direction and the lines on which the light-emitting elements and the light-receiving elements are aligned is $\beta$, and the pitch of the light-emitting elements and the light-receiving elements is pt. Then, the pitch of points in the main-direction projected from the light-emitting elements and the light-receiving elements is decreased to pt·cos $\beta$, i.e., the spatial resolution increases.

In the above-described embodiments, the LEDs and the PDs are formed as the light-emitting elements and the light-receiving elements by the resin molding or by the surface mounting at an integrated and high-density manner.

As described above, if extremely small LEDs and PDs dimensions of which can be adjusted in the millimeter are used, the pitch can be decreased to about 1 mm.

To increase the spatial resolution, it is necessary basically to decrease the pitch of the light-emitting elements and the light-receiving elements. In an LED array and a PD array in which LEDs and PDs are integrally arranged, the pitch is extremely small. Two embodiments using an LED array and a PD array are described with reference to FIGS. 17A and 17B.

Figure 17A:
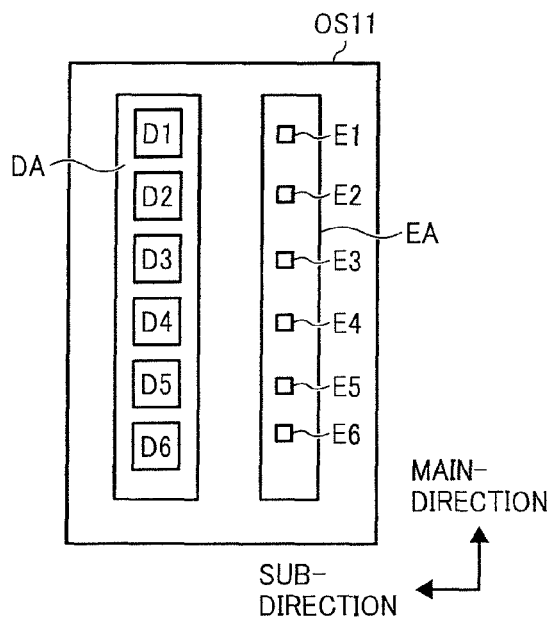
FIGS. 17A and 17B are schematic diagrams of two examples of reflective optical sensors according to the embodiment.

In the embodiment shown in FIG. 17A, a reflective optical sensor OS11 includes an LED array (light-emitting unit) EA and a PD array (light-receiving unit) DA. The LED array EA includes six LEDs as the light-emitting elements E1 to E6 integrally aligned in a single line at an equal pitch on the same substrate. The PD array DA includes six PDs as the light-receiving elements D1 to D6 integrally aligned in a single line at an equal pitch on the same substrate. The LED array EA and the PD array DA are accommodated in the same housing of the reflective optical sensor OS11.

Figure 17B:
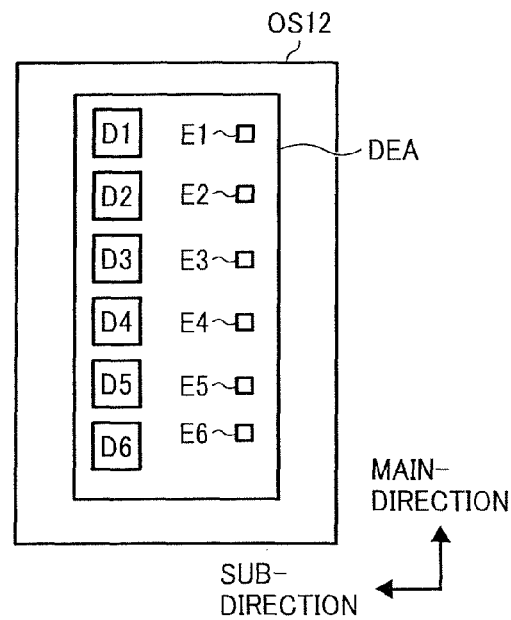

In the embodiment shown in FIG. 17B, a reflective optical sensor OS12 includes a light-emitting/receiving unit array DEA. The light-emitting/receiving unit array DEA includes six LEDs as the light-emitting units E1 to E6 and six PDs as the light-receiving elements D1 to D6 arranged on the same substrate. The six LEDs are aligned in a single line at an equal pitch. The six PDs are aligned in a single line at an equal pitch. The light-emitting/receiving unit array DEA is accommodated in the same housing of the reflective optical sensor OS12.

As shown in FIGS. 17A and 17B, the pitch of the light-emitting elements is equal to the pitch of the light-receiving elements. A position of each light-emitting element in the main-direction is the same as a position of the corresponding light-receiving element. However, in the same manners as in the embodiments shown in the FIGS. 16A to 16C, the number of and the pitch of the light-emitting elements can be different from the number of and the pitch of the light-receiving elements.

To make the drawings and the description simpler, only six light-emitting elements and six light-receiving elements are shown in FIGS. 17A and 17B.

In this manner, if the LED array and the PD array are used as the light-emitting unit and the light-receiving unit, the pitch of the light-emitting elements and the light-receiving elements can be from several tens of micrometers order to several hundreds of micrometers order. In other words, an extremely high spatial resolution can be obtained.

If the LED array and the PD array that are fabricated by the semiconductor processing are used instead of individual LEDs and PDs, it is possible to obtain a remarkably high positional accuracy in the light-emitting elements and the light-receiving elements.

In the embodiment shown in FIG. 17B, because the LED array and the PD array are integrally formed on the same substrate, a relative positioning between the light-emitting elements and the light-receiving elements can be set extremely accurately.

As for the reflection properties of the toner patterns, the toner pattern in each color has different dependency to the wavelength. However, the toner pattern in each color has almost the same dependency to the near-infrared or infrared rays, especially, dependency to rays having a wavelength within a range from 800 nm to 1000 nm.

Therefore, the light-emitting elements in the reflective optical sensor preferably emit a light having a wavelength within the above range. Moreover, the LEDs forming the light-emitting unit preferably emit the lights having the same wavelength. From the viewpoint of the wavelength, usage of the LED array as the light-emitting unit is preferable because the LEDs emit the lights having the same wavelength on the processing basis.

If the wavelength sensitivities of N number of the light-receiving elements forming the light-receiving unit are different from each other, even if the light-receiving elements receive the same light reflected from the toner pattern, the outputs of the light-receiving elements differs from each other, which may cause an error in the calculation for the toner density. Therefore, it is preferable to use PDs having the same peak sensitivity wavelength as the light-receiving elements of the light-receiving unit. From the viewpoint of the peak sensitivity wavelength, usage of the PD array as the light-receiving unit is preferable because the PDs of the PD array have the same peak sensitivity wavelength on the processing basis.

From the viewpoint of efficiency in receiving the detection light emitted from the light-emitting unit by the light-receiving unit, it is preferable to substantially match the wavelength of the detection light emitted from the LEDs forming as the light-emitting unit with the peak sensitivity wavelength of the PDs forming the light-receiving unit in an accurate manner by several tens of nanometers.

A wavelength of a light emitted from a typical GaAs-based LED is about 950 nm. A peak sensitivity wavelength of a typical Si-based PD is 800 nm. In other words, a typical GaAs-based LED and a typical Si-based PD satisfy the above-described requirement. Therefore, typical GaAs-based LEDs and typical Si-based PDs are preferable as the light-emitting elements and the light-receiving elements.

It is possible to shift the wavelength band by adjusting the compositions or the structure of the LEDs and the PDs. Thus, the wavelength of the detection light emitted from the LEDs can be set substantially matched with the peak sensitivity wavelength of the PDs.

As described above, in the reflective optical sensor, the light-emitting elements of the light-emitting unit emit the spots of the detection light onto the supporting member or the toner pattern. If individual LEDs each integrally including a member having the lens function of collecting divergent light are used as the light-emitting elements, the LEDs form the spots of the detection light all alone. If an LED array that does not has the lens function of collecting the detection light is used as the light-emitting unit, it is necessary to add a light-emitting optical system that receives the detection light from the light-emitting elements and causes the detection light convergent to the surface of the supporting member and/or a light-receiving optical system that receives the light reflected from the surface of the supporting member and causes the reflected light convergent to the light-receiving elements. By the usage of the light-emitting optical system and/or the light-receiving optical system, the spots of the detection light can be formed.

Even if individual LEDs having the lens function of collecting the detection light are used as the light-emitting elements, it is allowable to add the light-emitting optical system and/or the light-receiving optical system to form the spots of the detection light in a more efficient manner.

Such an embodiment is described below.

Figure 18A:
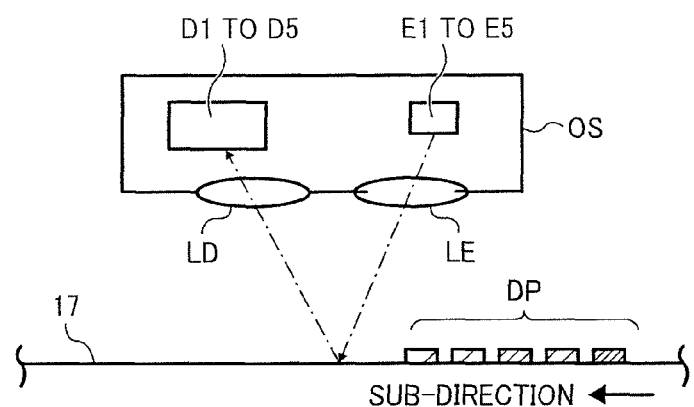
FIGS. 18A to 18C are schematic diagrams of a light-emitting optical system and a light-receiving optical system according to a first modification.
Figure 18B:
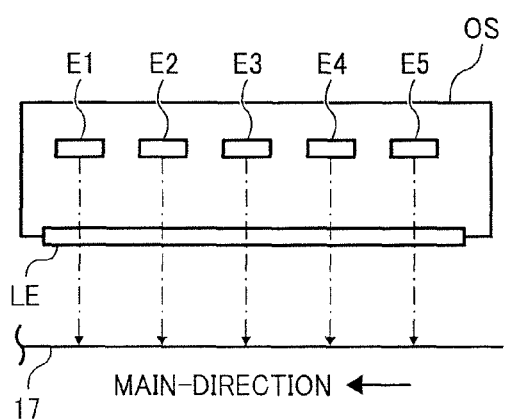

An embodiment is described with reference to FIGS. 18A to 18C. FIG. 18A is a schematic diagram of a reflective optical sensor OS according to the embodiment, viewed from the main-direction. The light-emitting unit includes five individual LEDs, as the light-emitting elements E1 to E5, aligned in the main-direction at an equal pitch. The light-receiving unit includes five individual PDs, as the light-receiving elements D1 to D5, aligned in the main-direction at an equal pitch. The LEDs as the light-emitting elements has the lens function of collecting the divergent light.

The reflective optical sensor OS includes a light-emitting optical system LE and a light-receiving optical system LD. The light-emitting optical system LE and the light-receiving optical system LD can be, as shown in FIGS. 18A to 18C, cylindrical lenses. The cylindrical lenses have a positive power in the sub-direction. The supporting member 17 is, more particularly, the transfer belt. A toner pattern DP is used for the toner-density calculation.

The process of calculating the toner density is performed in the same manner as described above with reference to FIGS. 2 and 3.

When the light-emitting element (LED) Ei, where i is an arbitrary integer from 1 to 5, turns ON/OFF, the detection light is collected in the sub-direction by the light-emitting optical system LE, and the collected detection light illuminates the supporting member 17 or the toner pattern DP. The reflected light is collected in the sub-direction by the light-receiving optical system LD, and the collected reflected light is received by the light-receiving element Di.

The light-emitting optical system can be used to shape the detection light so that the spot having a desired shape is formed on the supporting member or the toner pattern. The light-receiving optical system can be used to shape the reflected light so that the spot having a desired shape is formed on the light-receiving elements. If the light-emitting optical system and the light-receiving optical system have the same structure, the costs for those optical systems can be suppressed. To make the drawings and the description simpler, only five light-emitting elements and five light-receiving elements are shown in FIGS. 18A to 18C.

Figure 18C:
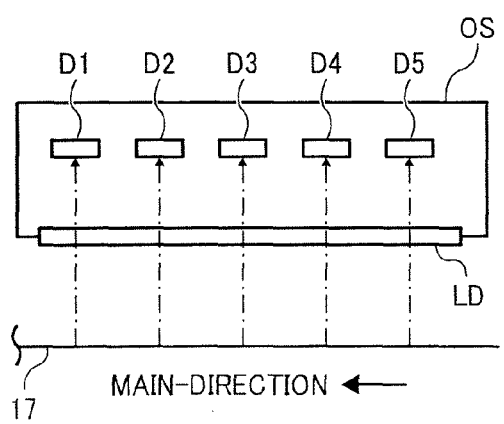
Figure 19A:
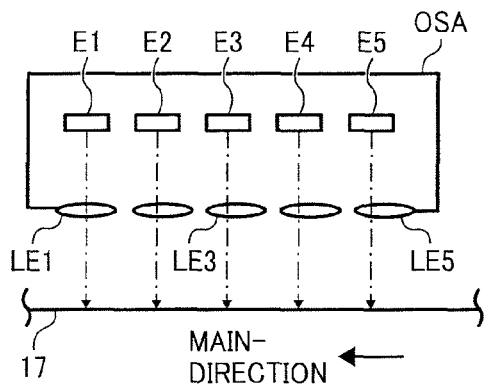
FIGS. 19A and 19B are schematic diagrams of a light-emitting optical system and a light-receiving optical system according to a second modification.
Figure 19B:
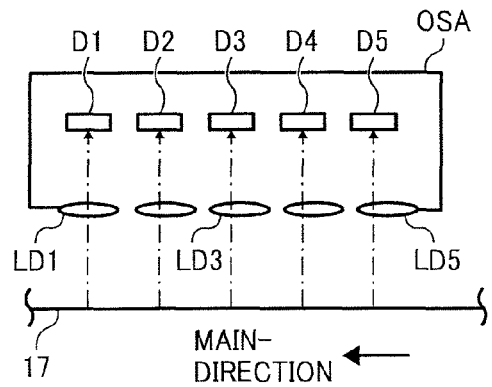

In the embodiment shown in FIGS. 19A and 19B, a reflective optical sensor OSA shown in FIG. 19A includes the light-emitting optical system and the light-receiving optical system. The light-emitting optical system includes emission-light collecting lenses LE1 to LE5 in positions to receive the emission-light from five LEDs as the light-emitting elements E1 to E5, respectively. The detection-light collecting lenses LEi, where i is an arbitrary integer from 1 to 5, receives the emission light as divergent light from the corresponding light-emitting element Ei, and collects the light. Thus, the efficiency in illumination to the supporting member 17 increases. As compared to the cylindrical lens that is used as the light-emitting optical system shown in FIGS. 18A to 18C, if lenses having the light-gathering power in the main-direction are used, the efficiency in the illumination increases more. Anamorphic lenses having a power in the main-direction different from a power in the sub-direction can be used as the detection-light collecting lens LEi, where i is an arbitrary integer from 1 to 5.

It is allowable to use the light-emitting optical system, which is shown in FIG. 19A, formed with the anamorphic lens LEi corresponding to the light-emitting element Ei in the one-to-one manner, and the light-receiving optical system, which is shown in FIG. 18C, formed with the cylindrical lenses having only a power in the sub-direction. A user can select a combination of a type of the light-emitting optical system and a type of the light-receiving optical system as appropriately, taking into consideration desired illumination efficiency, a shape of the spots of the detection light, desired light-receiving efficiency, and a shape of the spots on the light-receiving elements. To make the drawings and the description simpler, only five light-emitting elements and five light-receiving elements are shown in FIGS. 19A and 19B.

Figure 20A:
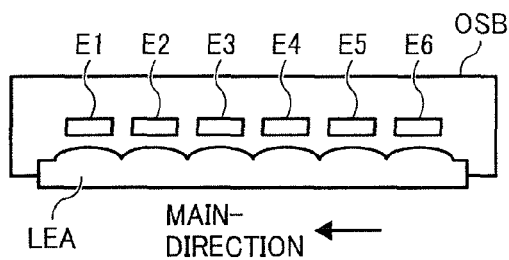
FIGS. 20A and 20B are schematic diagrams of a light-emitting optical system and a light-receiving optical system according to a third modification.
Figure 20B:
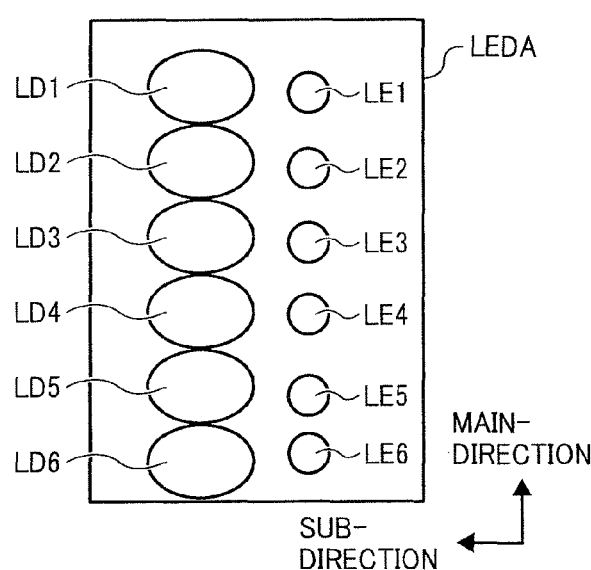

Two additional embodiments are shown in FIGS. 20A and 20B.

In the embodiment shown in FIG. 20A, a reflective optical sensor OSB includes the light-emitting unit and a light-emitting optical system LEA. The light-emitting unit includes six LEDs as the light-emitting elements E1 to E6. The light-emitting optical system LEA includes convex lenses integrally arranged on a surface. The convex lenses are in positions to receive the detection light from the light-emitting elements E1 to E6, respectively and collect the received detection light.

Although, in the light-emitting optical system LEA, the surface facing the LEDs can collect the light, the opposite surface is flat, i.e., cannot collect the light. However, it is allowable to use surfaces that can collect the light on the both sides. Because the light-emitting optical system LEA is integrally formed, as compared to attaching individual lenses corresponding to the light-emitting elements, the light-emitting optical system LEA is easy to attach and has an advantage in the arrangement accuracy among the lens surfaces.

Although not shown in FIG. 20A, it is possible to use a collection of integrally-formed light-receiving lenses as the light-receiving optical system in the same manner as the light-emitting optical system.

In the embodiment shown in FIG. 20B, a light-emitting/light-receiving optical system LEDA includes six collecting lenses LE1 to LE6 as the light-emitting optical system and six collecting lenses LD1 to LD6 as the light-receiving optical system as a unit. Relative positions among those components are fixed, as appropriately.

Usage of the light-emitting/light-receiving optical system LEDA makes it possible to increase the accuracy in arrangement of the collecting lenses for the light-emitting optical system and the collecting lenses for the light-receiving optical system. Those collecting lenses can be formed on a substrate made of, for example, glass or resin at the positions as shown in FIGS. 20A and 20B by the photolithography or the nanoimprint technology. To make the drawings and the description simpler, six light-emitting elements and six light-receiving elements are shown in FIGS. 20A and 20B.

If, for example, the light-emitting elements and the light-receiving elements are aligned as shown in FIGS. 14A, 14B, 16A, 16B, or FIG. 3, the arrangements of the light-emitting optical system and the light-receiving optical system are changed as appropriately based on the arrangements of the light-emitting elements and the light-receiving elements.

If the light-emitting optical system and the light-receiving optical system are lens arrays or lens-surface arrays, the pitch of the lenses or the lens surfaces is preferably set equal.

A light-emitting optical system and a light-receiving optical system according to another embodiment are described below.

Figure 21:
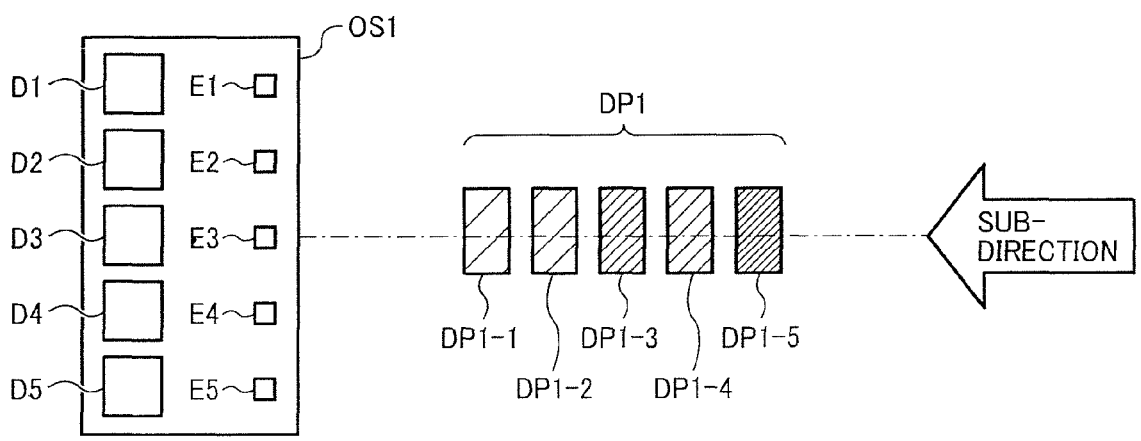
FIG. 21 is a schematic diagram of a light-emitting optical system and a light-receiving optical system according to a fourth modification.

FIG. 21 is a schematic diagram of a modification of the example shown in FIG. 3A. The same reference numerals indicate the same components shown in FIG. 3A. The following description is made with reference to this example.

In the example shown in FIG. 21, the up-and-down direction corresponds to the "main-direction"; the side-to-side direction corresponds to the "sub-direction". The reflective optical sensor OS1 includes the light-emitting unit that includes the light-emitting elements E1 to E5 (M=5), each emits the detection light, arranged at a predetermined equal pitch in the main-direction.

The reflective optical sensor OS1 includes the light-receiving unit that includes the light-receiving elements D1 to D5 (N=5), each receives light reflected, arranged in a predetermined equal pitch in the main-scanning direction. The light-emitting unit and the light-receiving unit are arranged in a corresponding manner in an appropriate housing as a unit.

The housing is arranged "under the transfer belt 17" inside of the image forming apparatus shown in FIG. 1.

The positions of the light-emitting elements E1 to E5 that together form the light-emitting unit are "the same in the main-direction" as the positions of the light-receiving elements D1 to D5 that together form the light-receiving unit, respectively. The pitch of the light-receiving elements D1 to D5 is equal to the pitch of the light-emitting elements E1 to E5.

It is assumed that the surface of the transfer belt 17 (shown in FIG. 1), on which the toner pattern is formed, is specular. When an arbitrary light-emitting element illuminates the surface of the transfer belt with the detection light, "light specularly reflected by the surface of the transfer belt" is received at three light-receiving elements that include the corresponding light-receiving element and two light-receiving elements that are adjacent to the corresponding light-receiving element.

Accordingly, if the light-emitting element E3 turns ON, detection light specularly reflected by the transfer belt is received at the light-receiving element D3, which is the one corresponding to the light-emitting element E3, and "the light-receiving elements D2 and D4 that are adjacent to the light-receiving element D3", while no light is received at the light-receiving elements D1 and D5.

Accordingly, in this situation, outputs from the light-receiving elements D2, D3, and D4 are larger than zero, while outputs from the two light-receiving elements D1 and D5 are zero.

As described above, the light-emitting elements E1 to E5 are, for example, LEDs; the light-receiving elements D1 to D5 are, for example, PDs.

The pitch of the light-emitting elements E1 to E5 is set in such a manner that, when five spots of the detection light emitted from the individual light-emitting elements are formed on the surface of the transfer belt 17 "aligned in the main-scanning direction", the distance between adjacent spots is set smaller than the "length in the main-direction" of the toner pattern DP1.

As described above, the toner patterns DP1 to DP4 (see FIG. 2), which are necessary for the toner-density calculation, are formed with yellow, magenta, cyan, and black toners, respectively. The toner pattern DP1 shown in FIG. 21 is formed with the "yellow toner".

The toner pattern DP1 includes various rectangular patterns (five patterns in FIG. 21) having different gradated densities arranged in a single line running in the sub-direction.

In other words, the toner pattern DP1 is a collection of the five "rectangular toner patterns" having different toner densities. Those rectangular toner patterns having different toner densities are formed by "adjusting a laser power in the main-scanning or a duty in the emission light", or by "adjusting a developing bias". It is also allowable to form the toner patterns having different toner densities using pulse-surface-area modulation.

The individual five "rectangular toner patterns" that together form the toner pattern DP1 are called patterns DP1-1, DP1-2, DP1-3, DP1-4, and DP1-5. The patterns DP1-1, DP1-2, DP1-3, DP1-4, and DP1-5 are arranged in this order with the pattern DP1-1 being the most-downstream. The toner density increases from the pattern DP1-1 to the pattern DP1-5.

The toner pattern DP1 on the surface of the transfer belt, i.e., the supporting member moves in the sub-direction toward the detection area of the reflective optical sensor OS1.

The toner pattern DP1 is formed at a predetermined point of time. After the toner pattern DP1 is formed, the light-emitting elements (LEDs) E1 to E5 turn ON/OFF when the toner pattern DP1 moves close enough to the detection area.

The size of the spots of the detection light emitted from the light-emitting elements E1 to E5 formed on the surface of the transfer belt is set smaller than the pitch (0.4 mm in this example) of the light-emitting elements E1 to E5 (e.g., 0.2 mm) so that the five spots are aligned on the transfer belt in the main-direction.

The main-directional length of the "rectangular toner patterns DP1-1 to DP1-5" that together form the toner pattern DP1 is set larger than the pitch (0.4 mm) of the light-emitting elements E1 to E5 (e.g., 0.5 mm).

The main-directional distance between the adjacent spots (area between spots where no light strikes) is 0.1 mm, which is smaller than the length of the rectangular toner pattern in the main-direction (0.5 mm).

The light-emitting elements turn ON and OFF "in sequence from the light-emitting element E1 to the light-emitting element E5".

More particularly, the light-emitting element E1 turns ON and OFF, first. Secondly, the light-emitting element E2 turns ON and OFF. Then, the light-emitting elements E3, E4, and E5 turn ON and OFF in sequence.

The ON/OFF operation of the light-emitting elements E1 to E5 is repeated at a high speed.

In this manner, the surface of the transfer belt with the toner pattern DP1 formed thereon is scanned in the main-direction over and over with the five spots of the detection light (spot-scanning with the detection light).

Because the surface of the transfer belt is specular, when the detection light strikes the "area out of the toner pattern on the surface of the transfer belt", the reflected light is specularly reflected light.

When the light-emitting element Ei illuminates the surface of the transfer belt with the detection light, "light specularly reflected by the surface of the transfer belt" is received at only three light-receiving elements that include the corresponding light-receiving element Di and the two light-receiving elements Di-1 and Di+1 that are adjacent to the light-receiving element Di (light-receiving elements not corresponding to the light-emitting element Ei).

Figure 22A:
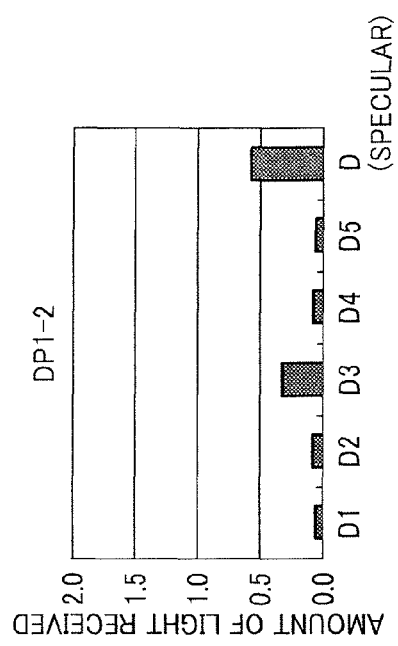
FIGS. 22A to 22F are graphs that illustrate the fourth modification shown in FIG. 21.

FIG. 22A is a graph of the "output from the individual light-receiving elements" due to light specularly reflected by the transfer belt observed when the light-emitting element E3 emits the detection light.

The horizontal axis of FIG. 22A is the light-receiving elements D1 to D5; the vertical axis of FIG. 22A is the magnitude of the outputs (amount of the light received). Because the specularly reflected light is received at only the light-receiving elements D2 to D4, the outputs from the light-receiving elements D1 and D5 are zero. "D (All)" in the horizontal axis is the sum of the outputs from the five light-receiving elements D1 to D5. The amount of light received in the vertical axis is normalized with the amount of light received at the light-receiving element D3 observed in the above-described situation being set to "1".

Suppose, for example, with the above-described configuration there is a case where the "center of the toner pattern DP1 in the main-direction" is on the spot of the detection light coming from the light-emitting element E3.

If the toner pattern is out of the detection area, the detection light emitted from the light-emitting element E1 is specularly reflected by the surface of the transfer belt and the specularly reflected light is received at the light-receiving element D1 and the light-receiving element D2 that is adjacent to the light-receiving element D1.

If the light-emitting element E1 turns ON and OFF solely, the output from the corresponding light-receiving element D1 is "substantially equal to the output from the light-receiving element D3 shown in FIG. 22A" and the output from the light-receiving element D2 is "substantially equal to the output from the light-receiving element D4 shown in FIG. 22A".

The detection light emitted from the light-emitting element E2 is specularly reflected by the surface of the transfer belt and the specularly reflected light is received at the light-receiving elements D1, D2, and D3.

The detection light emitted from the light-emitting element E4 is specularly reflected by the surface of the transfer belt and the specularly reflected light is received at the light-receiving elements D3, D4, and D5.

The detection light emitted from the light-emitting element E5 is specularly reflected by the surface of the transfer belt and the specularly reflected light is received at the light-receiving elements D4 and D5.

If the light-emitting element E2 turns ON solely, the output from the corresponding light-receiving element D2 is "substantially equal to the output from the light-receiving element D3 shown in FIG. 22A"; the output from the light-receiving element D1 is "substantially equal to the output from the light-receiving element D2 shown in FIG. 22A"; and the output from the light-receiving element D3 is "substantially equal to the output from the light-receiving element D4 shown in FIG. 22A".

If the light-emitting element E4 turns ON and OFF solely, the output from the corresponding light-receiving element D4 is "substantially equal to the output from the light-receiving element D3 shown in FIG. 22A"; the output from the light-receiving element D3 is "substantially equal to the output from the light-receiving element D2 shown in FIG. 22A"; and the output from the light-receiving element D5 is "substantially equal to the output from the light-receiving element D4 shown in FIG. 22A".

If the light-emitting element E5 turns ON and OFF solely, the output from the corresponding light-receiving element D5 is "substantially equal to the output from the light-receiving element D3 shown in FIG. 22A"; and the output from the light-receiving element D4 is "substantially equal to the output from the light-receiving element D2 shown in FIG. 22A".

If, in contrast, the light-emitting element E3 turns ON when the toner pattern is within the detection area and, therefore, the detection light strikes the toner pattern DP1, the detection light is "specularly and diffusely reflected" by the toner pattern DP1.

The distributions of the outputs from the light-receiving elements D1 to D5 in the above situation are shown in FIGS. 22B to 22F.

Figure 22B:
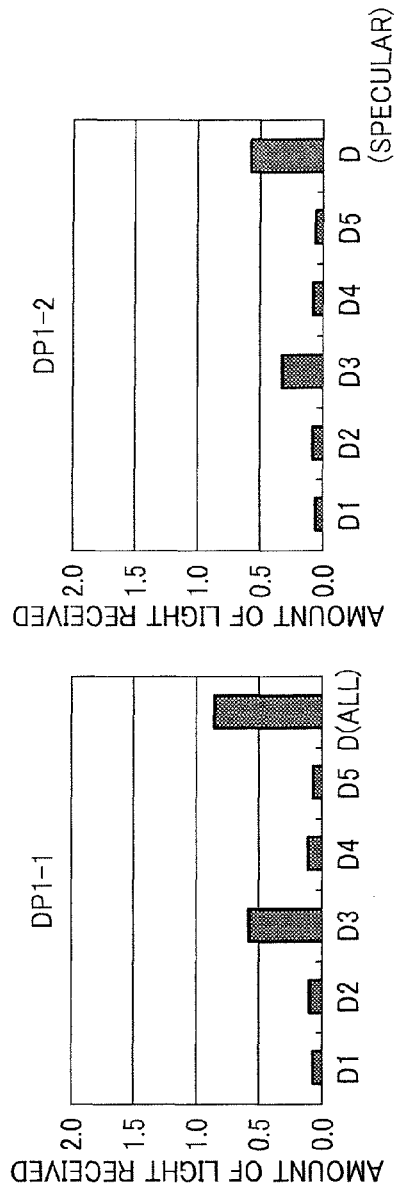
Figure 22C:
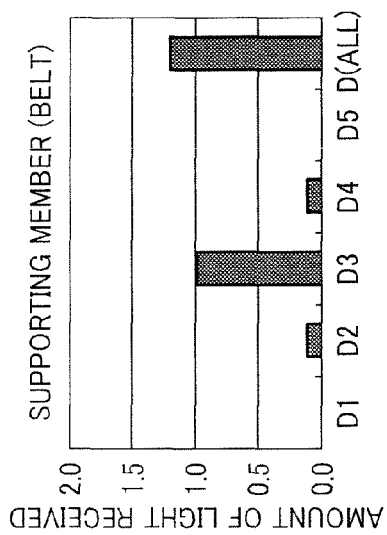
Figure 22D:
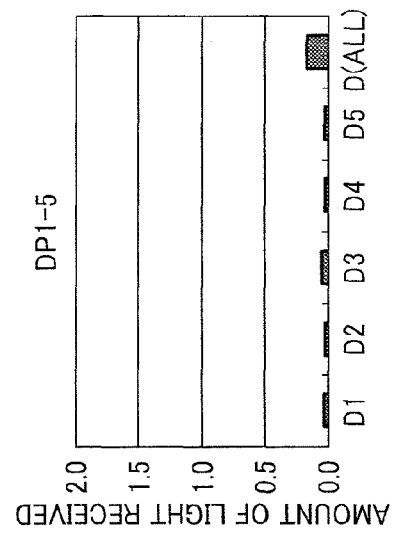
Figure 22E:
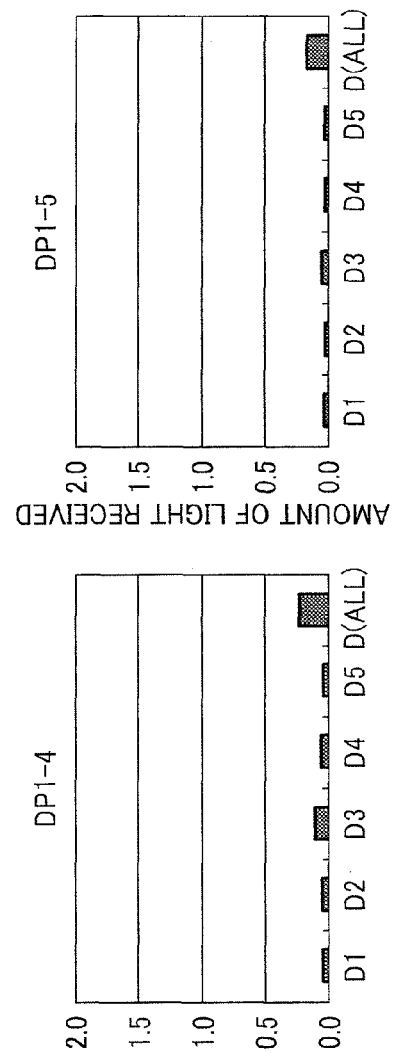
Figure 22F:
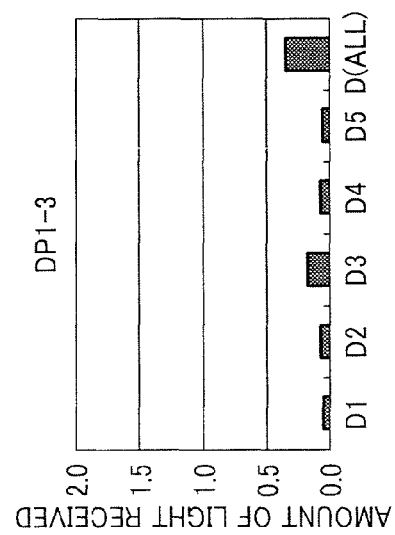

FIG. 22B is a graph of the output distribution observed when the rectangular toner pattern DP1-1 is exposed to the detection light; FIGS. 22C to 22F are graphs of the output distributions observed when the rectangular toner patterns DP1-2 to DP1-5 are exposed to the detection light, respectively.

The output from the light-receiving element D3 is inversely proportional to the toner density of the rectangular toner pattern.

The manner of calculating the toner density of, for example, the rectangular toner pattern DP1-1 is described below.

If the light-emitting element E3 turns ON when no toner pattern is formed on the transfer belt and, therefore, the detection light strikes the surface of the transfer belt, as for the outputs from the five light-receiving elements D1 to D5 due to "light reflected by the surface of the transfer belt", the outputs from the three light-receiving elements D2 to D4 are larger than zero, while the outputs from the light-receiving elements D1 and D5 are zero (see FIG. 22A).

If the light-emitting element E3 turns ON when the toner pattern is formed on the transfer belt and the detection light strikes the rectangular toner pattern DP1-1, the detection light is specularly and diffusely reflected by the toner pattern.

Because the light-receiving element D3 receives "only light specularly reflected", the output is completely due to specularly reflected light. In contrast, the output from each of the four light-receiving elements D1, D2, D4, and D5 other than the light-receiving element D3 is partially or completely "due to diffusely reflected light".

It is noted that the outputs from the two light receiving elements D1 and D5 are "completely due to diffusely reflected light". This is induced from the result that, when the detection light strikes the transfer belt, light specularly reflected by the transfer belt is received at only the light-receiving elements D2 to D4.

In contrast, when the light-emitting element E3 emits the detection light, the outputs from the two light-receiving elements D2 and D4 are "due to both light specularly reflected by the toner pattern and light diffusely reflected by the toner pattern".

How to calculate "the ratio between the amount of specularly reflected light and the amount of diffusely reflected light" is described below.

FIG. 22B is a graph of the output distribution observed when the detection light strikes the rectangular toner pattern DP1-1. These outputs are "due to both specularly reflected light and diffusely reflected light".

The outputs that are observed when the detection light strikes the supporting member, i.e., the transfer belt are completely due to specularly reflected light and the distribution of these outputs has already been shown in FIG. 22A.

The "amount of specularly reflected light" is calculated by multiplying the output distribution shown in FIG. 22A by a constant and subtracting the multiplied output distribution from the output distribution shown in FIG. 22B. If the constant is set to "α1", then α1 is calculated as follows.

Because, when the detection light from the light-emitting element E3 strikes the rectangular toner pattern DP1-1, the output from the light-receiving element D3 is completely due to specularly reflected light, the constant α1 is set in such a manner that the output from the light-receiving element D3 shown in FIG. 22B is set equal to "the output from the light-receiving element D3 shown in FIG. 22A multiplied by the constant".

Figure 23A:
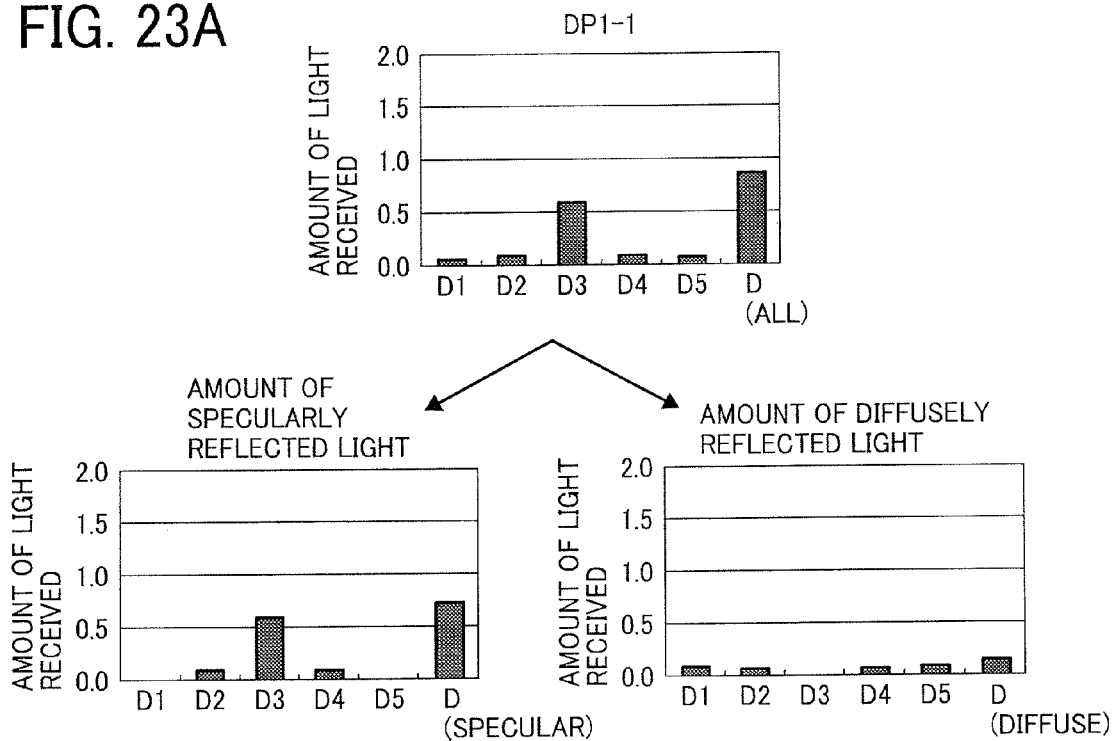
FIG. 23A is graphs that illustrate the fourth modification shown in FIG. 21.
Figure 23B:
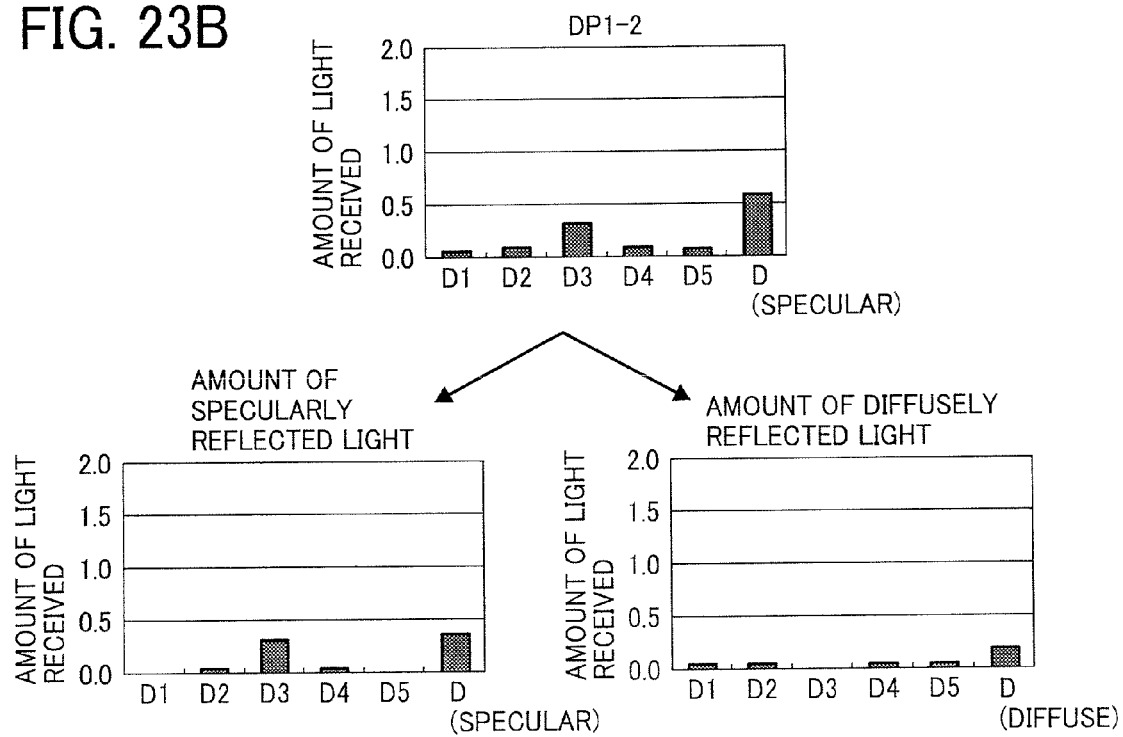
FIG. 23B is graphs that illustrate the fourth modification shown in FIG. 21.
Figure 23C:
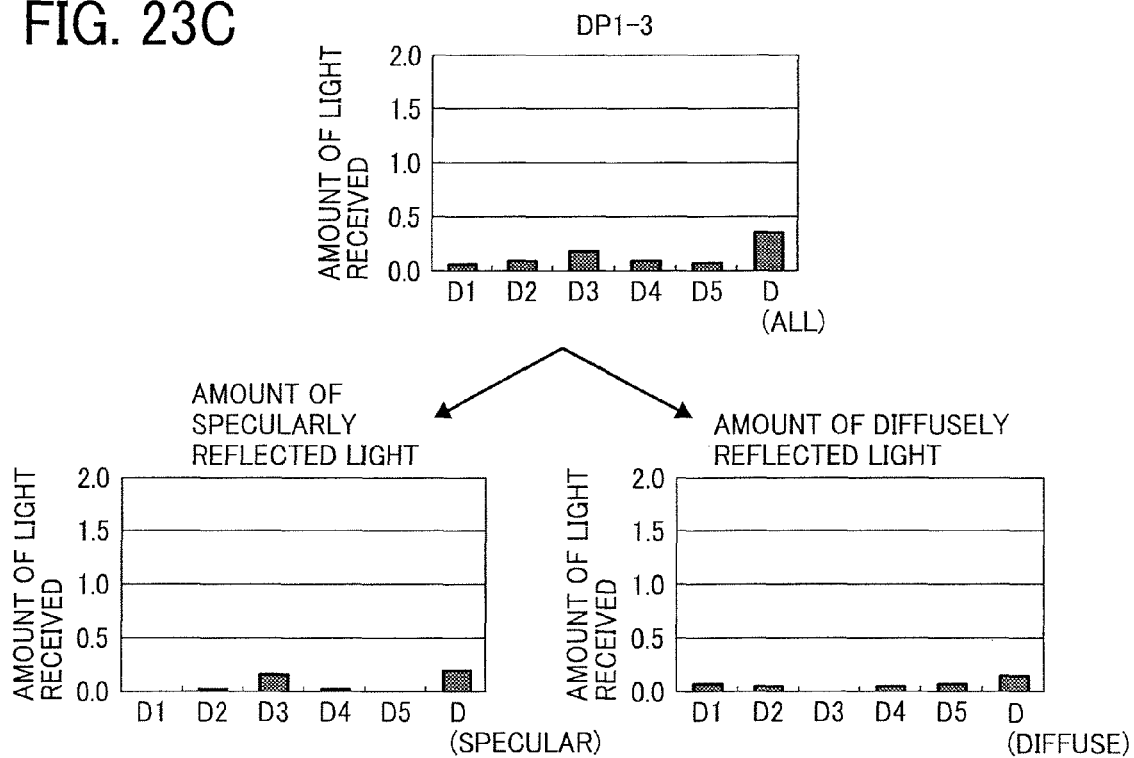
FIG. 23C is graphs that illustrate the fourth modification shown in FIG. 21.
Figure 23D:
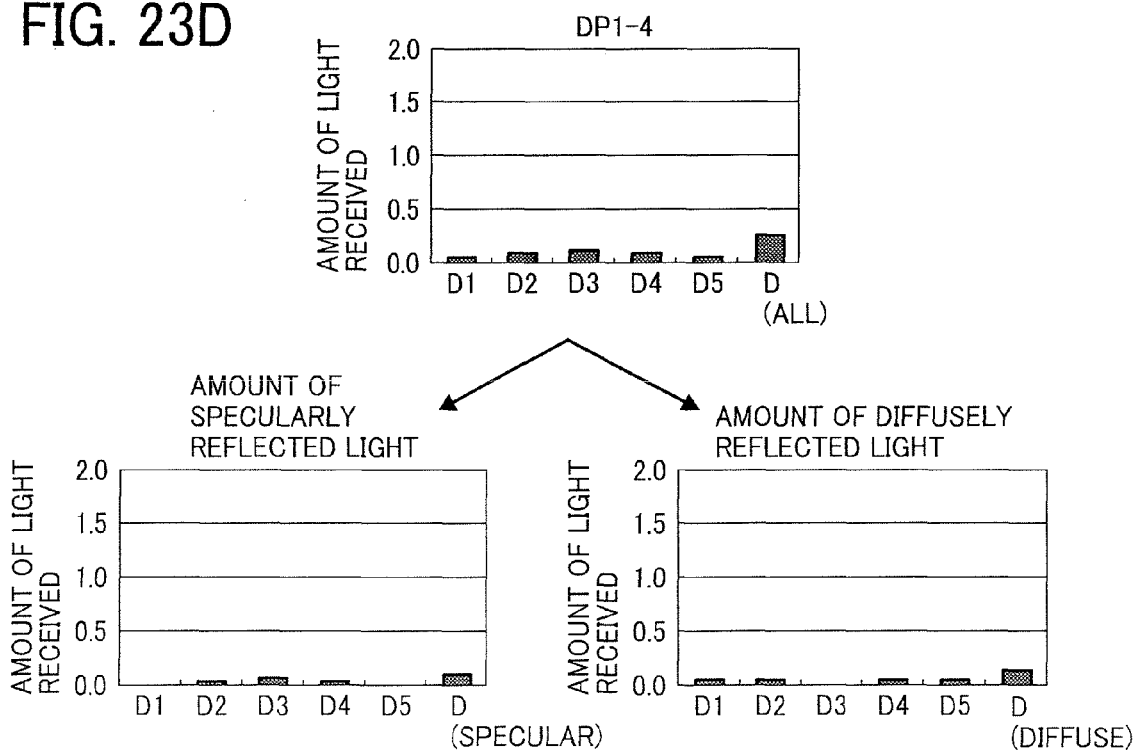
FIG. 23D is graphs that illustrate the fourth modification shown in FIG. 21.
Figure 23E:
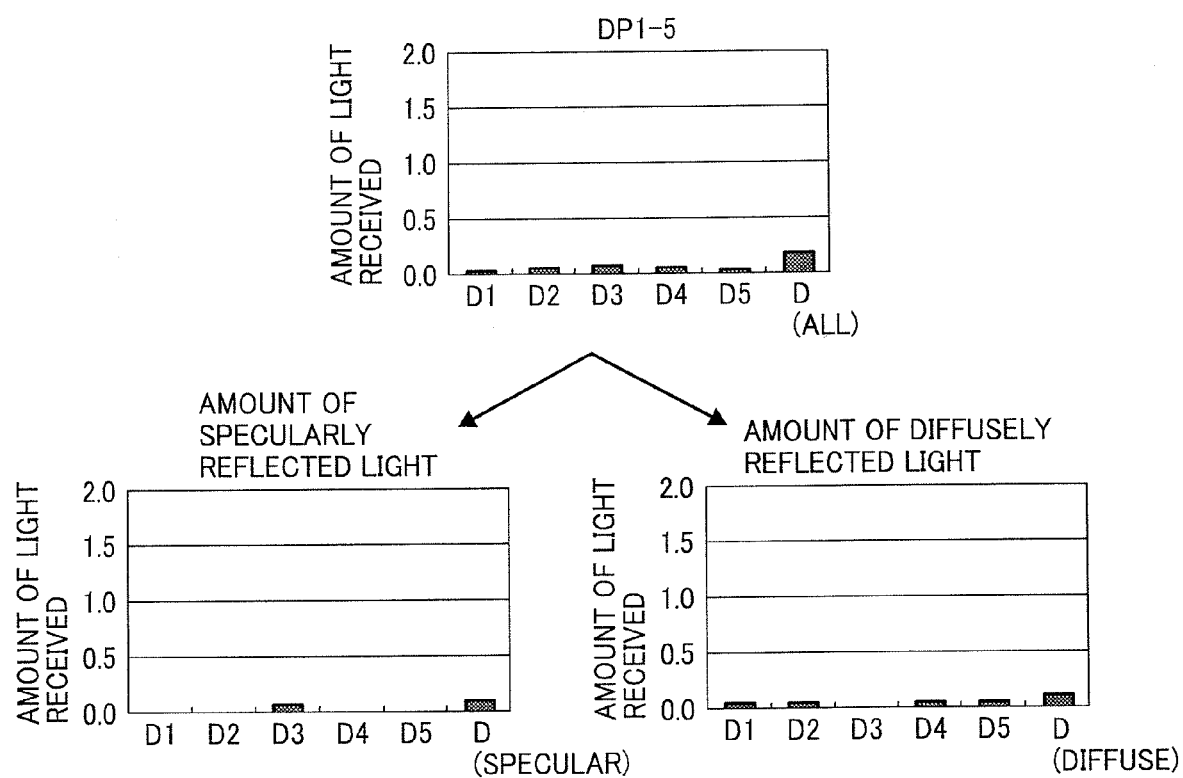
FIG. 23E is graphs that illustrate the fourth modification shown in FIG. 21.

In this manner, as shown in FIG. 23A, by using the "multiplied amount of specularly reflected light" that is calculated by multiplying the output distribution shown in FIG. 22A by the constant α1 and the output distribution shown in FIG. 22B, the "multiplied amount of specularly reflected light that is calculated by multiplying the output distribution shown in FIG. 22A by the constant α1" and the "amount of diffusely reflected light" are separated from each other.

If the output from the light-receiving element D3 shown in FIG. 22A is assumed to "A" and the output from the light-receiving element D3 shown in FIG. 22B is assumed to "A1", then "A" is completely due to specularly reflected light and "A1" is smaller than A by an amount of light received that is diffusely reflected by the rectangular toner pattern DP1-1.

If $\alpha 1 \cdot A = A1$, then the amount of diffusely reflected light is $A - \alpha 1 \cdot A = (1 - \alpha 1)A$.

Therefore, when the rectangular toner pattern DP1-1 is exposed to the detection light coming from the light-emitting element E3, the amount of specularly reflected light is "A1", i.e., "α1·A" and the amount of diffusely reflected light is "(1−α1)A". In this manner, the amount of specularly reflected light and the amount of diffusely reflected light are separated from each other.

As for the cases shown in FIGS. 22C to 22F where the rectangular toner patterns DP1-2 to DP1-5 having the different toner densities are exposed to the detection light coming from the light-emitting element E3, the amount of specularly reflected light and the amount of diffusely reflected light are separated from each other as shown in FIGS. 23B to 23E, respectively. The constants used in the cases shown in FIGS. 22C to 22F are assumed to α2 to α5, respectively.

Figure 24A:
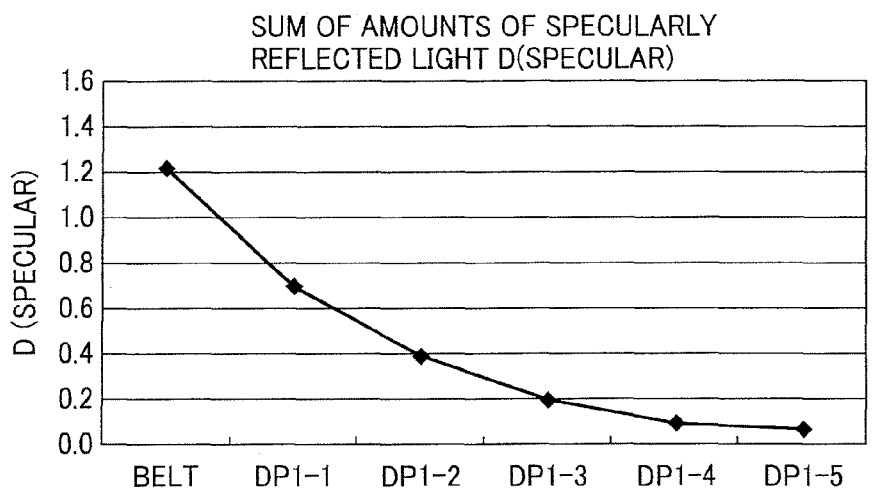
FIGS. 24A and 24B are graphs that explain the fourth modification shown in FIG. 21.
Figure 24B:
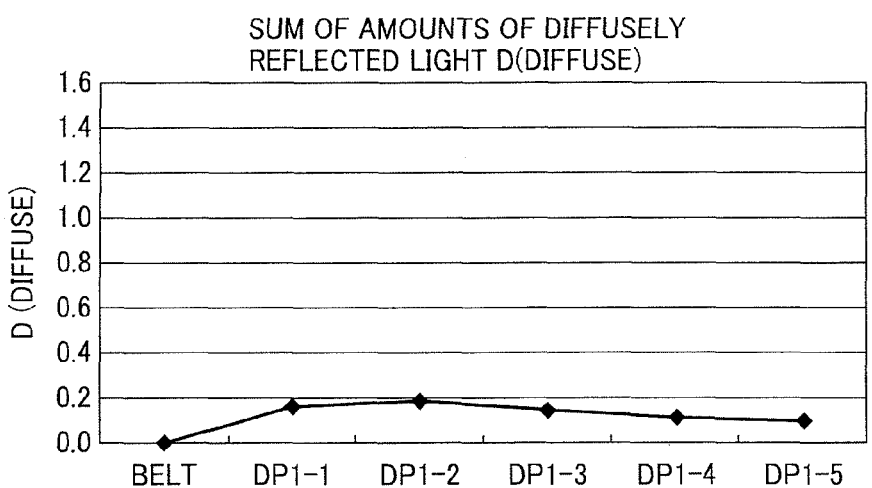

It is assumed that Di is the output from the light-receiving element Di and D(ALL) is the sum of the outputs from the light-receiving elements Di (i=1 to 5), i.e., D(All)=D1+D2+D3+D4+D5. D(All) is calculated independently with the different rectangular toner patterns DP1-1 to DP1-5. FIG. 24A is a graph of D(ALL) due to specularly reflected light; and FIG. 24B is a graph of D(ALL) due to diffusely reflected light.

As for the amount of specularly reflected light, because the outputs from the light-receiving elements D1 and D5 are zero, D(ALL)=D(specular)=D3+(the amounts of specularly reflected light extracted from D2 and D4). As for the amount of diffusely reflected light, because D3 is zero, D(ALL)ED (diffuse)=D1+(the amounts of diffusely reflected light extracted from D2 and D4)+D5.

It is clear from FIG. 24A that D(specular), which is the sum of the amounts of specularly reflected light, decreases from the rectangular toner patterns DP1-1 to DP1-5, as the toner density increases.

This is because an amount of specularly reflected light decreases as the amount of attached toner, i.e., the toner density increases. The relation between the toner density and D(specular) is one-to-one.

In other words, the toner density is calculated in accordance with the calculation result of D(specular).

It is clear from FIG. 24B, in contrast, that D(diffuse), which is the sum of the amounts of diffusely reflected light, is at its peak at the rectangular toner pattern DP1-2. That is, D(diffuse) is not a "monotonic function".

It is possible but not easy to obtain the relation between the toner density and D(diffuse) from D(diffuse) shown in FIG. 24B.

Although it seems to be apparent that "the amount of the diffusely reflected light is proportional to the toner density, i.e., the amount of attached toner", the graph shown in FIG. 24B does not support the assumption.

This is because of the calculation manner using the above-described constants $\alpha 1$ to $\alpha 5$.

Figure 25:
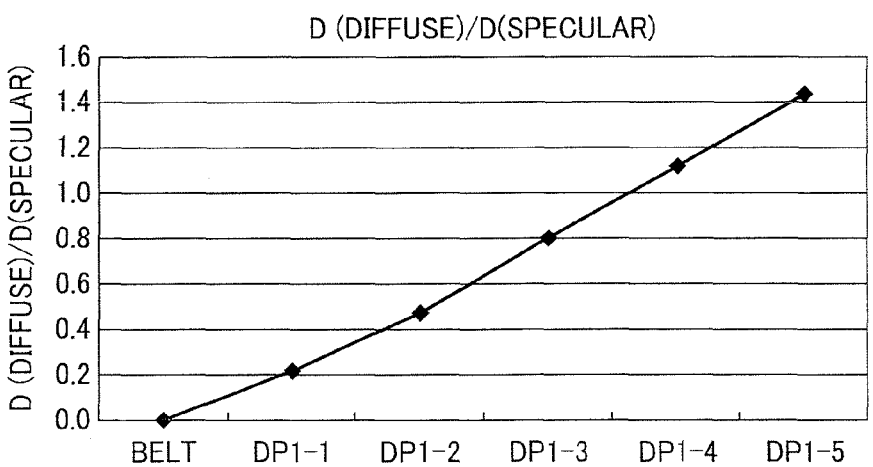
FIG. 25 is a graph that explains the fourth modification shown in FIG. 21.

FIG. 25 is a graph of D(diffuse)/D(specular).

It is clear from FIG. 25 that D(diffuse)/D(specular) in the vertical axis increases from the rectangular toner pattern DP1-1 to the rectangular toner pattern DP1-5. That is, D(diffuse)/D(specular) is the "simple function for the toner density". Accordingly, it is possible to calculate the toner density of each rectangular toner pattern (in the horizontal axis of FIG. 25) using "D(diffuse)/D(specular)".

Figure 26A:
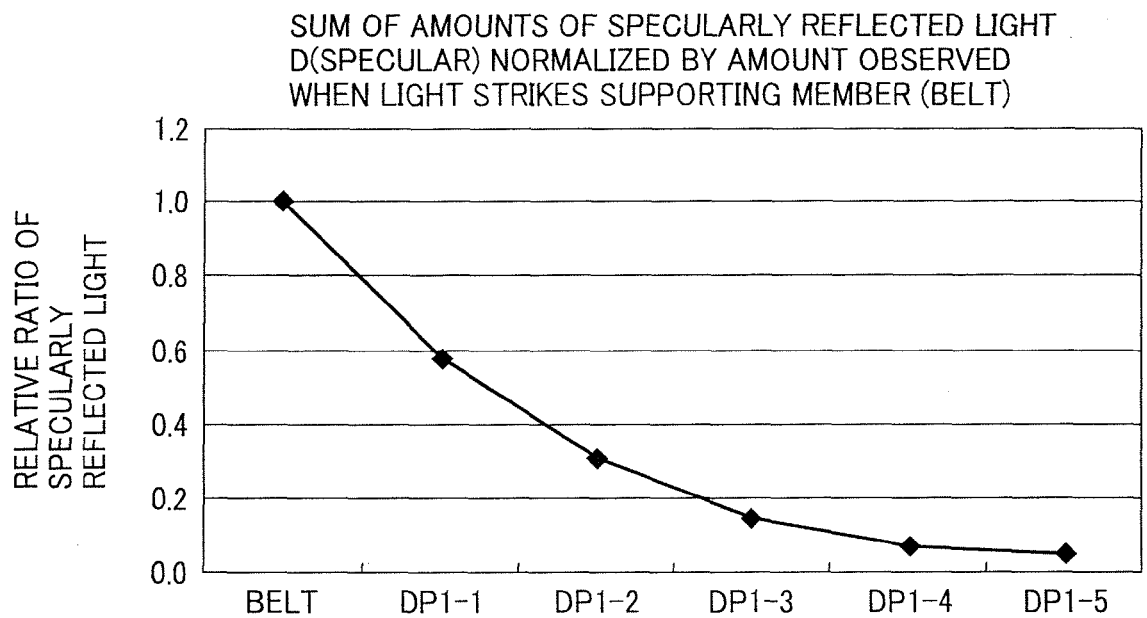
FIGS. 26A and 26B are graphs that illustrate the fourth modification shown in FIG. 21.

FIG. 26A shows the "relative ratio of specularly reflected light" that is calculated by normalizing the amount of specularly reflected light shown in FIG. 24A with the referential value (the amount of light specularly reflected by the surface of the transfer belt, in this example).

Figure 26B:
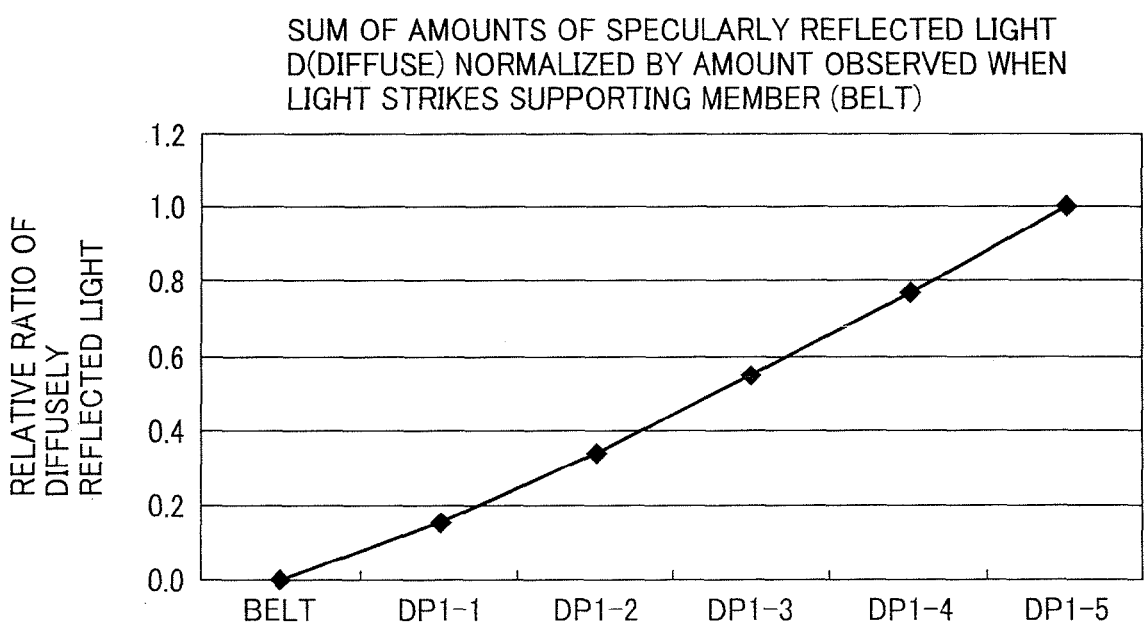

FIG. 26B shows the "relative ratio of diffusely reflected light" that is calculated by normalizing D(diffuse)/D(specular) with the referential value (the amount of diffusely reflected light at the highest toner density, in this example).

In this manner, it is allowable to calculate the toner density using D(diffuse)/D(specular), which is the ratio calculated by dividing D(diffuse), indicative of the amount of diffusely reflected light, by D(specular), indicative of the amount of specularly reflected light.

Although, in the above example, only five light-emitting elements E1 to E5 and five light-receiving elements D1 to D5 are used to make the description simpler, the numbers of the light-emitting elements and the light-receiving elements can be more than or less than five. If it is required to "detect the toner pattern accurately in the main-direction by the millimeter order", about 10 to about 30 light-emitting elements and light-receiving elements will be used.

Moreover, although "the transfer belt with the specular surface (light reflected by the surface is completely due to light specularly reflected)" is used in the above example, the above-described manner of thinking is applicable to an example using a "transfer belt with the non-specular surface (light reflected by the surface includes both specularly reflected light and diffusely reflected light)".

Only if "the distribution of the outputs due to light reflected by the specular material" is calculated in an appropriate manner, it is possible to "separate the amount of specularly reflected light and the amount of diffusely reflected light from each other" using the distribution.

For example, it is allowable to calculate the output distribution using the specular material and store the calculated distribution in a memory or the like. Alternatively, it is allowable to use a transfer belt with the surface "a part of which is specular" and calculate the amount of specularly reflected light using the specular part. Still alternatively, it is allowable to arrange a movable specular material inside the image forming apparatus and move the specular material to the position to calculate the amount of specularly reflected light, if required.

Figure 27:
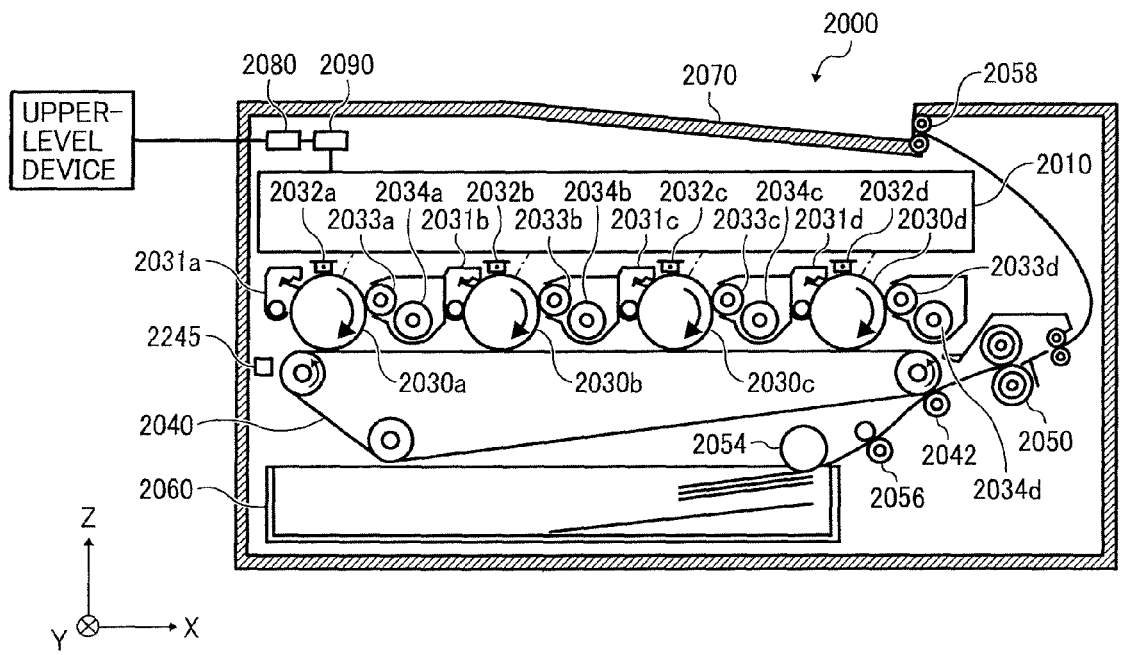
FIG. 27 is a schematic diagram of an inner configuration of a color printer according to a second embodiment.
Figure 28:
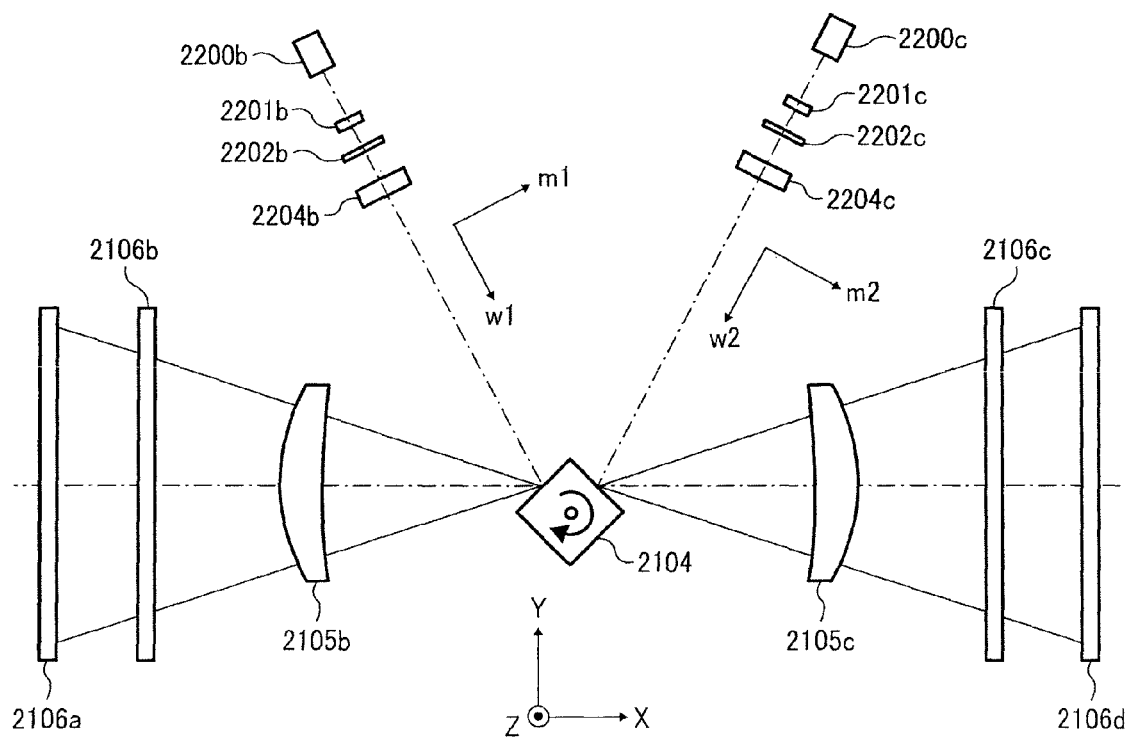
FIG. 28 is a first schematic diagram of the inner configuration of an optical scanning device shown in FIG. 27.
Figure 29:
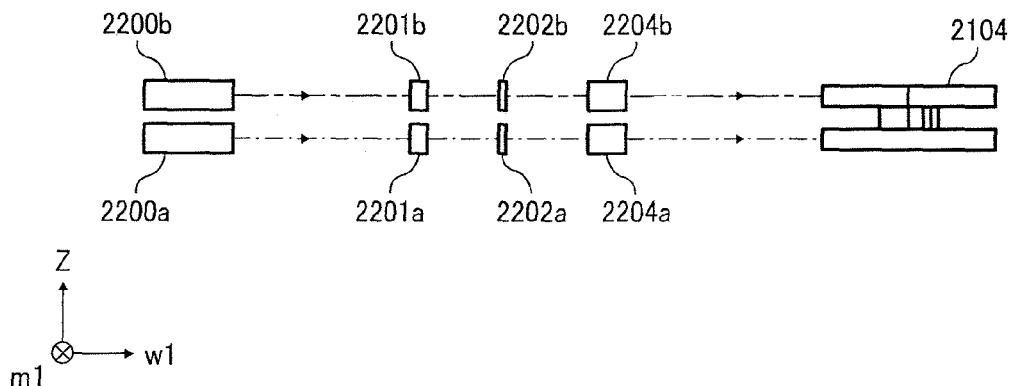
FIG. 29 is a second schematic diagram of the inner configuration of the optical scanning device.
Figure 30:
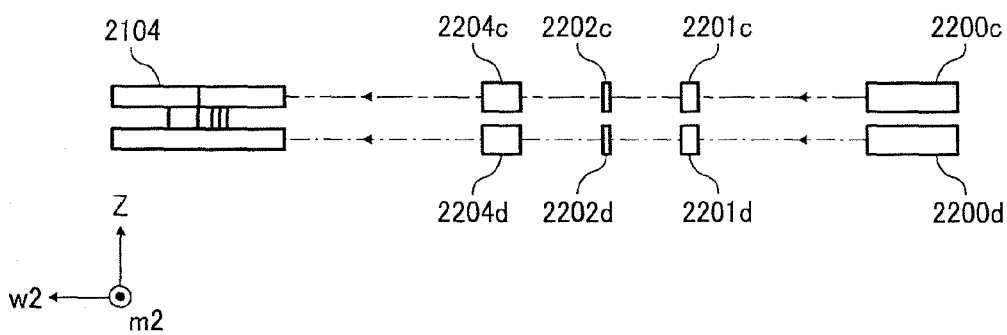
FIG. 30 is a third schematic diagram of the inner configuration of the optical scanning device.
Figure 31:
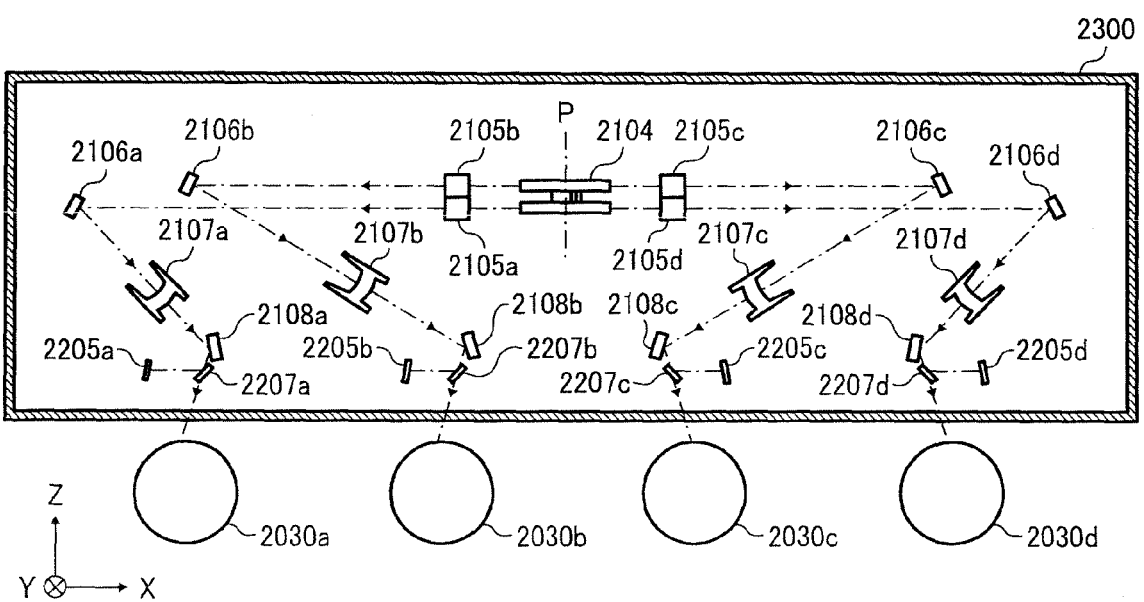
FIG. 31 is a fourth schematic diagram of the inner configuration of the optical scanning device.

A second embodiment is described below. FIG. 27 is a schematic diagram of the inner configuration of a color printer 2000 that corresponds to an image forming apparatus according to the second embodiment.

The color printer 2000 is a tandem-type multi-color printer that forms full-color images by superimposing four different colored (black, cyan, magenta, and yellow) images. The color printer 2000 includes an optical scanning device 2010, four drum-shaped photosensitive elements (2030*a*, 2030*b*, 2030*c*, and 2030*d*), four cleaning units (2031*a*, 2031*b*, 2031*c*, and 2031*d*), four charging devices (2032*a*, 2032*b*, 2032*c*, and 2032*d*), four developing rollers (2033*a*, 2033*b*, 2033*c*, and 2033*d*), four toner cartridge (2034*a*, 2034*b*, 2034*c*, and 2034*d*), a transfer belt 2040, a transfer roller 2042, a fixing roller 2050, a paper-feed roller 2054, a pair of registration rollers 2056, a paper-discharge roller 2058, a paper-feed tray 2060, a discharge tray 2070, a communication control device 2080, a toner-density calculator 2245, and a printer control device 2090 that controls the above-described components.

From the viewpoint of the XYZ 3-dimensional orthogonal coordinate system, it is assumed that the direction along the longitudinal axis of each photosensitive element corresponds to the Y-axis direction; the direction in which the four photosensitive elements are arranged corresponds to the X-axis direction.

The communication control device 2080 controls mutual communications between the color printer 2000 and a higher-level device (e.g., a personal computer) connected to the color printer 2000 via a network.

Each of the photosensitive elements has the surface with a photosensitive layer being formed thereon. It means that the surface of each photosensitive element is the surface to be scanned. Each photosensitive element is rotated by a rotating mechanism (not shown) in the direction indicated by the arrow shown in FIG. 27.

The charging device 2032*a*, the developing roller 2033*a*, and the cleaning unit 2031*a* are arranged along the rotating direction of the photosensitive element 2030*a* near the surface of the photosensitive element 2030*a*.

The photosensitive element 2030*a*, the charging device 2032*a*, the developing roller 2033*a*, the toner cartridge 2034*a*, and the cleaning unit 2031*a* together form an image forming station for black images (hereinafter, "K station") and they operate as a unit.

The charging device 2032*b*, the developing roller 2033*b*, and the cleaning unit 2031*b* are arranged along the rotating direction of the photosensitive element 2030*b* near the surface of the photosensitive element 2030*b*.

The photosensitive element 2030*b*, the charging device 2032*b*, the developing roller 2033*b*, the toner cartridge 2034*b*, and the cleaning unit 2031*b* together form an image forming station for cyan images (hereinafter, "C station") and they operate as a unit.

The charging device 2032*c*, the developing roller 2033*c*, and the cleaning unit 2031*c* are arranged along the rotating direction of the photosensitive element 2030*c* near the surface of the photosensitive element 2030*c*.

The photosensitive element 2030*c*, the charging device 2032*c*, the developing roller 2033*c*, the toner cartridge 2034*c*, and the cleaning unit 2031c together form an image forming station for magenta images (hereinafter, "M station") and they operate as a unit.

The charging device 2032d, the developing roller 2033d, and the cleaning unit 2031d are arranged along the rotating direction of the photosensitive element 2030d near the surface of the photosensitive element 2030d.

The photosensitive element 2030d, the charging device 2032d, the developing roller 2033d, the toner cartridge 2034c, and the cleaning unit 2031d together form an image forming station for yellow images (hereinafter, "Y station") and they operate as a unit.

Each of the charging devices evenly charges the surface of the corresponding photosensitive element.

The optical scanning device 2010 emits light, which is modulated appropriately depending on the corresponding-colored image data (black image data, cyan image data, magenta image data, or yellow image data) that is received from the higher-level device, to the charged surface of the corresponding photosensitive element. As a result of the scanning, part of the surface of the photosensitive element exposed to the light is discharged and, thus, a latent image is formed on the surface of the photosensitive element on the basis of the image data. The formed latent image moves toward the corresponding developing roller by rotation of the photosensitive element. The configuration of the optical scanning device 2010 will be described later.

The toner cartridge 2034a contains black toner and the black toner is supplied to the developing roller 2033a. The toner cartridge 2034b contains cyan toner and the cyan toner is supplied to the developing roller 2033b. The toner cartridge 2034c contains magenta toner and the magenta toner is supplied to the developing roller 2033c. The toner cartridge 2034d contains yellow toner and the yellow toner is supplied to the developing roller 2033d.

The toner, which is supplied from each toner cartridge, is evenly and thinly applied to the surface of the corresponding developing roller by rotation of the developing roller. When the toner on the surface of each developing roller comes in contact with the surface of the corresponding photosensitive element, the toner moves and attached only to the part exposed to the light. In other words, the latent image formed on the surface of each photosensitive element is developed to a visible image by operation of the corresponding developing roller. The visible image with toner (toner image) moves toward the transfer belt 2040 by rotation of the photosensitive element.

The yellow, magenta, cyan, and black toner images are transferred onto the transfer belt 2040 in sequence at predetermined different points of time in a superimposed manner and, thus, a color image is formed. It is noted that the direction on the transfer belt 2040 in which the toner image moves is called "the sub-direction"; and the direction perpendicular to the sub-direction (i.e., Y-axis direction, in this example) is called "the main-direction".

The paper-feed tray 2060 accommodates recording sheets. The paper-feed roller 2054 is arranged near the paper-feed tray 2060. The paper-feed roller 2054 feeds the recording sheets one by one from the paper-feed tray 2060 and conveys the recording sheet to the registration rollers 2056. The registration rollers 2056 convey the recording sheet to between the transfer belt 2040 and the transfer roller 2042 at a predetermined point of time. After the image is transferred onto the recording sheet, the recording sheet is conveyed to the fixing roller 2050.

Heat and pressure is applied to the recording sheet by operation of the fixing roller 2050 and, therefore, the toner is fixed onto the recording sheet. The recording sheet with the toner fixed thereon is conveyed to the discharge tray 2070 via the paper-discharge roller 2058 and then stacked on the discharge tray 2070.

Each of the cleaning units removes toner (residual toner) from the surface of the corresponding photosensitive element. After the residual toner is removed from the surface of the photosensitive element, the surface with no residual toner rotates to the position opposed to the corresponding charging device.

The toner-density calculator 2245 is arranged near the −X side of the transfer belt 2040. The toner-density calculator 2245 will be described in later.

The configuration of the optical scanning device 2010 is described below.

As shown in FIGS. 28 to 31 for example, the optical scanning device 2010 includes four light sources (2200a, 2200b, 2200c, and 2200d), four coupling lenses (2201a, 2201b, 2201c, and 2201d), four apertures (2202a, 2202b, 2202c, and 2202d), four cylindrical lenses (2204a, 2204b, 2204c, and 2204d), a polygon mirror 2104, four fθ lenses (2105a, 2105b, 2105c, and 2105d), eight reflecting mirrors (2106a, 2106b, 2106c, 2106d, 2108a, 2108b, 2108c, and 2108d), four toroidal lenses (2107a, 2107b, 2107c, and 2107d), four light detection sensors (2205a, 2205b, 2205c, and 2205d), four light detection mirrors (2207a, 2207b, 2207c, and 2207d), a scanning control device (not shown), etc. These components are fixed at predetermined positions inside an optical-system housing 2300 (not shown in FIGS. 28 to 30, see FIG. 31).

Hereinafter, the direction corresponding to the main-scanning direction is called "main-scanning corresponding direction" and the direction corresponding to the sub-scanning direction is called "sub-scanning corresponding direction".

Moreover, the direction along the optical axis of the coupling lenses 2201a and 2201b is called "direction w1", and the main-scanning corresponding direction at the light sources 2200a and 2200b is called "direction m1". Moreover, the direction along the optical axis of the coupling lenses 2201c and 2201d is called "direction w2", and the main-scanning corresponding direction at the light sources 2200c and 2200d is called "direction m2". The sub-scanning corresponding direction at the light sources 2200a and 2200b and the sub-scanning corresponding direction at the light sources 2200c and 2200d are the same as the Z-axis direction.

The light sources 2200b and 2200c are arranged spaced from each other in the X-axis direction. The light source 2200a is arranged −Z side of the light source 2200b. The light source 2200d is arranged −Z side of the light source 2200c.

The coupling lens 2201a is arranged on the optical path of light emitted from the light source 2200a. The light is converted to substantially parallel light when passed through the coupling lens 2201a.

The coupling lens 2201b is arranged on the optical path of light emitted from the light source 2200b. The light is converted to substantially parallel light when passed through the coupling lens 2201b.

The coupling lens 2201c is arranged on the optical path of light emitted from the light source 2200c. The light is converted to substantially parallel light when passed through the coupling lens 2201c.

The coupling lens 2201d is arranged on the optical path of light emitted from the light source 2200d. The light is converted to substantially parallel light when passed through the coupling lens 2201d.

The aperture 2202a has an opening. When the light after passed through the coupling lens 2201a further passes through the aperture 2202a, the light is converted into shaped light.

The aperture 2202b has an opening. When the light after passed through the coupling lens 2201b further passes through the aperture 2202b, the light is converted into shaped light.

The aperture 2202c has an opening. When the light after passed through the coupling lens 2201c further passes through the aperture 2202c, the light is converted into shaped light.

The aperture 2202d has an opening. When the light after passed through the coupling lens 2201d further passes through the aperture 2202d, the light is converted into shaped light.

When the light after passed through the opening of the aperture 2202a further passes through the cylindrical lens 2204a, the light is converted so that an image is formed with respect to the Z-axis direction near a deflecting/reflecting surface of the polygon mirror 2104.

When the light after passed through the opening of the aperture 2202b further passes through the cylindrical lens 2204b, the light is converted so that an image is formed with respect to the Z-axis direction near a deflecting/reflecting surface of the polygon mirror 2104.

When the light after passed through the opening of the aperture 2202c further passes through the cylindrical lens 2204c, the light is converted so that an image is formed with respect to the Z-axis direction near a deflecting/reflecting surface of the polygon mirror 2104.

When the light after passed through the opening of the aperture 2202d further passes through the cylindrical lens 2204d, the light is converted so that an image is formed with respect to the Z-axis direction near a deflecting/reflecting surface of the polygon mirror 2104.

The polygon mirror 2104 includes an upper layer and a lower layer each having four-side mirrors. Each mirror works as the deflecting/reflecting surface. The polygon mirror 2104 is arranged so that the rays of light coming from the cylindrical lenses 2204a and 2204d strike any of four-side mirrors of the upper layer, while the rays of light coming from the cylindrical lenses 2204b and 2204c strike any of four-side mirrors of the lower layer. The polygon mirror 2104 rotates in such a manner that the phase of the four-side mirrors of the upper layer is shifted 45° from the phase of the four-side mirrors of the lower layer; therefore, the upper layer and the lower layer are used alternately for the writing.

The rays of light coming from the cylindrical lenses 2204a and 2204b are deflected toward −X side of the polygon mirror 2104. The rays of light coming from the cylindrical lenses 2204c and 2204d are deflected toward +X side of the polygon mirror 2104.

Each fθ lens has a non-arch surface with a power that allows a spot of the light to move, by rotation of the polygon mirror 2104, on the surface of the corresponding photosensitive element in the main-scanning direction at a constant speed.

The fθ lenses 2105a and 2105b are arranged −X side of the polygon mirror 2104. The fθ lenses 2105c and 2105d are arranged +X side of the polygon mirror 2104.

The fθ lenses 2105a and 2105b are stacked on each other, aligned in the Z-axis direction in such a manner that the fθ lens 2105a faces to the four-side mirrors of the lower layer and the fθ lens 2105b faces to the four-side mirrors of the upper layer. The fθ lenses 2105c and 2105d are stacked on each other, aligned in the Z-axis direction in such a manner that the fθ lens 2105c faces to the four-side mirrors of the upper layer and the fθ lens 2105d faces to the four-side mirrors of the lower layer.

After the light coming from the cylindrical lens 2204a is deflected by the polygon mirror 2104, the light passes through the fθ lens 2105a, the reflecting mirror 2106a, the toroidal lens 2107a, and the reflecting mirror 2108a and then strikes the photosensitive element 2030a, thus a spot of light is formed on the photosensitive element 2030a. The spot of light moves along the longitudinal axis of the photosensitive element 2030a by rotation of the polygon mirror 2104. In other words, the surface of the photosensitive element 2030a is scanned with the spot of light. The moving direction of the spot of light is called "main-scanning direction" on the photosensitive element 2030a. The rotating direction of the photosensitive element 2030a is called "sub-scanning direction" on the photosensitive element 2030a.

After the light coming from the cylindrical lens 2204b is deflected by the polygon mirror 2104, the light passes through the fθ lens 2105b, the reflecting mirror 2106b, the toroidal lens 2107b, and the reflecting mirror 2108b and then strikes the photosensitive element 2030b, thus a spot of light is formed on the photosensitive element 2030b. The spot of light moves along the longitudinal axis of the photosensitive element 2030b by rotation of the polygon mirror 2104. In other words, the surface of the photosensitive element 2030b is scanned with the spot of light. The moving direction of the spot of light is called "main-scanning direction" on the photosensitive element 2030b. The rotating direction of the photosensitive element 2030b is called "sub-scanning direction" on the photosensitive element 2030b.

After the light coming from the cylindrical lens 2204c is deflected by the polygon mirror 2104, the light passes through the fθ lens 2105c, the reflecting mirror 2106c, the toroidal lens 2107c, and the reflecting mirror 2108c and then strikes the photosensitive element 2030c, thus a spot of light is formed on the photosensitive element 2030c. The spot of light moves along the longitudinal axis of the photosensitive element 2030c by rotation of the polygon mirror 2104. In other words, the surface of the photosensitive element 2030c is scanned with the spot of light. The moving direction of the spot of light is called "main-scanning direction" on the photosensitive element 2030c. The rotating direction of the photosensitive element 2030c is called "sub-scanning direction" on the photosensitive element 2030c.

After the light coming from the cylindrical lens 2204d is deflected by the polygon mirror 2104, the light passes through the fθ lens 2105d, the reflecting mirror 2106d, the toroidal lens 2107d, and the reflecting mirror 2108d and then strikes the photosensitive element 2030d, thus a spot of light is formed on the photosensitive element 2030d. The spot of light moves along the longitudinal axis of the photosensitive element 2030d by rotation of the polygon mirror 2104. In other words, the surface of the photosensitive element 2030d is scanned with the spot of light. The moving direction of the spot of light is called "main-scanning direction" on the photosensitive element 2030d. The rotating direction of the photosensitive element 2030d is called "sub-scanning direction" on the photosensitive element 2030d.

An area to be scanned or capable of carrying an image on each photosensitive element in the main-scanning direction is called "effective scanning area" or "image forming area".

The reflecting mirrors are arranged in such a manner that the optical length along which the light travels from the polygon mirror 2104 to the corresponding photosensitive element is set equal and the position and the angle of the incident light on each photosensitive element is set identical.

The cylindrical lens and the corresponding toroidal lens together form an optical face tangle error correcting system that adjusts the conjugate relation between the point of deflection and the surface of the corresponding photosensitive element with respect to the sub-scanning direction.

The optical system that is arranged on the optical path between the polygon mirror 2104 and the corresponding photosensitive element is also called "optical scanning system". In the present embodiment, the fθ lens 2105a, the toroidal lens 2107a, and the reflecting mirrors (2106a and 2108a) together form the optical scanning system for the K station. The fθ lens 2105b, the toroidal lens 2107b, and the reflecting mirrors (2106b and 2108b) together form the optical scanning system for the C station. The fθ lens 2105c, the toroidal lens 2107c, and the reflecting mirrors (2106c and 2108c) together form the optical scanning system for the M station. The fθ lens 2105d, the toroidal lens 2107d, and the reflecting mirrors (2106d and 2108d) together form the optical scanning system for the Y station.

After the light that is deflected by the polygon mirror 2104 passes through the scanning optical system for the K station, part of the light enters the light detection sensor 2205a via the light detection mirror 2207a before the start of writing.

After the light that is deflected by the polygon mirror 2104 passes through the scanning optical system for the C station, part of the light enters the light detection sensor 2205b via the light detection mirror 2207b before the start of writing.

After the light that is deflected by the polygon mirror 2104 passes through the scanning optical system for the M station, part of the light enters the light detection sensor 2205c via the light detection mirror 2207c before the start of writing.

After the light that is deflected by the polygon mirror 2104 passes through the scanning optical system for the Y station, part of the light enters the light detection sensor 2205d via the light detection mirror 2207d before the start of writing.

Each light detection sensor outputs a signal according to the amount of light received (photoelectric conversion signal).

The scanning control device calculates, on the basis of the signal output from each light detection sensor, a point of time to start the scanning onto the corresponding photosensitive element.

The toner-density calculator 2245 is described below.

Figure 32:
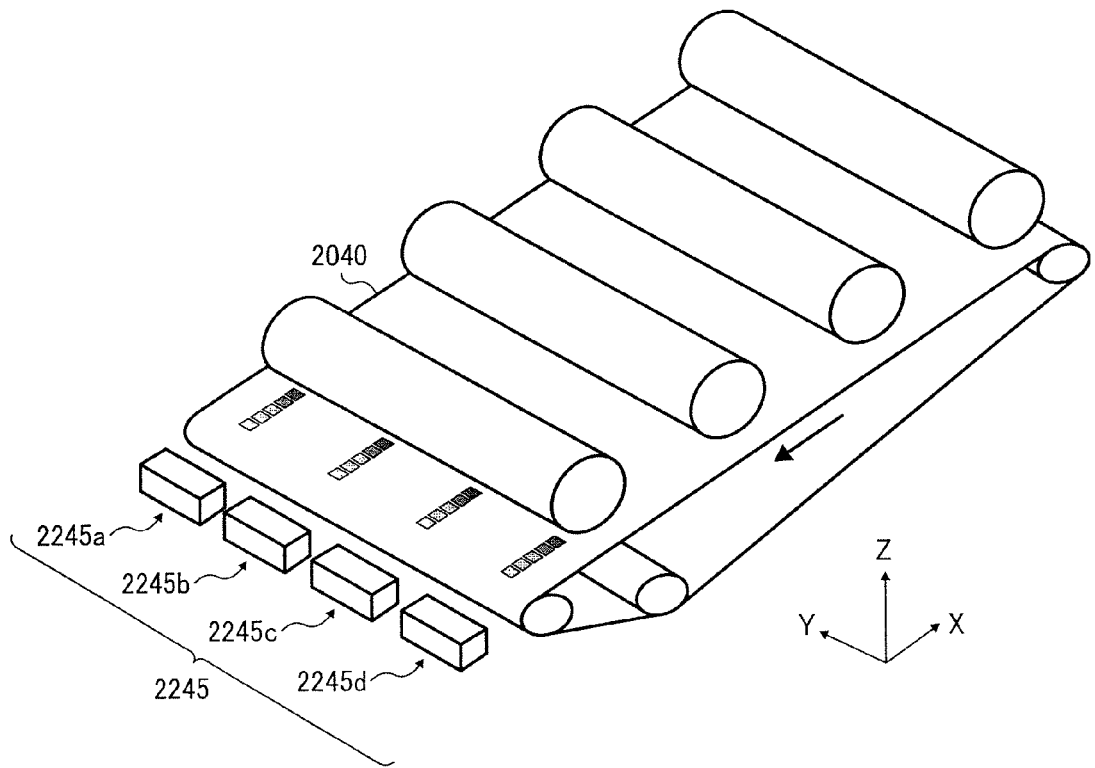
FIG. 32 is a perspective view of a toner-density calculator shown in FIG. 27.

As shown in FIG. 32 for example, the toner-density calculator 2245 includes four detection sensors (2245a, 2245b, 2245c, and 2245d).

The detection sensor 2245a is at a position opposed to around the +Y-side edge of the transfer belt 2040; and the detection sensor 2245d is a position opposed to around the −Y side edge of the transfer belt 2040. The detection sensor 2245b is on −Y side of the detection sensor 2245a; and the detection sensor 2245c is on +Y side of the detection sensor 2245d. The positions of the detection sensors 2245b and 2245c are set in such a manner that the detection sensors are spaced from each other at substantially equal intervals in the Y-axis direction.

Figure 33:
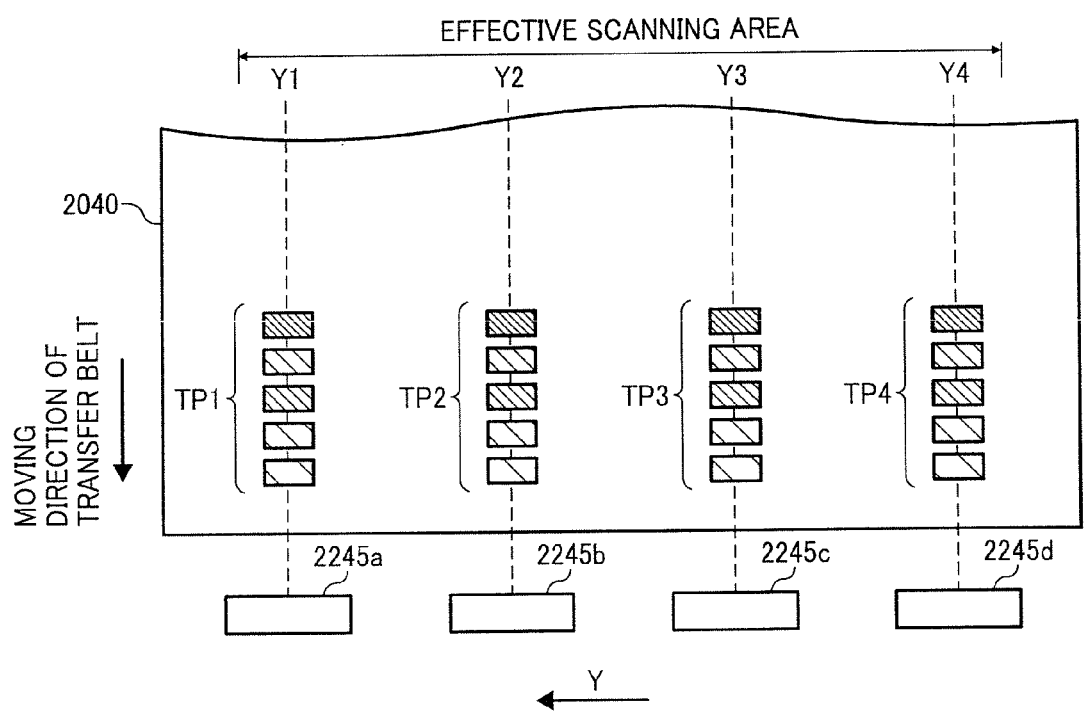
FIG. 33 is a schematic diagram that explains how detection sensors are arranged.

As shown in FIG. 33 for example, it is assumed that the center position of the detection sensor 2245a in the Y-axis direction is set as Y1, the center position of the detection sensor 2245b as Y2, the center position of the detection sensor 2245c as Y3, and the center position of the detection sensor 2245d as Y4. A toner pattern that is opposed to the detection sensor 2245a is called "toner pattern TP1"; a toner pattern that is opposed to the detection sensor 2245b is called "toner pattern TP2"; a toner pattern that is opposed to the detection sensor 2245c is called "toner pattern TP3"; and a toner pattern that is opposed to the detection sensor 2245d is called "toner pattern TP4".

The toner pattern TP1 is a yellow toner pattern; the toner pattern TP2 is a magenta toner pattern; the toner pattern TP3 is a cyan toner pattern; and the toner pattern TP4 is a black toner pattern.

When the toner-density calculating process performed by the toner-density calculator 2245 starts, the printer control device 2090 sends an instruction to the scanning control device to form the toner patterns.

The scanning control device causes the Y station to form the yellow toner pattern TP1 at the position on the photosensitive element 2030d corresponding to Y1, the M station to form the magenta toner pattern TP2 at the position on the photosensitive element 2030c corresponding to Y2, the C station to form the cyan toner pattern TP3 at the position on the photosensitive element 2030b corresponding to Y3, and the K station to form the black toner pattern TP4 at the position on the photosensitive element 2030a corresponding to Y4.

The yellow toner pattern TP1 formed by the Y station is transferred onto the transfer belt 2040 at the position corresponding to Y1; the magenta toner pattern TP2 formed by the M station is transferred onto the transfer belt 2040 at the position corresponding to Y2; the cyan toner pattern TP3 formed by the C station is transferred onto the transfer belt 2040 at the position corresponding to Y3; and the black toner pattern TP4 formed by the K station is transferred onto the transfer belt 2040 at the position corresponding to Y4. The different-colored toner patterns can be called, collectively, "toner pattern TP" if there is no need to identify the individual toner patterns.

Figure 34:
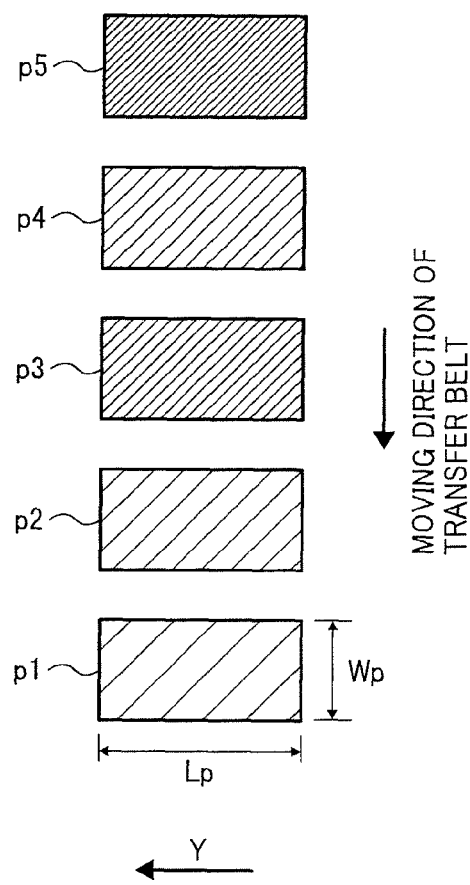
FIG. 34 is a schematic diagram of toner patterns.

As shown in FIG. 34 for example, the toner pattern TP includes five quadrangular patterns p1 to p5 (hereinafter, "rectangular patterns"). The rectangular patterns are aligned in a row along the moving direction of the transfer belt 2040. The rectangular patterns have different toner densities. The width of the rectangular pattern in the Y-axis direction is Lp, and the length of the rectangular in the moving direction of the transfer belt 2040 is Wp.

The toner densities can be changed appropriately by adjusting the laser power emitted from the light source, adjusting the driving pulse duty supplied to the light source, and adjusting the developing bias.

Figure 35:
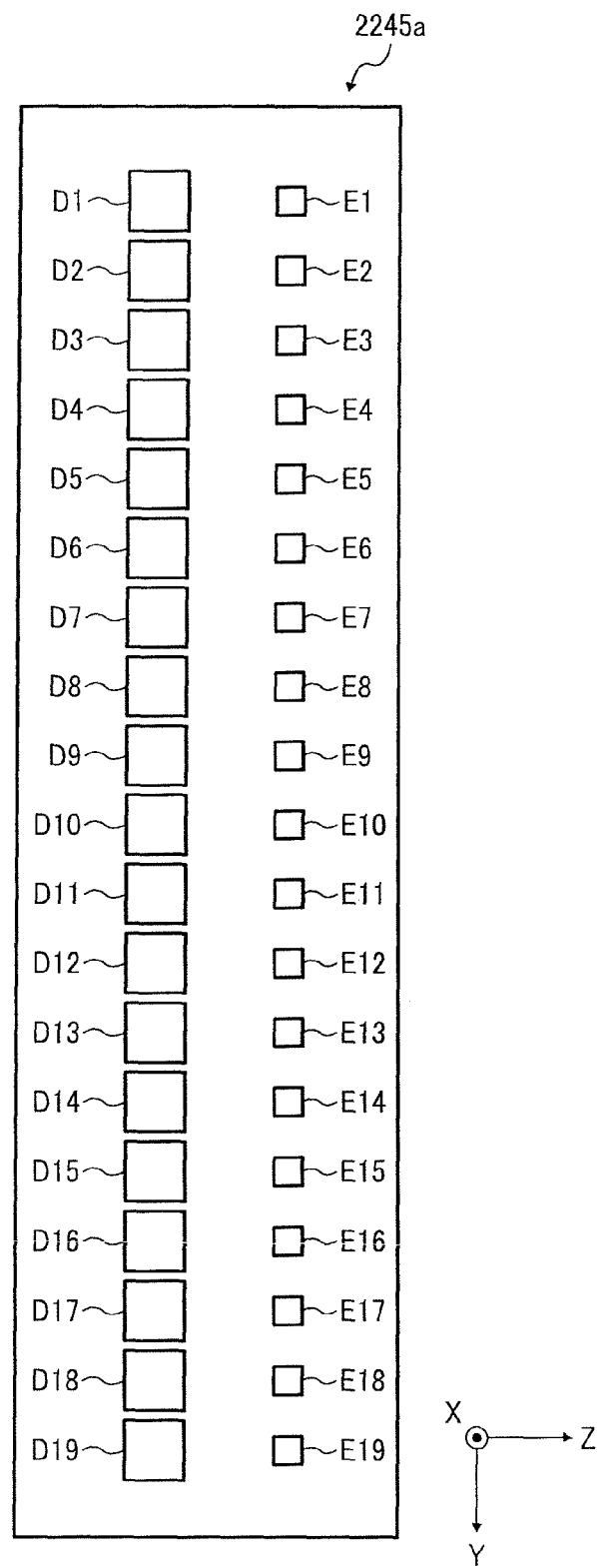
FIG. 35 is a first schematic diagram illustrating the detection sensor.

As shown in FIGS. 35 and 36 for example, the detection sensor 2245a includes nineteen light-emitting elements (E1 to E19), nineteen detection-light collecting lenses (LE1 to LE19), nineteen light-receiving elements (D1 to D19), and a processing device (not shown).

The nineteen light-emitting elements (E1 to E19) are aligned in the Y-axis direction at equal intervals Le. Each light-emitting element is, for example, an LED. It is assumed, for example, Le=0.4 mm. Each light-emitting element emits light to the transfer belt 2040 in such a manner that the optical path lies on the XZ plane making an angle with the X-axis direction (see FIG. 37).

The detection-light collecting lenses (LE1 to LE19) correspond to the light-emitting elements (E1 to E19), respectively.

Each detection-light collecting lens is arranged +X side of the corresponding light-emitting element. The detection-light collecting lens causes a light ray received from the corresponding light-emitting element to converge to the surface of the transfer belt 2040.

Each detection-light collecting lens is, for example, a spherical lens or an anamorphic lens having light-gathering powers in both the Y-axis direction and the Z-axis direction.

The light-receiving elements (D1 to D19) correspond to the light-emitting elements (E1 to E19), respectively.

Each light-receiving element is arranged −Z side of the corresponding light-emitting element. The light-receiving element is at the position to receive, when the corresponding light-emitting element emits a light ray to the surface of the transfer belt 2040, light specularly reflected by the surface of the transfer belt 2040. The pitch of the nineteen light-receiving elements is equal to the pitch of the nineteen light-emitting elements.

Each light-receiving element is, for example, a PD. Each light-receiving element outputs a signal according to the amount of light received.

The other detection sensors (2245*b*, 2245*c*, and 2245*d*) have the same structure as the detection sensor 2245*a* has.

As shown in FIG. 38 for example, the converging light rays that have been emitted from the light-emitting elements (E1 to E19) and passed through the detection-light collecting lenses (LE1 to LE19) illuminate the transfer belt 2040 as rays of detection light (S1 to S19). The spot of detection light formed on the surface of the transfer belt 2040 is, for example, 0.2 mm in diameter. It is noted that a spot of conventional detection light is about 2 mm to about 3 mm in diameter.

The surface of the transfer belt 2040 is specular and, therefore, almost all the light illuminates the surface of the transfer belt 2040 is specularly reflected by the surface of the transfer belt 2040.

Part of the light emitted from the each light-emitting element may enter a detection-light collecting lens other than the corresponding detection-light collecting lens (see FIG. 39). Herein, the detection-light collecting lens corresponding to the on-state light-emitting element is called "corresponding detection-light collecting lens" and the detection-light collecting lenses other than the corresponding detection-light collecting lens are called "non-corresponding detection-light collecting lenses".

Coupled light passed through any of the non-corresponding detection-light collecting lenses illuminates the transfer belt 2040 as flare light. The rays of coupled light each passed through the detection-light collecting lens (LE1 to LE19) are called rays of flare light (F1 to F19). If light enters a non-corresponding detection-light collecting lens far away from the corresponding detection-light collecting lens, the incident light is totally reflected by the non-corresponding detection-light collecting lens; therefore, no flare light occurs because no light can pass through the non-corresponding detection-light collecting lens. In general, the diameter of a spot of flare light is larger than the diameter of a spot of detection light. The intensity of a spot of flare light is weaker than the intensity of a spot of detection light.

When the light-emitting element E10 turns ON, as shown in FIG. 40 for example, the detection light S10 and a plurality of rays of flare light illuminate the transfer belt 2040. These rays of light are specularly reflected by the transfer belt 2040, as shown in FIG. 41 for example. To make the description simpler, only the detection light S10 and the four rays of flare light (F8, F9, F11, and F12) are taken into consideration.

Figure 42:
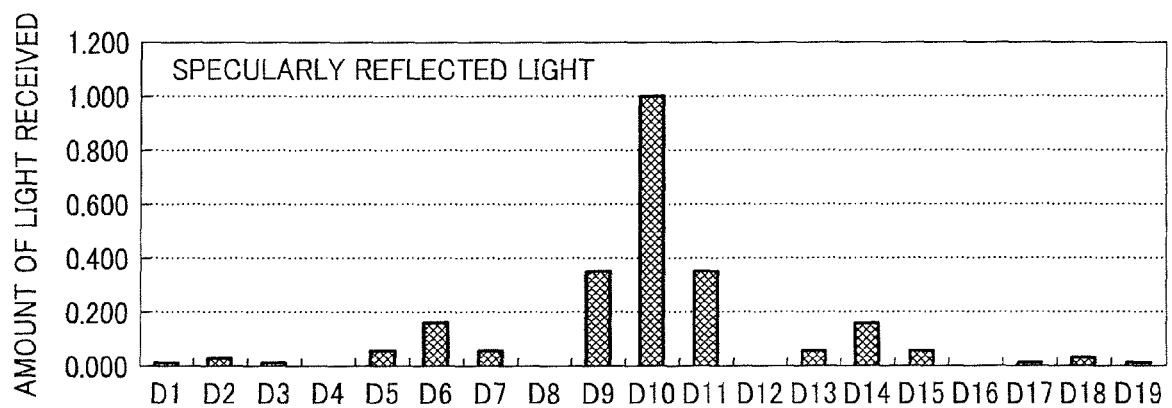
FIG. 42 is a graph of the amount of light received at each light-receiving element in the situation shown in FIG. 41 (first referential amount of light received)

The amounts of light received at the individual light-emitting elements in the above situation are shown in FIG. 42. The amounts of light received at the light-receiving elements D1 to D3 are attributed to the flare light F8 specularly reflected. The amounts of light received at the light-receiving elements D5 to D7 are attributed to the flare light F9 specularly reflected. The amounts of light received at the light-receiving elements D9 to D11 are attributed to the detection light S10 specularly reflected. The amounts of light received at the light-receiving elements D13 to D15 are attributed to the flare light F11 specularly reflected. The amounts of light received at the light-receiving elements D17 to D19 are attributed to the flare light F12 specularly reflected. The four light-receiving elements D4, D8, D12, and D16 receive no specularly reflected light. It is assumed that the amount of light received at the light-receiving element D10 is 1.

Figure 43:
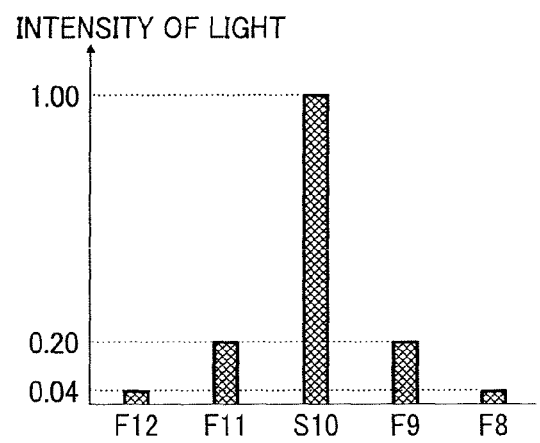
FIG. 43 is a graph of the intensity of the rays of detection light S10 and flare light (F8, F9, F11, and F12)

FIG. 43 is a graph of the intensity of the detection light S10 and the intensities of the four rays of flare light (F8, F9, F11, and F12). If the intensity of the detection light S10 is set to 1, the intensity of the flare light F8 and F12 is 0.2 and the intensity of the flare light F9 and F11 is 0.04.

The toner-density calculating process using the toner-density calculator 2245 is described below. Suppose, for example, there is a case where the light-emitting element E10 is in operation and the other eighteen light-emitting elements are not.

1. The printer control device 2090 turns ON the light-emitting element E10 of each detection sensor. The light illuminates the transfer belt 2040.

2. The processing device of each detection sensor calculates the amount of light received at each light-receiving element on the basis of the signal output from the corresponding light-emitting element. The processing device stores the amount of light received as "first referential amount of light received" in a memory (not shown).

3. The printer control device 2090 causes the scanning control device to form, at specific positions, different colored toner patterns each small enough to be exposed to no light other than the detection light S10, i.e., exposed to no flare light. In this example, Lp=1.0 mm.

4. The printer control device 2090 turns ON the light-emitting element E10 of each detection sensor a predetermined time after. The point of time to form the toner pattern is decided and a time taken for the toner pattern to move in front of the detection sensor (to the detection area) is substantially fixed. The printer control device 2090 turns the light-emitting element E10 ON at an appropriate point of time when it is determined that the toner pattern comes close enough to the detection area.

With this configuration, when the rectangular pattern is in front of the detection sensor, as shown in FIG. 44 for example, the detection light S10 strikes the rectangular pattern and the plurality of rays of flare light strikes the transfer belt 2040. As shown in FIG. 45 for example, the detection light S10 is specularly and diffusely reflected by the rectangular pattern and the plurality of rays of flare light is specularly reflected by the surface of the transfer belt 2040. Hereinafter, light specularly reflected is called "specularly reflected light" and light diffusely reflected is called "diffusely reflected light".

Figure 46:
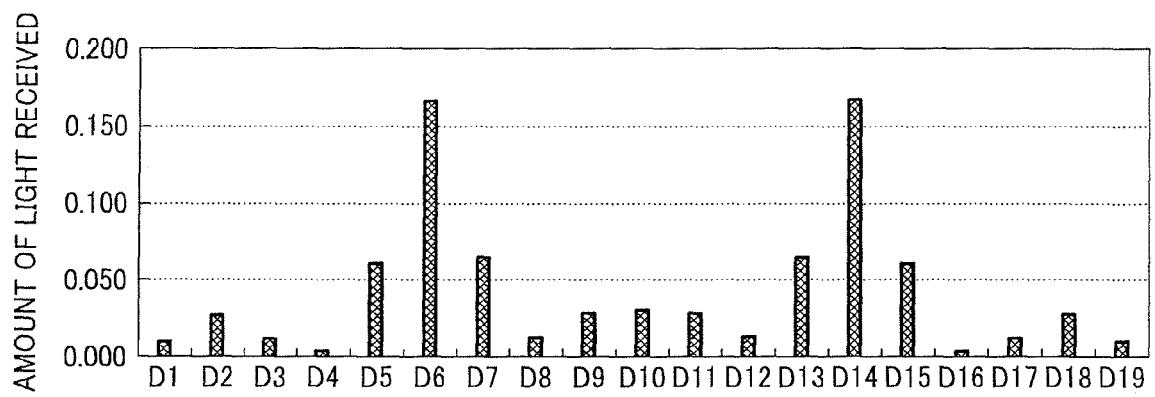
FIG. 46 is a graph of the amount of light received at each light-receiving element in the situation shown in FIG. 44 (second referential amount of light received)

5. The processing device of each detection sensor calculates the amount of light received at each light-receiving element on the basis of the signal output from the corresponding light-receiving element and stores the calculated amount as "second referential amount of light received" in a memory (not shown). The calculated amounts of light received at the individual light-receiving elements are shown in FIG. 46.

6. The processing device of each detection sensor separates the second referential amount of light received at each light-receiving element into an amount of diffusely reflected light and an amount of specularly reflected light.

6-1. Light-Receiving Element D10

The light-receiving element D10 is corresponding to the on-state light-emitting element E10. Therefore, the second referential amount of light received at the light-receiving element D10 is completely due to the detection light S10 specularly reflected. Because the reflectance of the rectangular pattern is lower than the reflectance of the transfer belt 2040, the second referential amount of light received at the light-receiving element D10 is smaller than the first referential amount of light received.

6-2. Light-Receiving Elements D4, D8, D12, and D16

The first referential amount of light received at each light-receiving element is zero (see FIG. 42). Therefore, the second referential amount of light received at each light-receiving element is completely due to the detection light S10 diffusely reflected.

6-3. Light-Receiving Elements D1 to D3, D5 to D7, D13 to D15, and D17 to D19

Each light-receiving element receives both the flare light specularly reflected and the detection light S10 diffusely reflected. The second referential amount of light received at each light-receiving element is larger than the first referential amount of light received by an amount of received detection light S10 diffusely reflected. Therefore, the difference between the second referential amount of light received and the first referential amount of light received is due to the detection light S10 diffusely reflected. The first referential amount of light received is due to the flare light specularly reflected.

6-4. Light-Receiving Element D9

The ratio between the amount of diffusely reflected detection light S10 received at the light-receiving element D9 and the amount of specularly reflected detection light S10 received at the light-receiving element D9 is fixed, regardless whether the detection light S10 strikes the transfer belt 2040 or the rectangular pattern. Accordingly, the amount of diffusely reflected detection light S10 received is calculated in the following procedure.

(1) The ratio (hereinafter, "ratio A") is calculated by dividing the first referential amount of light received at the light-receiving element D9 by the first referential amount of light received at the light-receiving element D10. The ratio A is 0.35 in this example (see FIG. 42).

(2) The second referential amount of light received at the light-receiving element D10 is multiplied by the ratio A. The calculated value is the amount of specularly reflected detection light S10 contained in the second referential amount of light received at the light-receiving element D9 (hereinafter, "amount of light received a").

(3) The amount of light received a is subtracted from the second referential amount of light received at the light-receiving element D9. The calculated value is the amount of diffusely reflected detection light S10 contained in the second referential amount of light received at the light-receiving element D9.

6-5. Light-Receiving Element D11

The ratio between the amount of diffusely reflected detection light S10 received at the light-receiving element D11 and the amount of specularly reflected detection light S10 received at the light-receiving element D11 is fixed, regardless whether the detection light S10 strikes the transfer belt 2040 or the rectangular pattern. Accordingly, the amount of diffusely reflected detection light S11 received is calculated in the following procedure. The ratio (hereinafter, "ratio B") is calculated by dividing the first referential amount of light received at the light-receiving element D11 by the first referential amount of light received at the light-receiving element D10 (Step 1). The ratio B is 0.35 in this example (see FIG. 42). The second referential amount of light received at the light-receiving element D11 is multiplied by the ratio B (Step 2). The calculated value is the amount of specularly reflected detection light S10 contained in the second referential amount of light received at the light-receiving element D11 (hereinafter, "amount of light received b"). The amount of light received b is subtracted from the second referential amount of light received at the light-receiving element D11 (Step 3). The calculated value is the amount of diffusely reflected detection light S10 contained in the second referential amount of light received at the light-receiving element D11.

Figure 47:
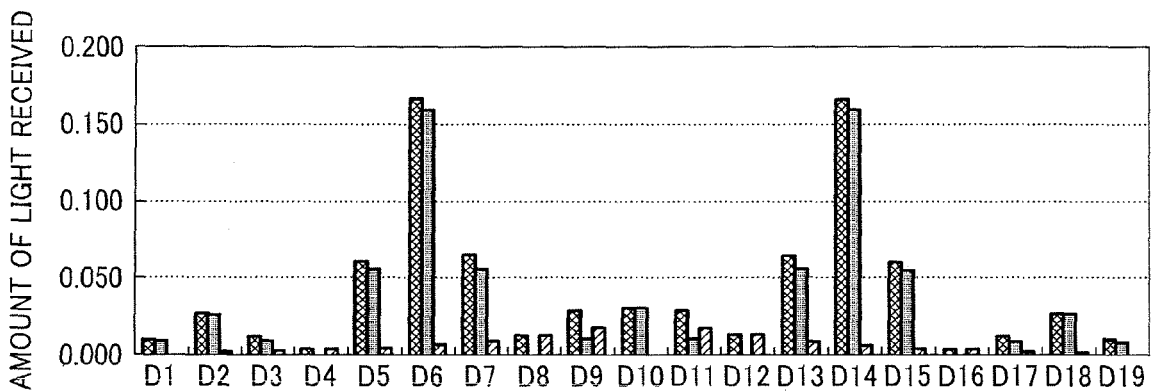
FIG. 47 is a graph of the second referential amount of light received that is separated into the amount of specularly reflected light received and the amount of diffusely reflected light received.

The amount of diffusely reflected light and the amount of specularly reflected light contained in the second referential amount of light received are calculated and divided in this manner to show the result of the calculation in FIG. 47.

7. The printer control device 2090 causes the scanning control device to form, at specific positions, different colored toner patterns each small enough to be exposed to the detection light S9 and the flare light F9. In this example, Lp=2.0 mm.

With this configuration, when the rectangular pattern is in front of the detection sensor, as shown in FIG. 48 for example, the detection light S10 and the flare light F9 strike the rectangular pattern and the rays of flare light other than the flare light F9 strike the transfer belt 2040. As shown in FIG. 49 for example, the detection light S10 and the flare light F9 is specularly and diffusely reflected by the rectangular pattern and the rays of flare light other than the flare light F9 is specularly reflected by the surface of the transfer belt 2040.

Figure 50:
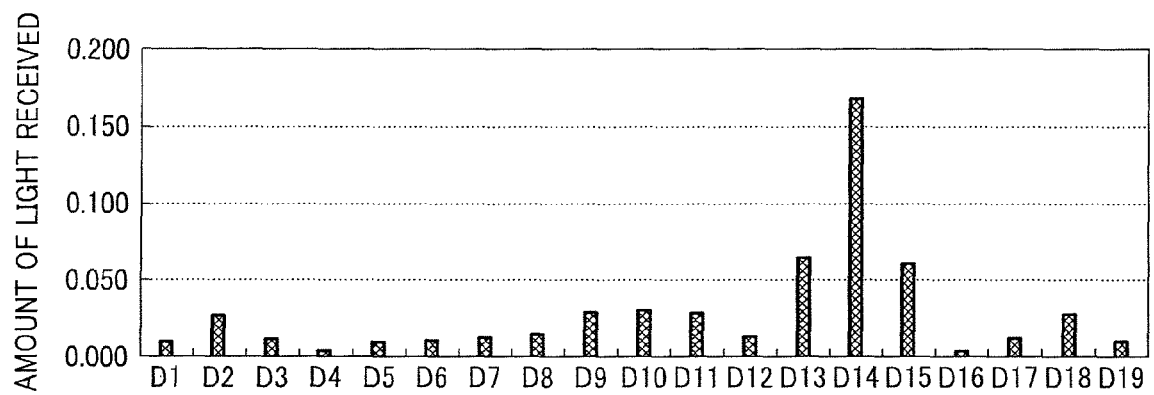
FIG. 50 is a graph of the amount of light received at each light-receiving element in the situation shown in FIG. 48 (first calculated amount of light received)

8. The processing device of each detection sensor calculates the amount of light received at each light-receiving element on the basis of the signal output from the corresponding light-receiving element and stores the calculated amount as "calculated amount of light received" in a memory (not shown). The calculated amounts of light received at the individual light-receiving elements are shown in FIG. 50. Some of the nineteen light-receiving elements receive the flare light F9 diffusely reflected and others receive the flare light F9 specularly reflected.

9. The processing device of each detection sensor separates the calculated amount of light received at each light-receiving element into an amount of diffusely reflected light and an amount of specularly reflected light.

9-1. Light-Receiving Elements D9 to D11

The calculated amount of light received at each light-receiving element is larger than the second referential amount of light received. This is because the flare light F9 diffusely reflected is received at each light-receiving element. The amount of specularly reflected light contained in the calculated amount of light received is equal to the amount of specularly reflected light contained in the second referential amount of light received. Therefore, the amount of diffusely reflected light contained in the calculated amount of light received is calculated by subtracting, from the calculated amount of light received, the amount of specularly reflected light contained in the second referential amount of light received.

9-2. Light-Receiving Elements D4, D8, D12, and D16

The calculated amount of light received at each light-receiving element is larger than the second referential amount of light received. This is because the flare light F9 diffusely reflected is received at each light-receiving element. Therefore, the calculated amount of light received at each light-receiving element is completely due to the diffusely reflected light.

9-3. Light-Receiving Elements D1 to D3, D13 to D15, and D17 to D19

The calculated amount of light received at each light-receiving element is larger than the second referential amount of light received. This is because the flare light F9 diffusely reflected is received at each light-receiving element. The amount of specularly reflected light contained in the calculated amount of light received is equal to the amount of specularly reflected light contained in the second referential amount of light received. Therefore, the amount of diffusely reflected light contained in the calculated amount of light received is calculated by subtracting, from the calculated amount of light received, the amount of specularly reflected light contained in the second referential amount of light received.

9-4. Light-Receiving Elements D5 to D7

The calculated amount of light received at each light-receiving element is smaller than the second referential amount of light received. This is because the flare light F9 strikes the rectangular pattern instead of the surface of the transfer belt 2040. The reflectance of the rectangular pattern is almost free from change in the incident angle. Therefore, the amount of diffusely reflected light contained in the calculated amount of light received is calculated in the following procedure. The ratio (hereinafter, "ratio C") is calculated by dividing the second referential amount of light received at the light-receiving element D10 by the first referential amount of light received at the light-receiving element D10 (Step 1). The amount of specularly reflected light contained in the second referential amount of light received at each of the light-receiving elements (D5 to D7) is multiplied by the ratio C (Step 2). The calculated value is the amount of specularly reflected light contained in the calculated amount of light received at each of the light-receiving elements (D5 to D7) (hereinafter, "amount of light received c"). The amount of light received c is subtracted from the calculated amount of light received at each of the light-receiving elements (D5 to D7) (Step 3). The calculated value is the amount of diffusely reflected light contained in the calculated amount of light received at each of the light-receiving elements (D5 to D7).

Figure 51:
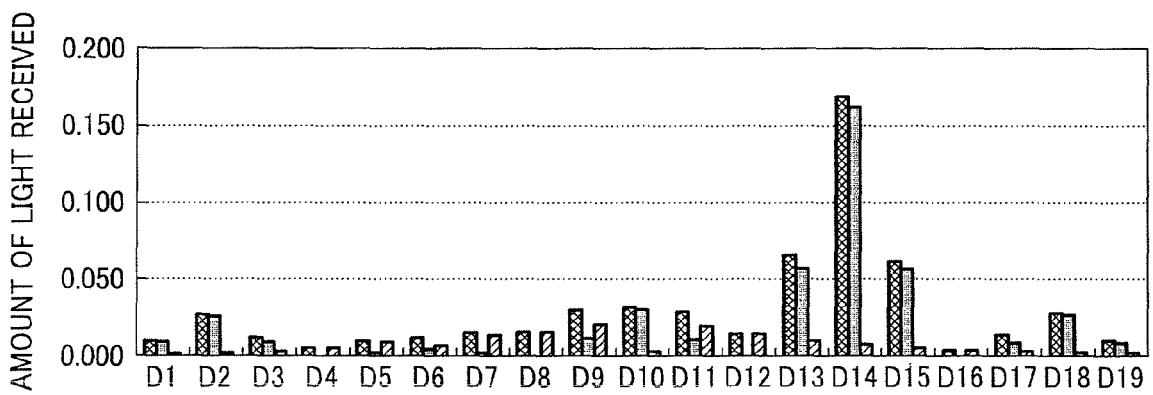
FIG. 51 is a graph of the first calculated amount of light received that is separated into the amount of specularly reflected light received and the amount of diffusely reflected light received.

The amount of diffusely reflected light and the amount of specularly reflected light contained in the calculated amount of light received are calculated in this manner and the result of the calculation is shown in FIG. 51. It is noted that both the total amount of diffusely reflected light contained in the calculated amounts of light received and the total amount of specularly reflected light contained in the calculated amounts of light received are sent to the printer control device 2090.

The output from a light-receiving element that receives diffusely reflected light depends on the toner density of the rectangular pattern. More particularly, as the toner density increases (the amount of toner of the toner pattern increases), light specularly reflected decreases and light diffusely reflected increases.

10. The printer control device 2090 determines, on the basis of the total amount of diffusely reflected light contained in the calculated amount of light received at detection sensor 2245a, whether the yellow toner density is appropriate. The printer control device 2090 determines, on the basis of the total amount of diffusely reflected light contained in the calculated amount of light received at detection sensor 2245b, whether the magenta toner density is appropriate. The printer control device 2090 determines, on the basis of the total amount of diffusely reflected light contained in the calculated amount of light received at detection sensor 2245c, whether the cyan toner density is appropriate. The printer control device 2090 determines, on the basis of the total amount of diffusely reflected light contained in the calculated amount of light received at detection sensor 2245d, whether the black toner density is appropriate. If the toner density is not appropriate, the printer control device 2090 adjusts the developing system of the corresponding station so that the toner density is set to an appropriate value.

When the rays of detection light S10 and flare light F9 strike the rectangular pattern, the total amount of diffusely reflected light received increases when compared with the case where the single ray of detection light S10 strikes the rectangular pattern. It means that the difference between the reflection characteristics of the transfer belt 2040 and the reflection characteristics of the toner pattern increases. The increased difference between the reflection characteristics of the transfer belt 2040 and the reflection characteristics of the toner pattern makes it possible to accurately determine whether the toner density of the toner pattern is different from the target value. In other words, the increased difference improves the accuracy in the toner-density calculation.

It is clear from the above description that, in the image forming apparatus 2000 according to the present embodiment, a toner-density calculating sensor according to the present embodiment is formed with the toner-density calculator 2245. The nineteen light-emitting elements (E1 to E19) together form at least three light-emitting units; the nineteen detection-light collecting lenses (LE1 to LE19) together form a light-collecting optical system; and the nineteen light-receiving elements (D1 to D19) together form three light-receiving units.

Moreover, a control device according to the present embodiment is formed with the printer control device 2090. A pattern used for density calculation according to the present embodiment is formed with the toner pattern.

During the above-described toner-density calculating process, a toner-density calculating method according to the present embodiment is operated by the processing device.

As described above, the image forming apparatus 2000 according to the present embodiment includes the four photosensitive elements (2030a, 2030b, 2030c, and 2030d); the optical scanning device that scans each of the photosensitive elements in the main-scanning direction with the ray of light modulated appropriately according to the corresponding image data, thereby forming a latent image; the developing rollers (2033a, 2033b, 2033c, and 2033d) each develops the latent image into a toner image; the transfer roller 2042 that transfers the toner images onto the transfer belt 2040; the toner-density calculator 2245 that calculates the toner density of the toner pattern formed on the transfer belt 2040; the printer control device 2090 that controls the image forming apparatus 2000, etc.

The toner-density calculator 2245 includes the four detection sensors (2245a, 2245b, 2245c, and 2245d) each for the different colors.

The detection sensors are aligned in a row in the Y-axis direction at equal intervals Le. Each detection sensor includes the nineteen light-emitting elements (E1 to E19) each emits light to the transfer belt 2040; the nineteen detection-light collecting lenses (LE1 to LE19) each causes the light received from the corresponding light-emitting element to converge; the nineteen light-receiving elements (D1 to D19) each receives light reflected by the transfer belt 2040 or the toner pattern; and the processing device.

The processing device of each detection sensor calculates the amounts of light received at the individual light-receiving element on the basis of the signal output from the nineteen light-receiving elements; checks both the first referential amount of light received at each light-receiving element observed when the transfer belt 2040 is exposed to the detection light and the flare light and the second referential amount of light received at each light-receiving element observed when the detection pattern is exposed to no light other than the detection light; and separates the calculated amount of light received into the amount of diffusely reflected light received and the amount of specularly reflected light received. More particularly, as the amount of diffusely reflected light received, the amount of diffusely reflected detection light received and the amount of diffusely reflected flare light received are calculated.

The printer control device 2090 determines, on the basis of the total amount of diffusely reflected light contained in the calculated amount of light received at each detection sensor, whether the toner density is appropriate. If the toner density is not appropriate, the printer control device 2090 adjusts the developing system of the corresponding station so that the toner density is set to an appropriate value. Because not only the detection light diffusely reflected but also the flare light diffusely reflected are used, even if the detection pattern is small, the toner density can be calculated accurately.

The conventional toner-density calculating sensor that calculates the toner density includes one or two light-emitting elements or three light-emitting elements having different wavelength characteristics; and one or two light-receiving elements that receive reflected light. The length Lp of the toner pattern in the main-direction (i.e., the Y-axis direction) is set from 15 mm to 25 mm so that even if the toner pattern is misaligned with respect to the toner-density calculating sensor, the entire spot of the detection light is formed within the toner pattern. Because the main activity or the image forming process cannot be performed during the time when the toner-density calculating process is running, as the time taken to form the toner pattern increases, the operating efficiency of the image formation decreases. Moreover, toner used for forming the toner pattern is toner used for a secondary activity other than the main activity or the image formation. The amount of toner used for a secondary activity affects the length of the lifetime of the toner cartridge.

According to the present embodiment, the length of the toner pattern in the main-direction can be set to one-tenth of the length of the conventional toner pattern, which makes it possible to considerably decrease the time taken to form the toner pattern. Therefore, a high-quality image is formed with the operating efficiency maintained high. Moreover, the area of the toner pattern can be set to one-hundredth of the area of the conventional toner pattern, which makes it possible to considerably decrease the amount of toner used for the secondary activity. This makes the lifetime of the toner cartridge longer.

Figure 52:
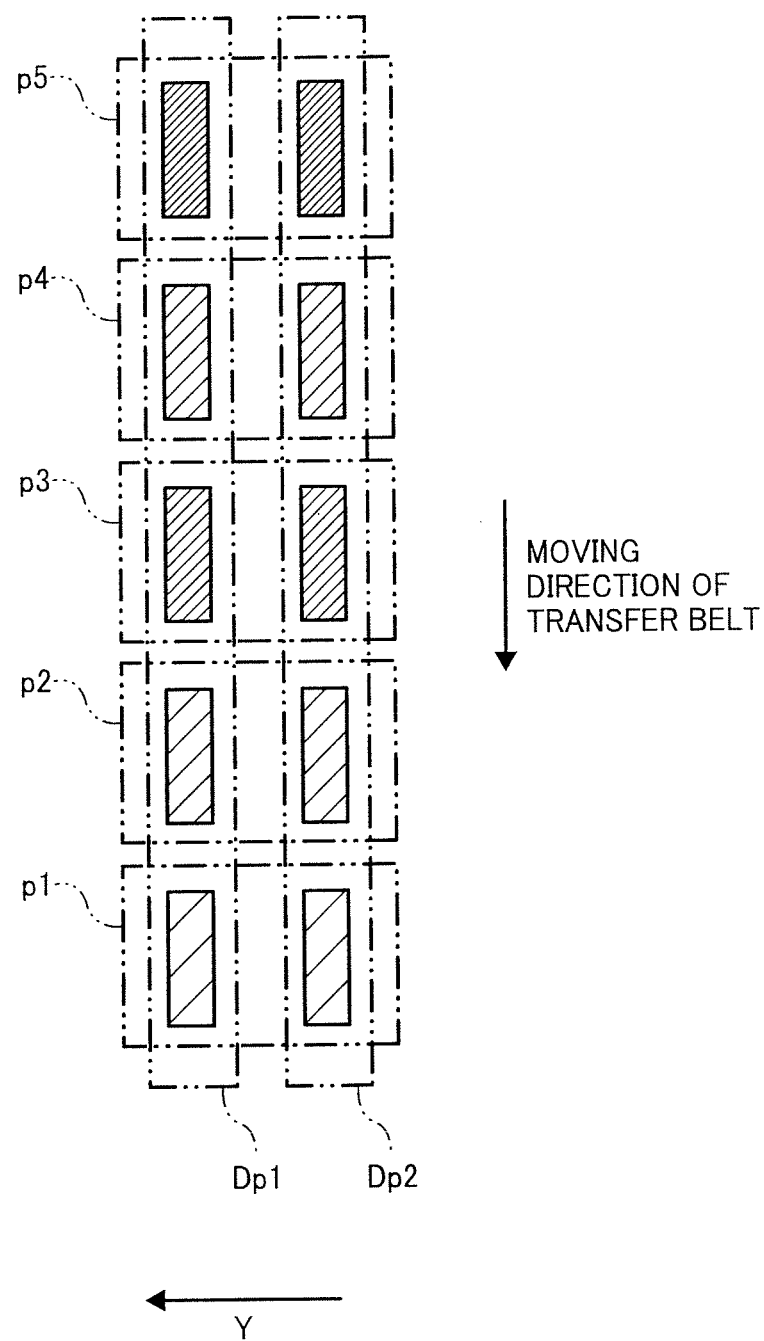
FIG. 52 is a schematic diagram of a toner pattern that is a modification of FIG. 44.

As one modification of the above-described embodiment, it is allowable to separate, as shown in FIGS. 52 to 54 for example, each rectangular pattern into two small rectangular patterns (Dp1 and Dp2) so that the detection light S10 and the flare light F9 strike the two small rectangular patterns, respectively. With this configuration, the amount of toner consumed decreases with the accuracy in the toner-density calculation maintained high. The length of each small rectangular pattern in the Y-axis direction is set about 1 mm.

Figure 57:
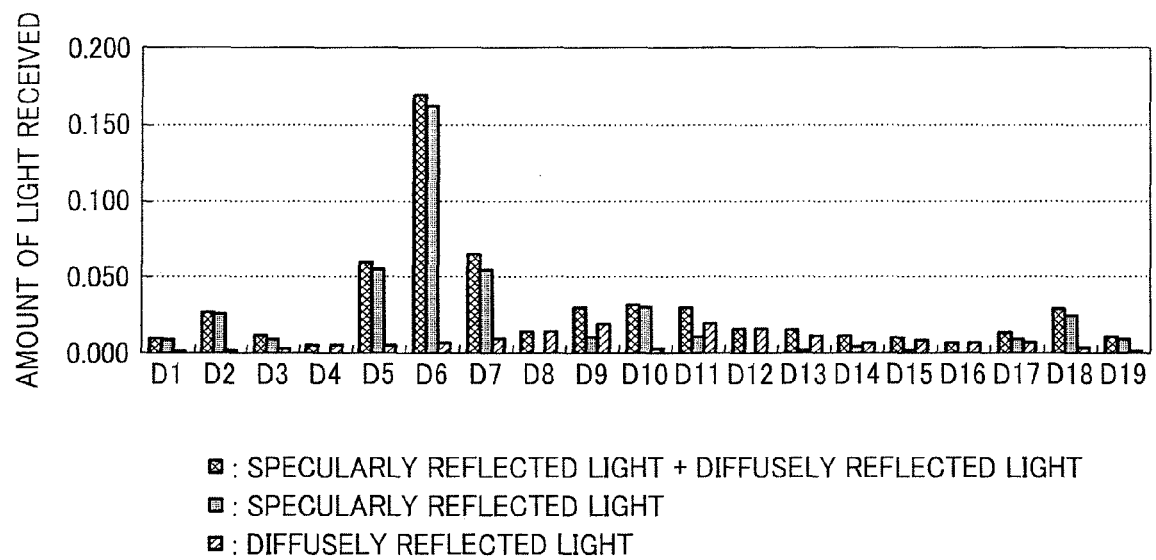
FIG. 57 is a graph of the amount of light received at each light-receiving element in the situation shown in FIG. 55.

As one example of the above-described embodiment, it is allowable, as shown in FIGS. 55 and 56, to configure the printer control device 2090 to send, when the toner-density calculating process starts, the size and the position of the toner pattern to be formed to the scanning control device so that the toner pattern is formed at the specific position with the size appropriate to be exposed to the spot of the detection light S10 and the spot of the flare light F11. The amount of light received at each light-receiving element in this situation is separable into the amount of diffusely reflected light received and the amount of specularly reflected light received. The calculated amount of diffusely reflected light received and the calculated amount of specularly reflected light received, i.e., the result of the separation of the amount of light received at each light-receiving element observed when the detection light S10 and the flare light F11 strike the toner pattern are shown in FIG. 57. As one modification of the above example, as shown in FIGS. 58 and 59, it is also allowable to separate each rectangular pattern into two small rectangular patterns (Dp1 and Dp2) so that the detection light S10 and the flare light F11 strike the two small rectangular patterns (Dp1 and Dp2), respectively. With this configuration, the amount of toner consumed decreases more with the accuracy in the toner-density calculation maintained high.

As an example of the above-described embodiment; it is allowable to configure the printer control device 2090 to send, when the toner-density calculating process starts, the size and the position of the toner pattern to be formed to the scanning control device so that the toner pattern is formed at the specific position with the size appropriate to be exposed to the spot of the detection light S10 and the spots of the two rays of flare light (F8 and F9).

In this case, as shown in FIG. 60 for example, when the rectangular pattern is in front of the detection sensor, the detection light S10 and the two rays of flare light (F8 and F9) strike the rectangular pattern, while the flare light other than the rays of flare light (F8 and F9) strikes the transfer belt 2040. As a result, as shown in FIG. 61 for example, the detection light S10 and the two rays of flare light (F8 and F9) are reflected specularly and diffusely by the rectangular pattern, while the flare light other than the rays of flare light (F8 and F9) is reflected specularly by the surface of the transfer belt 2040.

Figure 62:
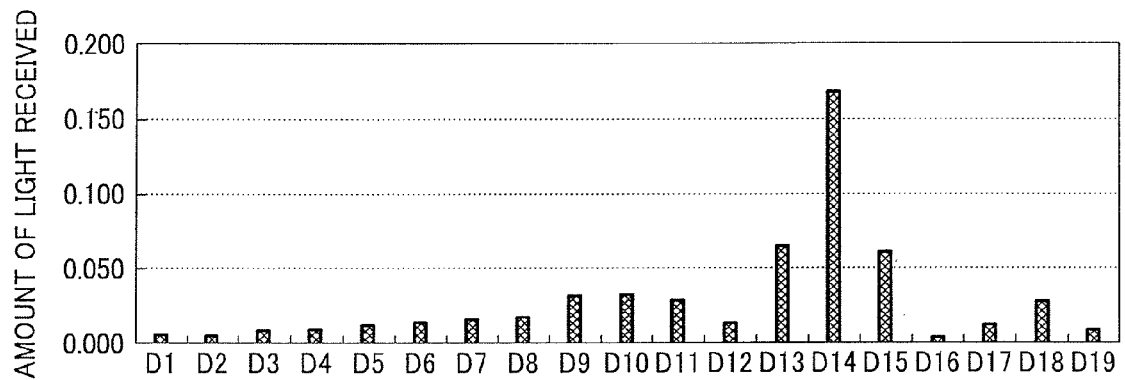
FIG. 62 is a graph of the amount of light received at each light-receiving element in the situation shown in FIG. 60 (second calculated amount of light received)

The processing device of each detection sensor calculates the amount of light received at each light-receiving element on the basis of the signal received from the corresponding light-receiving element, and stores the calculated amount in a memory (not shown). The calculated amounts of light received at the individual light-receiving elements are shown in FIG. 62. Hereinafter, the amount of light received that is calculated in the above-described embodiment is called "first calculated amount of light received" and the amount of light received that is calculated in this example is called "second calculated amount of light received".

A. The processing device of each detection sensor separates the second calculated amount of light received into the amount of diffusely reflected light received and the amount of specularly reflected light received.

A-1. Light-Receiving Elements D9 to D11

The second calculated amount of light received at each light-receiving element is larger than the first calculated amount of light received. This is because the flare light F8 diffusely reflected is received at each light-receiving element. The amount of specularly reflected light contained in the second calculated amount of light received is equal to the amount of specularly reflected light contained in the first calculated amount of light received. Therefore, the amount of diffusely reflected light contained in the second calculated amount of light received is calculated by subtracting, from the second calculated amount of light received, the amount of specularly reflected light contained in the first calculated amount of light received.

A-2. Light-Receiving Elements D4, D8, D12, and D16

The second calculated amount of light received at each light-receiving element is larger than the first calculated amount of light received. This is because the flare light F8 diffusely reflected is received at each light-receiving element.

Therefore, the second calculated amount of light received at each light-receiving element is completely due to the diffusely reflected light.

A-3. Light-Receiving Elements D5 to D7, D13 to D15, and D17 to D19

The second calculated amount of light received at each light-receiving element is larger than the first calculated amount of light received. This is because the flare light F8 diffusely reflected is received at each light-receiving element. The amount of specularly reflected light contained in the second calculated amount of light received is equal to the amount of specularly reflected light contained in the first calculated amount of light received. Therefore, the amount of diffusely reflected light contained in the second calculated amount of light received is calculated by subtracting, from the second calculated amount of light received, the amount of specularly reflected light contained in the first calculated amount of light received.

A-4. Light-Receiving Elements D1 to D3

The second calculated amount of light received at each light-receiving element is smaller than the first calculated amount of light received. This is because the flare light F8 strikes the rectangular pattern instead of the surface of the transfer belt 2040. The reflectance of the rectangular pattern is almost free from change in the incident angle. Therefore, the amount of diffusely reflected light contained in the second calculated amount of light received is calculated in the following procedure. The ratio C is calculated by dividing the second referential amount of light received at the light-receiving element D10 by the first referential amount of light received at the light-receiving element D10 (Step 1). The amount of specularly reflected light contained in the second referential amount of light received at each of the light-receiving elements (D1 to D3) is multiplied by the ratio C (Step 2). The calculated value is the amount of specularly reflected light contained in the second calculated amount of light received at each of the light-receiving elements (D1 to D3) (hereinafter, "amount of light received d"). The amount of light received d is subtracted from the second calculated amount of light received at each of the light-receiving elements (D1 to D3) (Step 3). The calculated value is the amount of diffusely reflected light contained in the second calculated amount of light received at each of the light-receiving elements (D1 to D3).

Figure 63:
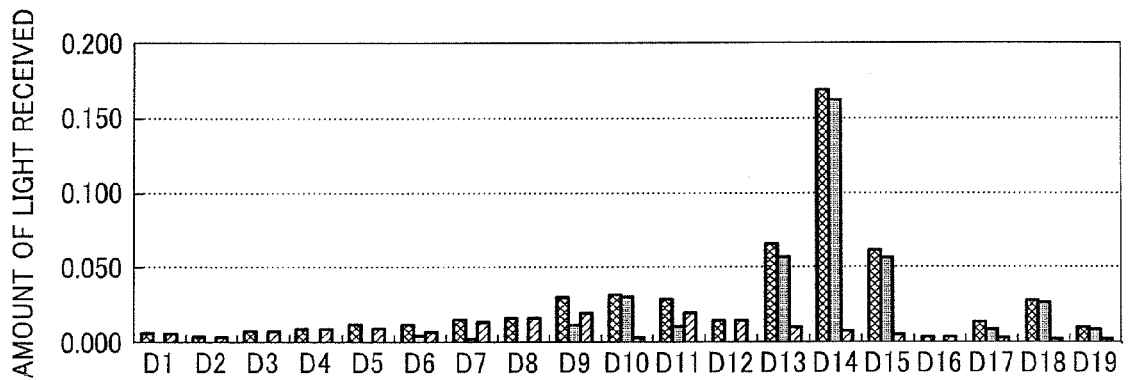
FIG. 63 is a graph of the second calculated amount of light received that is separated into the amount of specularly reflected light received and the amount of diffusely reflected light received.

The amount of diffusely reflected light and the amount of specularly reflected light contained in the second calculated amount of light received when the detection light S10 and the two rays of flare light (F8 and F9) strike the rectangular pattern are calculated to divide in this manner and the result of the calculation is shown in FIG. 63.

Figure 64:
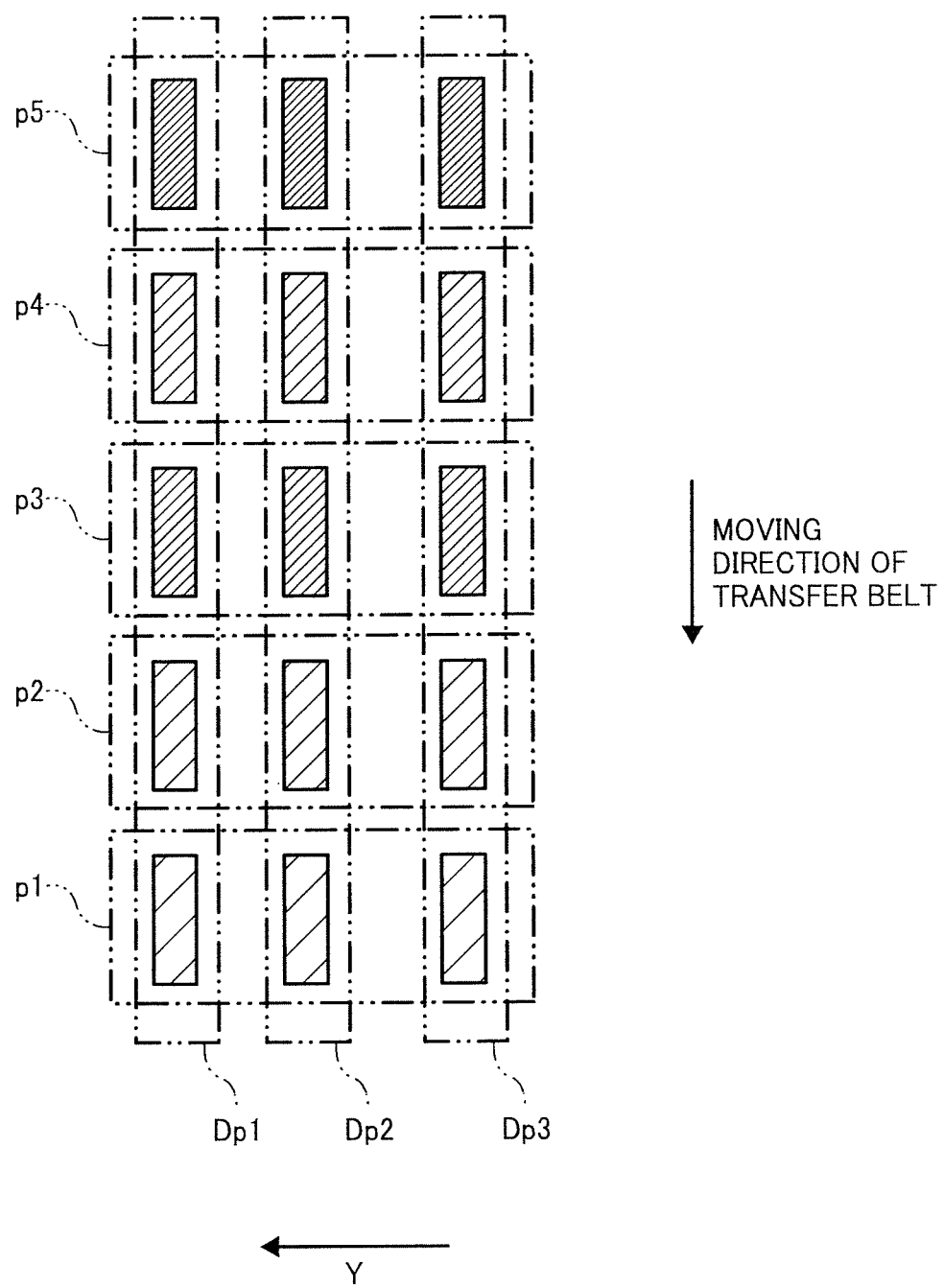
FIG. 64 is a schematic diagram of a toner pattern that is a modification of FIG. 60.

As one modification of this example, it is allowable to separate, as shown in FIGS. 64 to 66 for example, the rectangular pattern into three small rectangular patterns so that the detection light S10 and the two rays of flare light (F8 and F9) strike the three small rectangular patterns (Dp1 to Dp3), respectively. With this configuration, the amount of toner consumed decreases with the accuracy in the toner-density calculation maintained high. The length of each small rectangular pattern in the Y-axis direction is set about 1 mm.

As an example of the above-described embodiment, it is allowable to configure the printer control device 2090 to send, when the toner-density calculating process starts, the size and the position of the toner pattern to be formed to the scanning control device so that the toner pattern is formed at the specific position with the size appropriate to be exposed to the spot of the detection light S10 and the spots of the two rays of flare light (F11 and F12).

Figure 69:
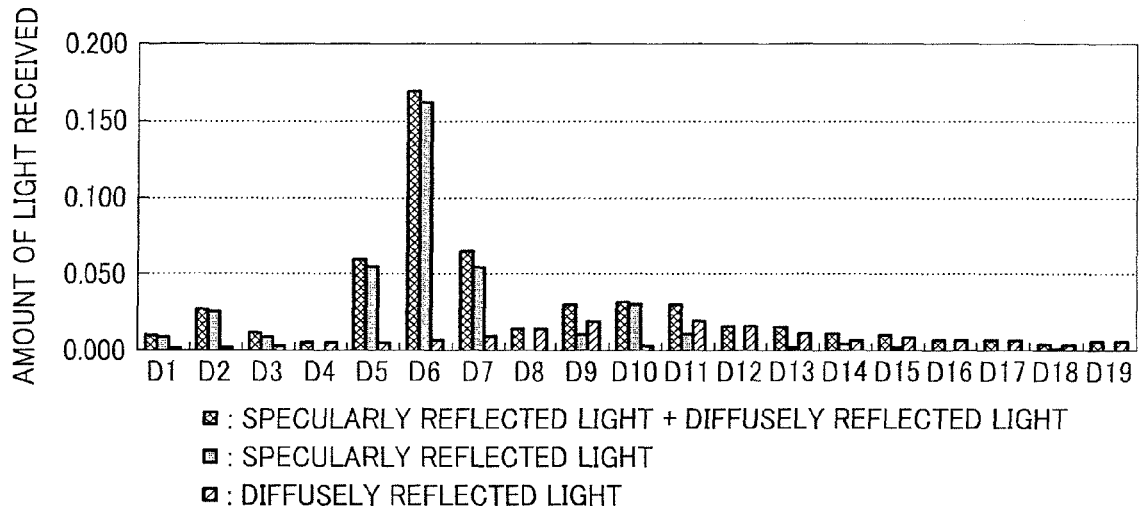
FIG. 69 is a graph of the amount of light received at each light-receiving element in the situation shown in FIG. 67.

In this case, as shown in FIG. 67 for example, when the rectangular pattern is in front of the detection sensor, the detection light S10 and the two rays of flare light (F11 and F12) strike the rectangular pattern, while the flare light other than the rays of flare light (F11 and F12) strikes the transfer belt 2040. As a result, as shown in FIG. 68 for example, the detection light S10 and the two rays of flare light (F11 and F12) are reflected specularly and diffusely by the rectangular pattern, while the flare light other than the rays of flare light (F11 and F12) is reflected specularly by the surface of the transfer belt 2040. The processing device of each detection sensor can separate the amount of light received at each light-receiving element into the amount of diffusely reflected light received and the amount of specularly reflected light received in the same manner as described with the example when the detection light S10 and the two rays of flare light (F8 and F9) strike the rectangular pattern. The amount of diffusely reflected light and the amount of specularly reflected light contained in the amount of light received when the detection light S10 and the two rays of flare light (F11 and F12) strike the rectangular pattern received are calculated and the result of the calculation is shown in FIG. 69.

Figure 70:
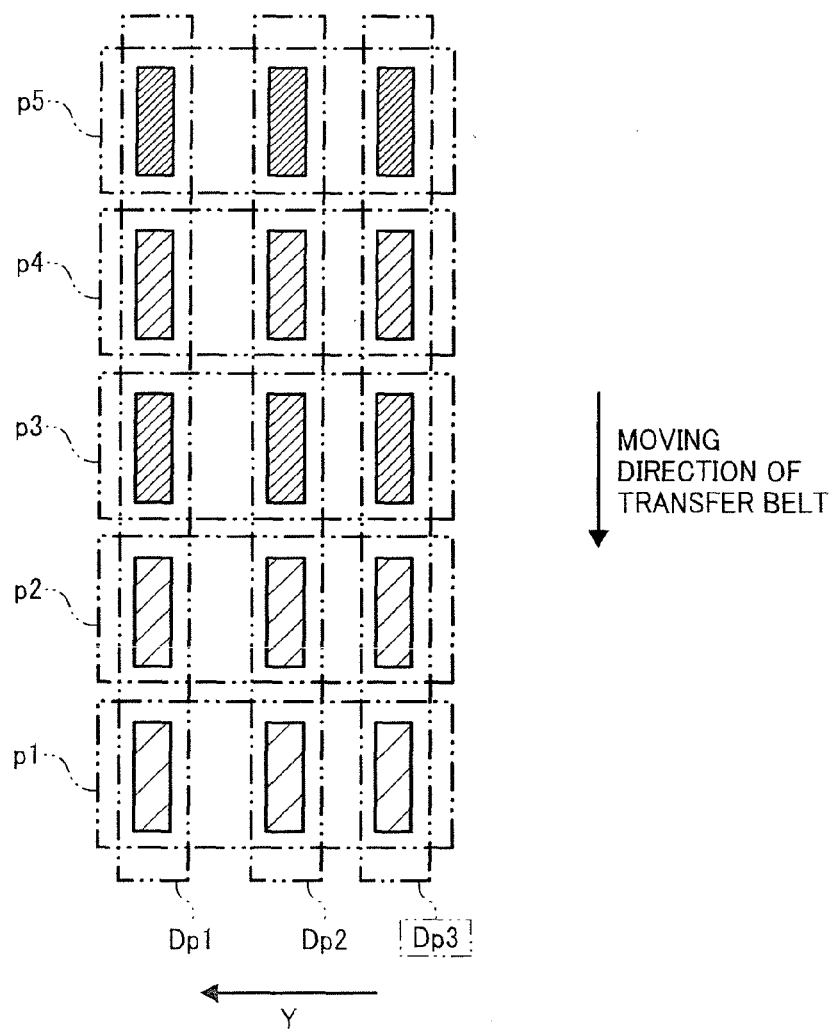
FIG. 70 is a schematic diagram of a toner pattern that is a modification of FIG. 67.

As one modification of this example, it is allowable to separate, as shown in FIGS. 70 to 72 for example, the rectangular pattern into three small rectangular patterns so that the detection light S10 and the two rays of flare light (F11 and F12) strike the three small rectangular patterns (Dp1 to Dp3), respectively. With this configuration, the amount of toner consumed decreases with the accuracy in the toner-density calculation maintained high. The length of each small rectangular pattern in the Y-axis direction is set about 1 mm.

As an example of the above-described embodiment, it is allowable to configure the printer control device 2090 to send, when the toner-density calculating process starts, the size and the position of the toner pattern to be formed to the scanning control device so that the toner pattern is formed at the specific position with the size appropriate to be exposed to the spot of the detection light S10 and the spot of the two rays of flare light (F9 and F11).

In this case, as shown in FIG. 73 for example, when the rectangular pattern is in front of the detection sensor, the detection light S10 and the two rays of flare light (F9 and F11) strike the rectangular pattern, while the flare light other than the rays of flare light (F9 and F11) strikes the transfer belt 2040. As a result, as shown in FIG. 74 for example, the detection light S10 and the two rays of flare light (F9 and F11) are reflected specularly and diffusely by the rectangular pattern, while the flare light other than the rays of flare light (F9 and F11) is reflected specularly by the surface of the transfer belt 2040.

Figure 75:
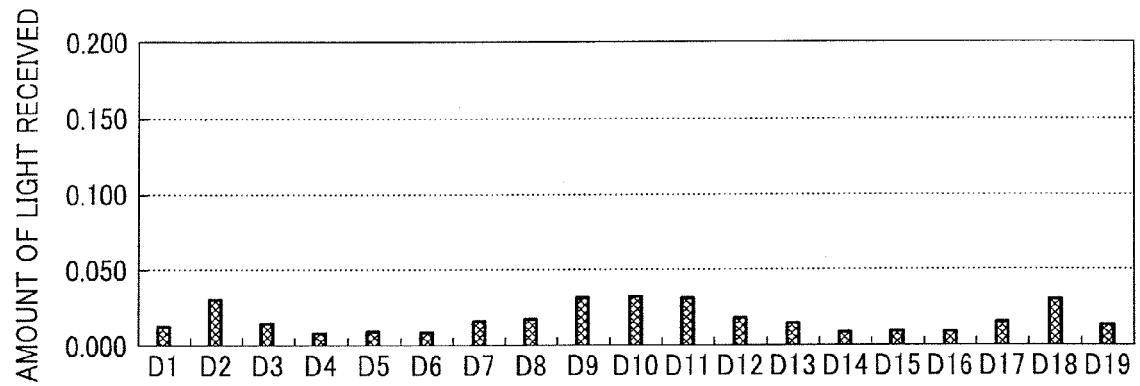
FIG. 75 is a graph of the amount of light received at each light-receiving element in the situation shown in FIG. 73 (third calculated amount of light received)

The processing device of each detection sensor calculates the amount of light received at each light-receiving element on the basis of the signal received from the corresponding light-receiving element and stores the calculated amount in a memory (not shown). The calculated amounts of light received at the individual light-receiving elements are shown in FIG. 75. Hereinafter, the calculated amount of light received is called "third calculated amount of light received".

B. The processing device of each detection sensor separates the third calculated amount of light received into the amount of diffusely reflected light received and the amount of specularly reflected light received.

B-1. Light-Receiving Elements D9 to D11

The third calculated amount of light received at each light-receiving element is larger than the first calculated amount of light received. This is because the flare light F9 diffusely reflected is received at each light-receiving element. The amount of specularly reflected light contained in the third calculated amount of light received is equal to the amount of specularly reflected light contained in the first calculated amount of light received. Therefore, the amount of diffusely reflected light contained in the third calculated amount of light received is calculated by subtracting, from the third calculated amount of light received, the amount of specularly reflected light contained in the first calculated amount of light received.

B-2. Light-Receiving Elements D4, D8, D12, and D16

The third calculated amount of light received at each light-receiving element is larger than the first calculated amount of light received. This is because the flare light F9 diffusely reflected is received at each light-receiving element. Therefore, the third calculated amount of light received at each light-receiving element is completely due to the diffusely reflected light.

B-3. Light-Receiving Elements D1 to D3, D5 to D7, D17 to D19

The third calculated amount of light received at each light-receiving element is larger than the first calculated amount of light received. This is because the flare light F9 diffusely reflected is received at each light-receiving element. The amount of specularly reflected light contained in the third calculated amount of light received is equal to the amount of specularly reflected light contained in the first calculated amount of light received. Therefore, the amount of diffusely reflected light contained in the third calculated amount of light received is calculated by subtracting, from the third calculated amount of light received, the amount of specularly reflected light contained in the first calculated amount of light received.

B-4. Light-Receiving Elements D13 to D15

The third calculated amount of light received at each light-receiving element is smaller than the first calculated amount of light received. This is because the flare light F9 strikes the rectangular pattern instead of the surface of the transfer belt 2040. The reflectance of the rectangular pattern is almost free from change in the incident angle. Therefore, the amount of diffusely reflected light contained in the third calculated amount of light received is calculated in the following procedure. The ratio C is calculated by dividing the second referential amount of light received at the light-receiving element D10 by the first referential amount of light received at the light-receiving element D10 (Step 1). The amount of specularly reflected light contained in the third referential amount of light received at each of the light-receiving elements (D13 to D15) is multiplied by the ratio C (Step 2). The calculated value is the amount of specularly reflected light contained in the third calculated amount of light received at each of the light-receiving elements (D13 to D15) (hereinafter, "amount of light received e"). The amount of light received e is subtracted from the third calculated amount of light received at each of the light-receiving elements (D13 to D15) (Step 3). The calculated value is the amount of diffusely reflected light contained in the third calculated amount of light received at each of the light-receiving elements (D13 to D15).

Figure 76:
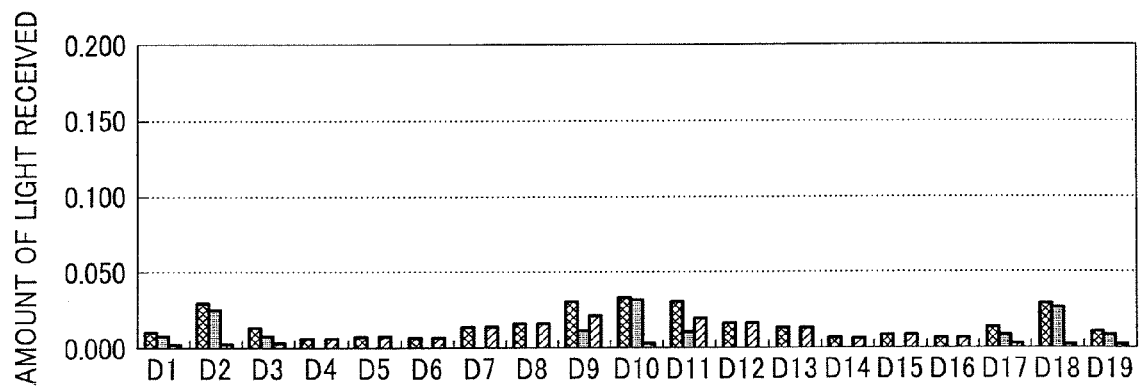
FIG. 76 is a graph of the third calculated amount of light received that is separated into the amount of specularly reflected light received and the amount of diffusely reflected light received.

The amount of diffusely reflected light and the amount of specularly reflected light contained in the third calculated amount of light received when the detection light S10 and the two rays of flare light (F9 and F11) strike the rectangular pattern are calculated in this manner and the result of the calculation is shown in FIG. 76.

Figure 77:
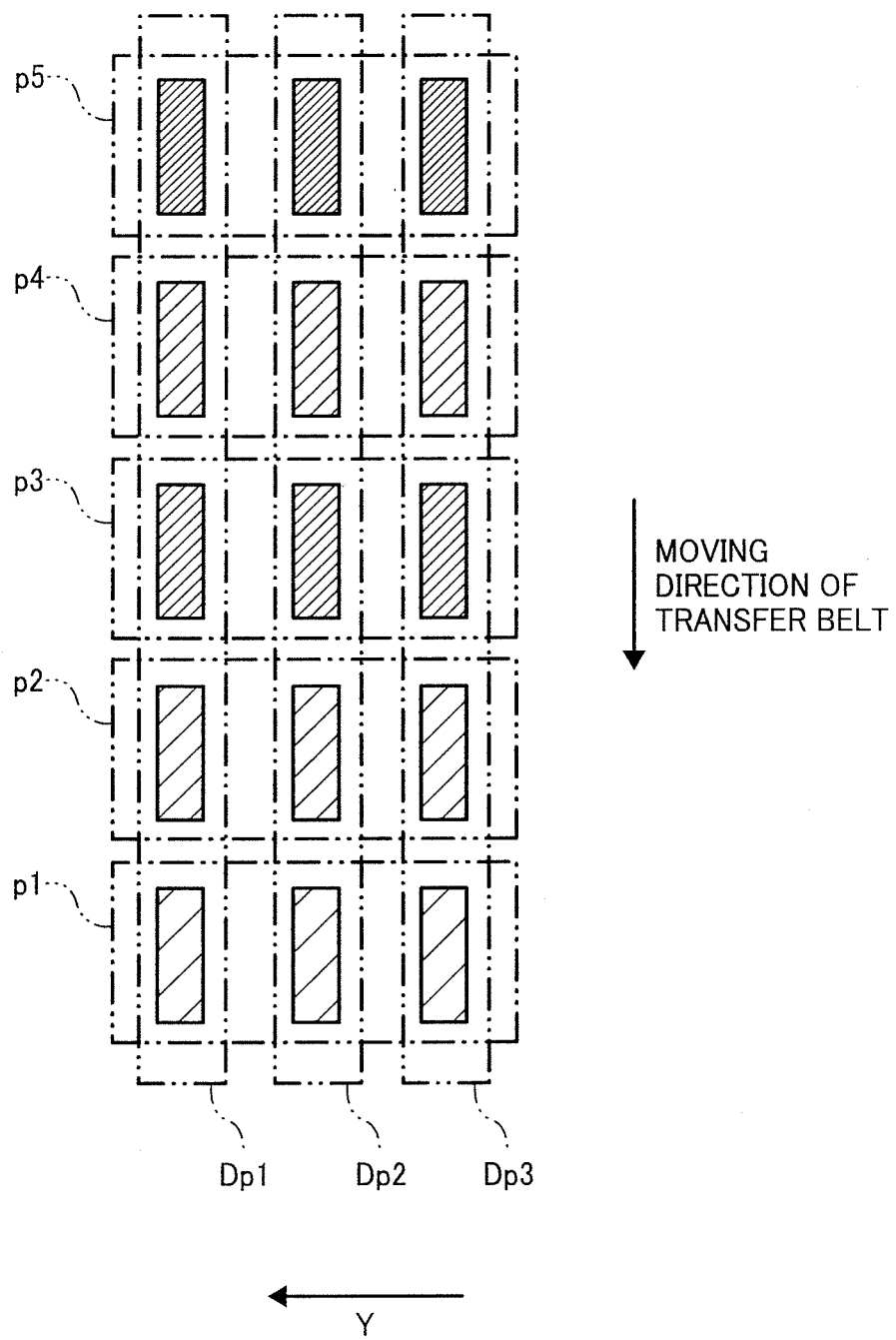
FIG. 77 is a schematic diagram of a toner pattern that is a modification of FIG. 73.

As one modification of this example, it is allowable to separate, as shown in FIGS. 77 to 79 for example, the rectangular pattern into three small rectangular patterns so that the detection light S10 and the two rays of flare light (F9 and F11) strike the three small rectangular patterns (Dp1 to Dp3), respectively. With this configuration, the amount of toner consumed decreases with the accuracy in the toner-density calculation maintained high. The length of each small rectangular pattern in the Y-axis direction is set about 1 mm.

As an example of the above-described embodiment, it is allowable to configure the printer control device 2090 to send, when the toner-density calculating process starts, the size and the position of the toner pattern to be formed to the scanning control device so that the toner pattern is formed at the specific position with the size appropriate to be exposed to the spot of the detection light S10 and the spots of the four rays of flare light (F8, F9, F11, and F12).

In this case, as shown in FIG. 80 for example, when the rectangular pattern is in front of the detection sensor, the detection light S10 and the four rays of flare light (F8, F9, F11, and F12) strike the rectangular pattern. As a result, as shown in FIG. 81 for example, the detection light S10 and the four rays of flare light (F8, F9, F11, and F12) are reflected specularly and diffusely by the rectangular pattern.

Figure 82:
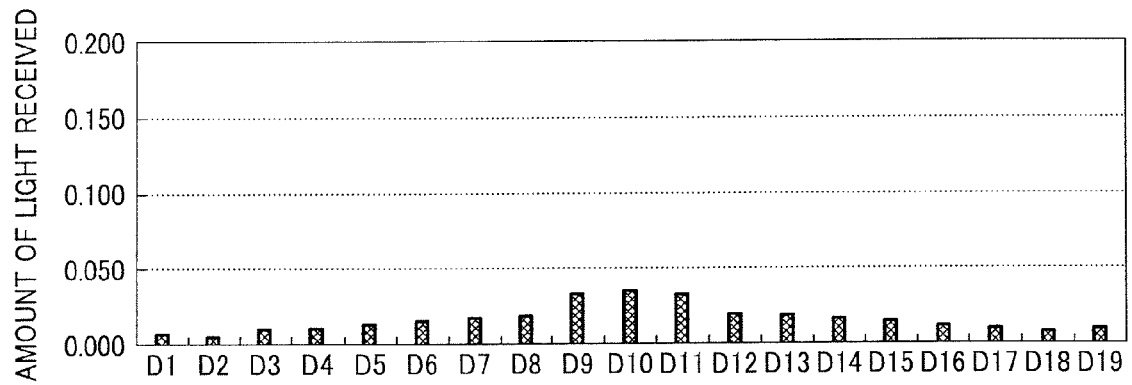
FIG. 82 is a graph of the amount of light received at each light-receiving element in the situation shown in FIG. 80 (fourth calculated amount of light received)

The processing device of each detection sensor calculates the amount of light received at each light-receiving element on the basis of the signal received from the corresponding light-receiving element and stores the calculated amount in a memory (not shown). The calculated amounts of light received at the individual light-receiving elements are shown in FIG. 82. Hereinafter, the calculated amount of light received is called "fourth calculated amount of light received".

C. The processing device of each detection sensor separates the fourth calculated amount of light received into the amount of diffusely reflected light received and the amount of specularly reflected light received.

C-1. Light-Receiving Elements D9 to D11

The fourth calculated amount of light received at each light-receiving element is larger than the second calculated amount of light received. This is because the rays of flare light F8 and F9 diffusely reflected are received at each light-receiving element. The amount of specularly reflected light contained in the fourth calculated amount of light received is equal to the amount of specularly reflected light contained in the second calculated amount of light received. Therefore, the amount of diffusely reflected light contained in the fourth calculated amount of light received is calculated by subtracting, from the fourth calculated amount of light received, the amount of specularly reflected light contained in the second calculated amount of light received.

C-2. Light-Receiving Elements D4, D8, D12, and D16

The fourth calculated amount of light received at each light-receiving element is larger than the second calculated amount of light received. This is because the flare light F8 and F9 diffusely reflected light are received at each light-receiving element. Therefore, the fourth calculated amount of light received at each light-receiving element is completely due to the diffusely reflected light.

C-3. Light-Receiving Elements D1 to D3 and D5 to D7

The fourth calculated amount of light received at each light-receiving element is larger than the second calculated amount of light received. This is because the rays of flare light F8 and F9 diffusely reflected are received at each light-receiving element. The amount of specularly reflected light contained in the fourth calculated amount of light received is equal to the amount of specularly reflected light contained in the second calculated amount of light received. Therefore, the amount of diffusely reflected light contained in the fourth calculated amount of light received is calculated by subtracting, from the fourth calculated amount of light received, the amount of specularly reflected light contained in the second calculated amount of light received.

C-4. Light-Receiving Elements D13 to D15 and D17 to D19

The fourth calculated amount of light received at each light-receiving element is smaller than the second calculated amount of light received. This is because the rays of flare light F8 and F9 strike the rectangular pattern instead of the surface of the transfer belt 2040. The reflectance of the rectangular pattern is almost free from change in the incident angle. Therefore, the amount of diffusely reflected light contained in the fourth calculated amount of light received is calculated in the following procedure. The ratio C is calculated by dividing the second referential amount of light received at the light-receiving element D10 by the first referential amount of light received at the light-receiving element D10 (Step 1). The amount of specularly reflected light contained in the second referential amount of light received at each of the light-receiving elements (D13 to D15 and D17 to D19) is multiplied by the ratio C (Step 2). The calculated value is the amount of specularly reflected light contained in the fourth calculated amount of light received at each of the light-receiving elements (D13 to D15 and D17 to D19) (hereinafter, "amount of light received f"). The amount of light received f is subtracted from the fourth calculated amount of light received at each of the light-receiving elements (D13 to D15 and D17 to D19) (Step 3). The calculated value is the amount of diffusely reflected light contained in the fourth calculated amount of light received at each of the light-receiving elements (D13 to D15 and D17 to D19).

Figure 83:
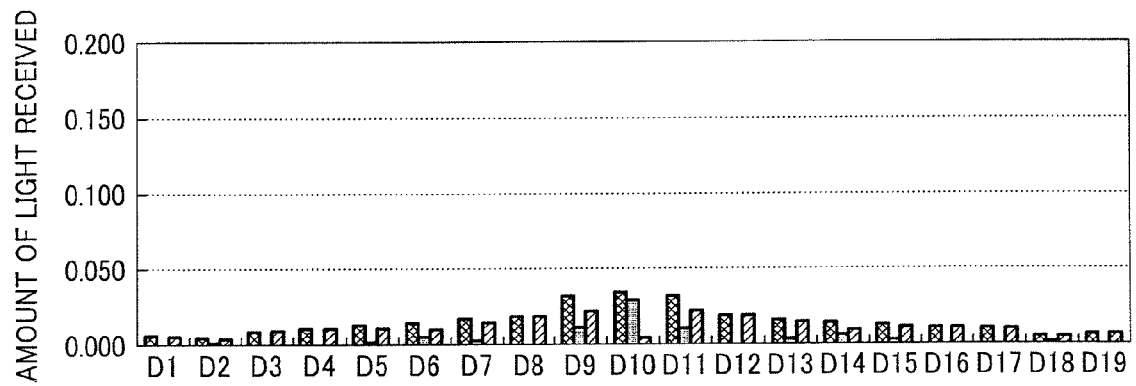
FIG. 83 is a graph of the fourth calculated amount of light received that is separated into the amount of specularly reflected light received and the amount of diffusely reflected light received.

The amount of diffusely reflected light and the amount of specularly reflected light contained in the fourth calculated amount of light received when the detection light S10 and the four rays of flare light (F8, F9, F11 and F12) strike the rectangular pattern are calculated and divided in this manner and the result of the calculation is shown in FIG. 83.

Figure 84:
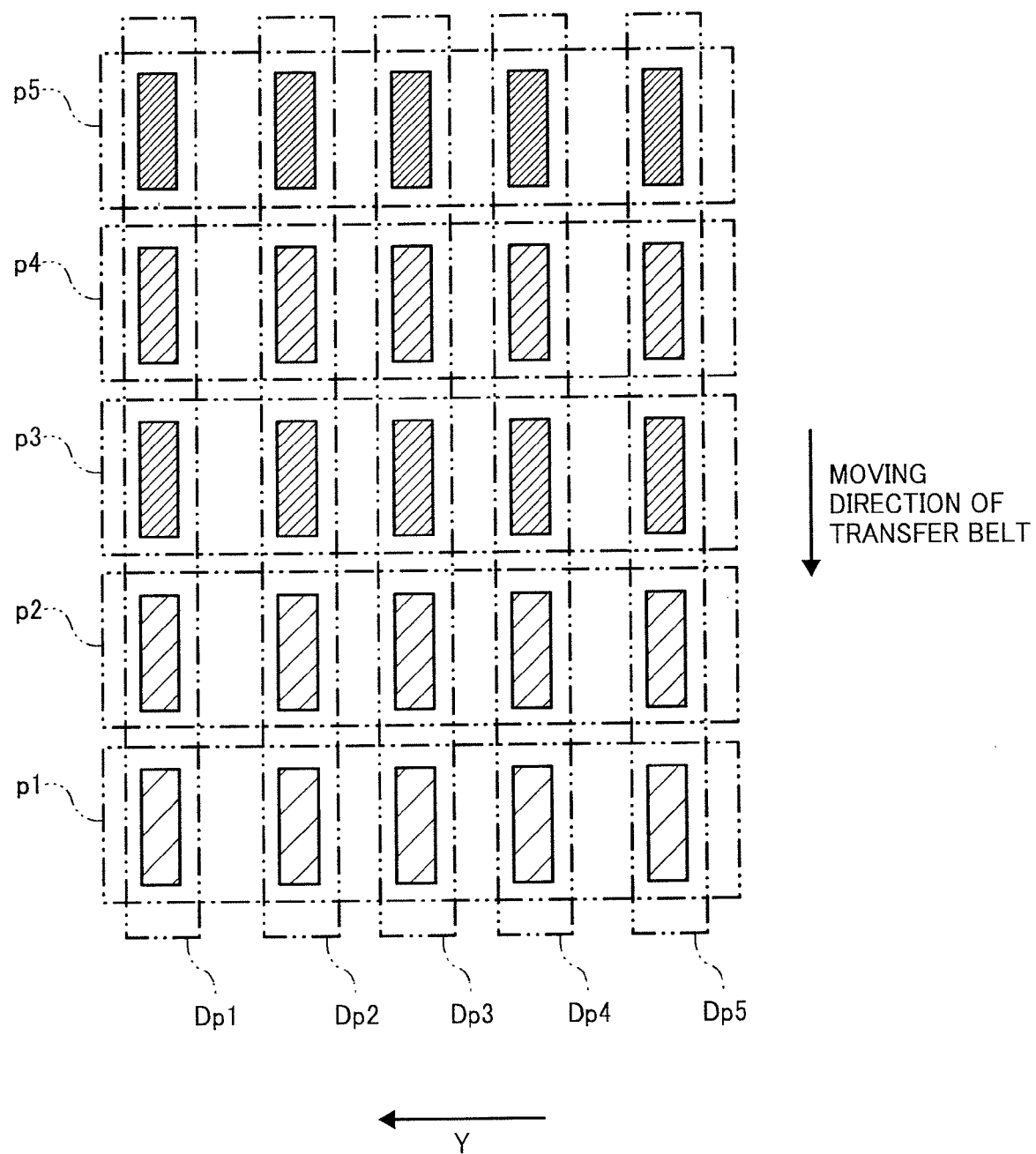
FIG. 84 is a schematic diagram of a toner pattern that is a modification of FIG. 80.

As one modification of this example, it is allowable to separate, as shown in FIGS. 84 to 86 for example, the rectangular pattern into five small rectangular patterns so that the detection light S10 and the four rays of flare light (F8, F9, F11 and F12) strike the five small rectangular patterns (Dp1 to Dp5), respectively. With this configuration, the amount of toner consumed decreases with the accuracy in the toner-density calculation maintained high. The length of each small rectangular pattern in the Y-axis direction is set about 1 mm.

As an example of the above-described embodiment, as shown in FIG. 87, it is allowable to use the detection-light collecting lens system LEA that includes the nineteen detection-light collecting lenses as one unit, instead of the nineteen detection-light collecting lenses (LE1 to LE19). This configuration improves the efficiency in attaching the detection-light collecting lenses to the detection sensor. Moreover, this improves the accuracy in arrangement of the detection-light collecting lenses. Although, in the detection-light collecting lens system LEA, only the surface that receives incoming light has a light-gathering power, the surface from which light exits can be configured to have a light-gathering power. The lens surface can be formed on a glass substrate or a resin substrate using photolithography technology or nanoimprint technology.

Figure 89:
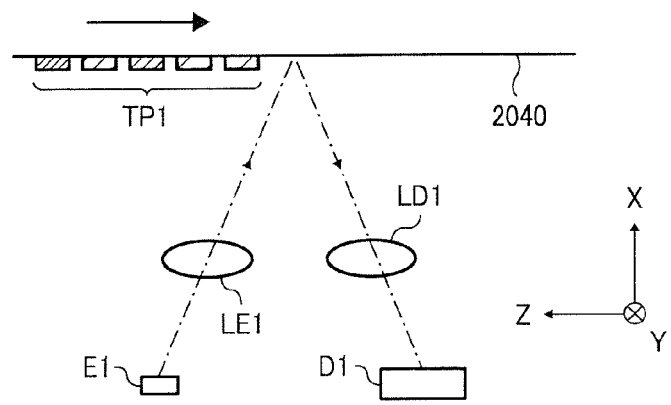
FIG. 89 is a second schematic diagram of the modified light-emitting system.
Figure 90:
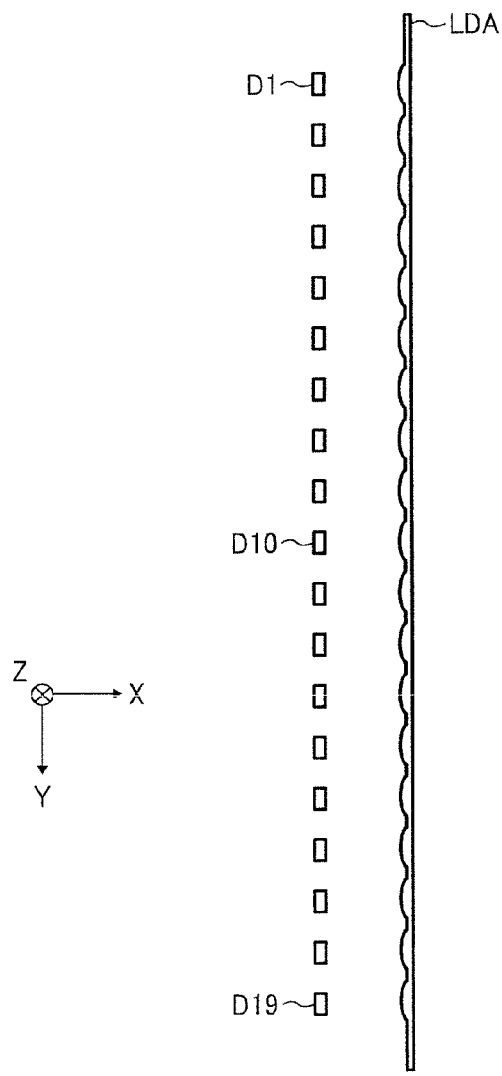
FIG. 90 is a schematic diagram of a system that includes nineteen reflected-light collecting lenses as an integrated unit.

As another example of the above-described embodiment, as shown in FIGS. 88 to 89 for example, each detection sensor can further include, nineteen reflected-light collecting lenses (LD1 to LD19) that correspond to the nineteen light-receiving elements, respectively. Each of the reflected-light collecting lenses LD1 to LD19 is, for example, a spherical lens or an anamorphic lens having light-gathering powers in both the Y-axis direction and the Z-axis direction. By presence of the reflected-light collecting lenses, the condensed reflected light is received at the corresponding light-receiving element. As one modification of this example as shown in FIG. 90 for example, it is allowable to use a reflected-light collecting lens system LDA that includes nineteen reflected-light collecting lenses that correspond to the light-receiving element, respectively as a unit instead of the nineteen reflected-light collecting lenses (LD1 to LD19). This configuration improves the efficiency in attaching the reflected-light collecting lenses to the detection sensor. Moreover, this improves the accuracy in arrangement of the reflected-light collecting lenses. Although, in the reflected-light collecting lens system LDA, only the surface that receives incoming light has a light-gathering power, the surface from which light exits can be configured to have a light-gathering power.

Figure 91:
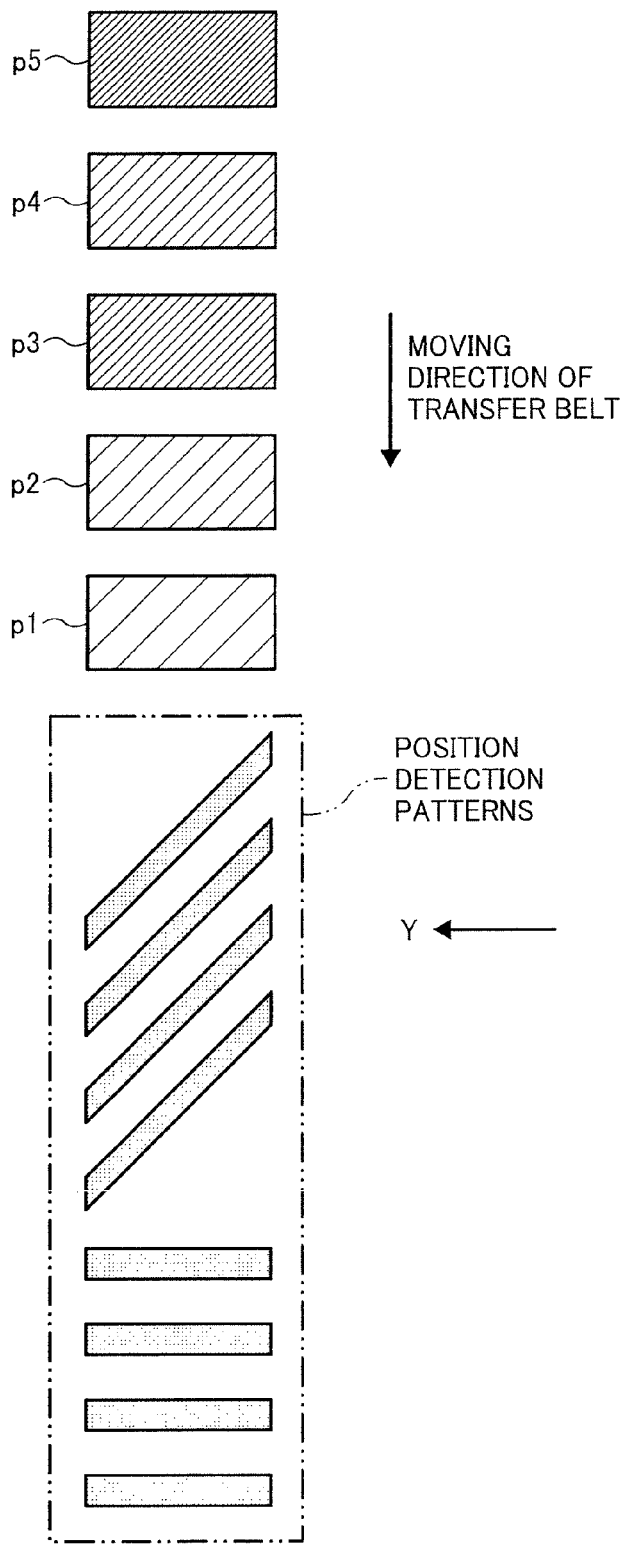
FIG. 91 is a schematic diagram of a position detection pattern.

Moreover, in the above-described embodiment, it is allowable to form, upstream of the toner pattern, a position detection pattern shown in FIG. 91 for example (see, for example, Japanese Patent Application Laid-open No. 2008-276010 and Japanese Patent Application Laid-open No. 2005-238584) that is used to determine whether the position of the spot of light on the photosensitive element is correct. With this configuration, the position of the toner pattern in the Y-axis direction can be calculated using the position-detection pattern.

Figure 92:
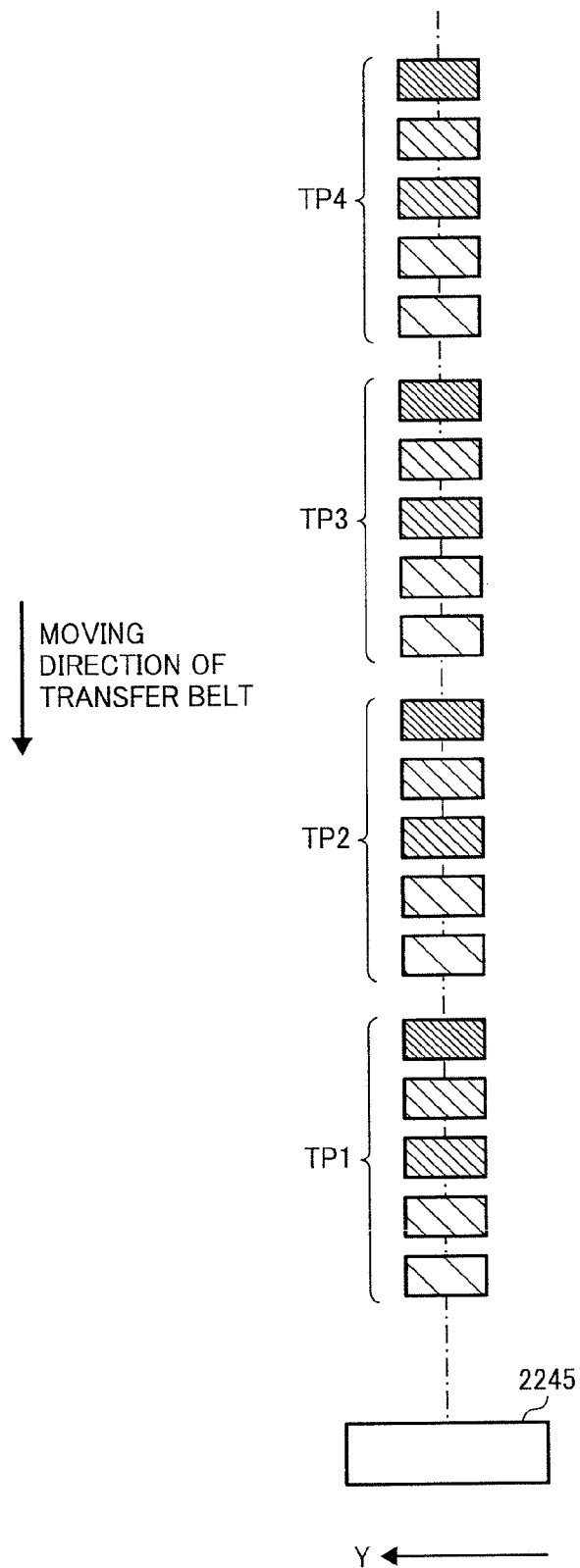
FIG. 92 is a schematic diagram of a modified toner pattern.

Furthermore, in the above-described embodiment, as shown in FIG. 92 for example, it is allowable to arrange the toner patterns TP1 to TP4 in a row along the moving direction of the transfer belt 2040. In this case, it is enough for the toner-density calculator 2245 to include only one detection sensor.

Moreover, in the above-described embodiment, part of process performed by the detection sensor can be performed by the printer control device 2090 instead.

Although, during the toner-density calculating process according to the above-described embodiment, the first referential amount of light received and the first referential amount of light received are calculated before the calculated amount of light received is calculated, some other manners can be taken. It is allowable, for example, to calculate either the first referential amount of light received or the first referential amount of light received or both of them when the power is switched ON or during the stand-by state and stores it in a memory (not shown). This makes the time taken for the toner-density calculating process shorter.

In the above-described embodiment, the light-emitting element E10 is in operation during the toner-density calculating process; however, the on-state light-emitting element can be some other depending on the position of the toner pattern.

Although the detection sensor used in the above-described embodiment includes nineteen light-emitting elements, the number of the light-emitting elements can be any value larger than two.

Although, in the above-described embodiment, the nineteen light-emitting elements (E1 to E19) are arranged in a row along the Y-axis direction, the light-emitting elements can be arranged in some other manners. It is allowable, for example, to arrange the light-emitting elements in a direction that makes an angle with the Y-axis direction or as a plurality of lines along the Y-axis direction in zigzag arrangement. The light-emitting elements can be arranged in any manners as long as the light-emitting elements are arranged at equal intervals.

Although, in the above-described embodiment, the number of the light-emitting elements and the number of the light-receiving elements are equal, they can be unequal.

Although, in the above-described embodiment, the toner pattern is formed on the transfer belt 2040, the toner pattern can be formed on some other members, for example, the photosensitive element, if possible, or the intermediate transfer belt.

Although, in the above-described embodiment, the color printer 2000 that includes the plurality of the photosensitive elements is used as the image forming apparatus, some other types of image forming apparatus, for example, a monochrome printer that includes one photosensitive element can be used, instead.

Moreover, a copier, a facsimile machine, or a multifunction produce that has any of a printer function, a copy function, and a facsimile function can be used, instead.

As described above, a toner-density calculating sensor and a toner-density calculating method according to the present embodiment can calculates the toner density accurately even if a detection pattern is small. Moreover, an image forming apparatus according to the present embodiment can improve the efficiency in image formation with the image quality maintained high.

To achieve the above-described object, in the present embodiment, an output from each light-receiving element included in a reflective optical sensor is separated into the amount of specularly reflected light and the amount of diffusely reflected light. Because components (detection information) contained in output from each light-receiving element are identified in this manner, an accurate toner density can be calculated using almost all of the necessary data.

According to the present embodiment, an output from each light-receiving element is separated into the amount of specularly reflected light and the amount of diffusely reflected light and thus an accurate toner density can be calculated using all of the necessary outputs from light-receiving elements. As a result, the accuracy in the toner-density calculation is improved.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A toner-density detection sensor comprising:
at least three light-emitting units and at least three light-receiving units, wherein when any of the at least three light-emitting units is on, the light-emitting unit emits one detection light and at least one flare light and the toner-density detection sensor detects a toner density of a detection pattern that is formed on a medium; and
a processing device that calculates, as a detected amount of light received, an amount of light received at each of the light-receiving units when the detection pattern is illuminated with the detection light and the at least one flare light and calculates the toner density of the detection pattern in accordance with the detected amount of light received.

2. The toner-density detection sensor according to claim 1, wherein the processing device calculates the toner density of the detection pattern by referring to a first referential amount of light received and a second referential amount of light received, the first referential amount of light received is an amount of light received at each of the light-receiving units when the medium is illuminated with the detection light and the at least one flare light, and the second referential amount of light received is an amount of light received at each of the light-receiving units when the detection pattern is illuminated with the detection light only.

3. The toner-density detection sensor according to claim 2, wherein the processing device separates, by referring to the first referential amount of light received and the second referential amount of light received, the detected amount of light received into an amount of diffusely reflected light and an amount of specularly reflected light.

4. The toner-density detection sensor according to claim 2, wherein the processing device calculates the first referential amount of light received in accordance with an output signal of the at least three light-receiving units that is obtained when the medium is illuminated with the detection light and the at least one flare light.

5. The toner-density detection sensor according to claim 2, wherein the processing device calculates the second referential amount of light received in accordance with an output signal of the at least three light-receiving units that is obtained when the detection pattern is illuminated with the detection light only and when the medium is illuminated with the at least one flare light.

6. The toner-density detection sensor according to claim 1, wherein the at least one flare light is a plurality of flare lights, and the processing device calculates the detected amount of light received in accordance with an output signal of the at least three light-receiving units that is obtained when the detection pattern is illuminated with the detection light and the plurality of flare lights.

7. The toner-density detection sensor according to claim 1, wherein the at least one flare light is a plurality of flare lights, and the processing device calculates the detected amount of light received in accordance with an output signal of the at least three light-receiving units that is obtained when the detection pattern is illuminated with the detection light and part of the plurality of flare lights.

8. The toner-density detection sensor according to claim 1, wherein when the detection pattern is illuminated with the detection light and the at least one flare light, the at least three light-receiving units includes one light-receiving unit that receives diffusely reflected flare light and another light-receiving unit that receives specularly reflected flare light.

9. An image forming apparatus comprising: an image carrier; an optical scanning device that scans the image carrier by moving, in a main-scanning direction, a light ray that is modulated in accordance with image information to form a latent image on the image carrier; a developing device that attaches toner onto the latent image to form a toner image; a transferring device that transfers the toner image onto a medium; and the toner-density detection sensor according to claim 1 that detects toner density of a detection pattern that has been transferred onto the medium.

10. The image forming apparatus according to claim 9 further comprising: a control device that causes the optical scanning device to form the detection pattern, wherein for calculation of the detected amount of light received by the processing device of the toner-density detection sensor, the control device causes the optical scanning device to form the detection pattern such that the detection pattern is illuminated with the detection light and the at least one flare light.

11. The image forming apparatus according to claim 10, wherein the control device causes the optical scanning device to form the detection pattern such that the detection pattern includes a plurality of patterns and the patterns are illuminated with the detection light and the at least one flare light, individually.

12. The image forming apparatus according to claim 10, wherein, for calculation of a second referential amount of light received that is referred by the processing device of the toner-density detection sensor, the control device causes the optical scanning device to form the detection pattern such that the detection pattern is illuminated with the detection light only.

13. The image forming apparatus according to claim 10, wherein the control device adjusts an amount of toner attached by the developing device in accordance with either a sum of amounts of diffusely reflected light or a sum of amounts of specularly reflected light, both the amounts of diffusely reflected light and the amounts of specularly reflected light being included in the detected amount of light received.

14. The image forming apparatus according to claim 10, wherein the image information is information about a multi-color image, and the control device causes the optical scanning device to form the detection pattern of each color.

15. A toner-density detecting method of detecting a toner density of a detection pattern that is formed on a medium by using a toner density detection sensor that includes at least three light-emitting units and at least three light-receiving units in which, when any of the at least three light-emitting units is on, the light-emitting unit emits one detection light and at least one flare light, the method comprising:

calculating, in accordance with an output signal of the at least three light-receiving units that is obtained when the detection pattern is illuminated with the detection light and the at least one flare light, an amount of light received at each of the light-receiving units as a detected amount of light received; and calculating the toner density of the detection pattern in accordance with the detected amount of light received.

16. The toner-density detecting method according to claim 15, further comprising separating the detected amount of light received into an amount of diffusely reflected light and an amount of specularly reflected light.

17. The toner-density detecting method according to claim 16, further comprising: illuminating, before the separating, the medium with the detection light, and calculating, in accordance with an output signal of the at least three light-receiving units, an amount of light received at each of the light-receiving units as a first referential amount of light received.

18. The toner-density detecting method according to claim 16, further comprising: illuminating, before the separating, the detection pattern with the detection light and the medium with the at least one flare light, and calculating, in accordance with an output signal of the at least three light-receiving units, an amount of light received at each of the light-receiving units as a second referential amount of light received.

19. The toner-density detecting method according to claim 15, wherein during the calculating of the detected amount of light received, when the detection light is illuminated with the detection light and the at least one flare light, the at least three light-receiving units includes one light-receiving unit that receives diffusely reflected flare light and another light-receiving unit that receives specularly reflected flare light.

\* \* \* \* \*